(12) United States Patent
Holm et al.

(10) Patent No.: US 8,795,963 B2
(45) Date of Patent: Aug. 5, 2014

(54) GENETIC MARKERS FOR RISK MANAGEMENT OF ATRIAL FIBRILLATION AND STROKE

(75) Inventors: Hilma Holm, Mosfellsbaer (IS); Daniel Gudbjartsson, Reykjavik (IS)

(73) Assignee: deCODE Genetics ehf., Reykjavík (IS)

( * ) Notice: Subject to any disclaimer, the term of this patent is extended or adjusted under 35 U.S.C. 154(b) by 0 days.

(21) Appl. No.: 13/262,550

(22) PCT Filed: Mar. 30, 2010

(86) PCT No.: PCT/IS2010/050001
§ 371 (c)(1),
(2), (4) Date: Sep. 30, 2011

(87) PCT Pub. No.: WO2010/113185
PCT Pub. Date: Oct. 7, 2010

(65) Prior Publication Data
US 2012/0021989 A1    Jan. 26, 2012

(30) Foreign Application Priority Data

Apr. 3, 2009   (IS) .............................................. 8813

(51) Int. Cl.
*C12Q 1/68* (2006.01)
*C12P 19/34* (2006.01)
(52) U.S. Cl.
USPC ............ 435/6.1; 435/6.11; 435/6.12; 435/7.1
(58) Field of Classification Search
None
See application file for complete search history.

(56) References Cited

U.S. PATENT DOCUMENTS

| | | | |
|---|---|---|---|
| 4,376,110 A | 3/1983 | David et al. | |
| 5,223,409 A | 6/1993 | Ladner et al. | |
| 5,445,934 A | 8/1995 | Fodor et al. | |
| 5,700,637 A | 12/1997 | Southern | |
| 5,744,305 A | 4/1998 | Fodor et al. | |
| 5,945,334 A | 8/1999 | Besemer et al. | |
| 6,054,270 A | 4/2000 | Southern | |
| 6,300,063 B1 | 10/2001 | Lipshutz et al. | |
| 6,429,027 B1 | 8/2002 | Chee et al. | |
| 6,733,977 B2 | 5/2004 | Besemer et al. | |
| 6,858,394 B1 | 2/2005 | Chee et al. | |
| 7,364,858 B2 | 4/2008 | Barany et al. | |

FOREIGN PATENT DOCUMENTS

| | | |
|---|---|---|
| EP | 373 203 A1 | 6/1990 |
| EP | 619 321 A1 | 10/1994 |
| WO | WO-90/02809 A1 | 3/1990 |
| WO | WO-91/17271 A1 | 11/1991 |
| WO | WO-92/01047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-2004/028341 A2 | 4/2004 |
| WO | WO-2008/068780 A2 | 6/2008 |
| WO | WO-2009/117122 A2 | 9/2009 |

OTHER PUBLICATIONS dbSNP Submitted SNP(ss) Details: ss66564904 (Nov. 9, 2006), from www.ncbi.nlm.nih.gov, pp. 1-2.*
Hegele R.A. Arterioscler Thromb Vasc Biol. 2002;22:1058-1061.*
Pennisi E. Science; Sep. 18, 1998; 281, 5384; 1787-1789.*
Wall J.D. et al Nature Reviews—Genetics, vol. 4 (Aug. 2003) p. 587-597.*
GeneCards output for ZFHX3, from www.genecards.org, printed Jul. 11, 2013, pp. 1-11.*
Lambert C. "Missing Heritability and the Future of GWAS", (2010), from blog.goldenhelix.com, 2 printed pages.*
Lubitz S.A. et al. European Heart Journal (2013), pp. 1-3.*
Adams et al., Classification of subtype of acute ischemic stroke. Definitions for use in a multicenter clinical trial. TOAST. Trial of Org 10172 in Acute Stroke Treatment, Stroke, 24(1):35-41 (1993).
Agami et al., RNAi and related mechanisms and their potential use for therapy, Curr. Opin. Chem. Biol., 6:829-34 (2002).
Allard et al., PARK7 and nucleoside diphosphate kinase A as plasma markers for the early diagnosis of stroke, Clin. Chem., 51:2043-51 (2005).
Altschul et al., Gapped BLAST and PSI-BLAST: a new generation of protein database search programs, Nucleic Acids Res., 25:3389-402 (1997).
Amarzguioui et al., Approaches for chemically synthesized siRNA and vector-mediated RNAi, FEBS Lett., 579:5974-81 (2005).
Amendt et al., The molecular basis of Rieger syndrome. Analysis of Pitx2 homeodomain protein activities, J. Biol. Chem., 273(32):20066-72 (1998).
Amundadottir et al., A common variant associated with prostate cancer in European and African populations, Nat. Genet., 38:652-8 (2006).
Anselmi et al., Association of rs2200733 at 4q25 with atrial flutter/fibrillation diseases in an Italian population, Heart, 94(11):1394-6 (2008).
Baum et al., Methylenetetrahydrofolate reductase gene A222V polymorphism and risk of ischemic stroke, Clin. Chem. Lab. Med., 42:1370-6 (2004).
Becker, Biomarkers in atrial fibrillation: investigating biologic plausibility, cause, and effect, J. Thromb. Thombolys., 19:71-5 (2005).
Benjamin et al., Variants in ZFHX3 are associated with atrial fibrillation in individuals of European ancestry, Nat. Genet., 41 (8):879-81 (2009).
Bennett, Efficiency of antisense oligonucleotide drug discovery, Antisense Nucleic Acid Drug Dev., 12:215-24 (2002).

(Continued)

*Primary Examiner* — Stephen Kapushoc
(74) *Attorney, Agent, or Firm* — Marshall, Gerstein & Borun LLP

(57) ABSTRACT

The invention relates to procedures and methods of determining a susceptibility to cardiac arrhythmia, including Atrial Fibrillation, Atrial Flutter and Stroke, by assessing the presence or absence of alleles at polymorphic markers found to be associated with risk of these conditions. The invention further relates to kits encompassing reagents for assessing such markers, and diagnostic methods, uses and procedures for utilizing such susceptibility markers.

27 Claims, 1 Drawing Sheet

(56) References Cited

OTHER PUBLICATIONS

Berger et al., The glu298asp polymorphism in the nitric oxide synthase 3 gene is associated with the risk of ischemic stroke in two large independent case-control studies, Hum. Genet., 121 :169-78 (2007).
Berry et al., Positive and negative regulation of myogenic differentiation of C2C12 cells by isoforms of the multiple homeodomain zinc finger transcription factor ATBF1, J. Biol. Chem., 276:25057-65 (2001).
Bier et al., DNA microarrays, Adv. Biochem. Eng. Biotechnol., 109:433-53 (2008).
Bonita, Epidemiology of stroke, Lancet, 339(8789):342-4 (1992).
Bosher et al., RNA interference: genetic wand and genetic watchdog, Nat. Cell Biol., 2:E31-6 (2000).
Brass et al., The genetics of cerebrovascular disease, Baillieres Clin. Neurol., 4(2):221-45 (1995).
Brummelkamp et al., A system for stable expression of short interfering RNAs in mammalian cells, Science, 296:550-3 (2002).
Burgner et al., A genome-wide association study identifies novel and functionally related susceptibility Loci for Kawasaki disease, PLoS Genet., 5:e1000319 (2009).
Carter et al., Methods and strategies for analyzing copy number variation using DNA microarrays, Nat. Genet., 39:S16-21 (2007).
Chen et al., Clinical development of antisense oligonucleotides as anti-cancer therapeutics, Methods Mol. Med., 75:621-36 (2003).
Chen et al., Fluorescence polarization in homogeneous nucleic acid analysis, Genome Res., 9:492-8 (1999).
Chen et al., The evolution of gene regulation by transcription factors and microRNAs, Nat. Rev. Genet., 8:93-103 (2007).
Chi et al., Genomewide view of gene silencing by small interfering RNAs, Proc. Natl. Acad. Sci. USA, 100:6343-6 (2003).
Church et al., Genomic sequencing, Proc. Natl. Acad. Sci. USA, 81:1991-5 (1984).
Connolly et al., Clopidogrel plus aspirin versus oral anticoagulation for atrial fibrillation in the Atrial fibrillation Clopidogrel Trial with Irbesartan for prevention of Vascular Events (Active W): a randomised controlled trial, Lancet, 367(9526):1903-12 (2006).
Cotton et al., Reactivity of cytosine and thymine in single-base-pair mismatches with hydroxylamine and osmium tetroxide and its application to the study of mutations, Proc. Natl. Acad. Sci. USA, 85:4397-401 (1988).
Daly et al., High-resolution haplotype structure in the human genome, Nat. Genet., 29:229-32 (2001).
Dawson et al., A first-generation linkage disequilibrium map of human chromosome 22, Nature, 418:544-8 (2002).
Dempster et al., Manual likelihood from incomplete data via the EM algorithm, J. Royal Stat. Soc. B, 39:1-38 (1977).
Devlin et al., A comparison of linkage disequilibrium measures for fine-scale mapping, Genomics, 29:311-22 (1995).
Devlin et al., Genomic control for association studies, Biometrics, 55:997-1004 (1999).
Dias et al., Antisense oligonucleotides: basic concepts and mechanisms, Mol. Cancer Ther., 1:347-55 (2002).
Estivill et al., Copy number variants and common disorders: filling the gaps and exploring complexity in genome-wide association studies, PLoS Genet., 3:1787-99 (2007).
Falk et al., Haplotype relative risks: an easy reliable way to construct a proper control sample for risk calculations, Ann. Hum. Genet., 51:227-33 (1987).
Fan et al., Illumina universal bead arrays, Methods Enzymol., 410:57-73 (2006).
Fire et al., Potent and specific genetic interference by double-stranded RNA in *Caenorhabditis elegans*, Nature, 391:806-11 (1998).
Flavell et al., Analysis of the beta-delta-globin gene loci in normal and Hb Lepore DNA: direct determination of gene linkage and intergene distance, Cell, 15:25-41 (1978).
Frayling et al., Genome-wide association studies provide new insights into type 2 diabetes aetiology, Nat. Rev. Genet., 8:657-62 (2007).
Fuster et al., ACC/AHA/ESC Guidelines for the Management of Patients With Atrial Fibrillation: Executive Summary A Report of the American College of Cardiology/American Heart Association Task Force on Practice Guidelines and the European Society of Cardiology Committee for Practice Guidelines and Policy Conferences (Committee to Develop Guidelines for the Management of Patients With Atrial Fibrillation) Developed in Collaboration With the North American Society of Pacing and Electrophysiology, Circulation, 104(17):2118-50 (2001).
Gabriel et al., The structure of haplotype blocks in the human genome, Science, 296:2225-9 (2002).
Gage et al., Cost-effectiveness of preference-based antithrombotic therapy for patients with nonvalvular atrial fibrillation, Stroke, 29(6):1083-91 (1998).
Galfre et al., Antibodies to major histocompatibility antigens produced by hybrid cell lines, Nature, 266:550-2 (1977).
Geever et al., Direct identification of sickle cell anemia by blot hybridization, Proc. Natl. Acad. Sci. USA, 78:5081-5 (1981).
Go et al., Prevalence of diagnosed atrial fibrillation in adults: national implications for rhythm management and stroke prevention: the AnTicoagulation and Risk Factors in Atrial Fibrillation (ATRIA) Study, JAMA, 285(18):2370-5 (2001).
Grant et al., Variant of transcription factor 7-like 2 (TCF7L2) gene confers risk of type 2 diabetes, Nat. Genet., 38:320-3 (2006).
Gretarsdottir et al., Risk variants for atrial fibrillation on chromosome 4q25 associate with ischemic stroke, Ann. Neurol., 64:402-9 (2008).
Gretarsdottir et al., The gene encoding phosphodiesterase 4D confers risk of ischemic stroke, Nat. Genet, 35:131-8 (2003).
Gudbjartsson et al., A sequence variant ZFHX3 on 16q22 associates with atrial fibrillation and ischemic stroke, Nat. Genet., 41(8): 876-8 (2009).
Gudbjartsson et al., Variants conferring risk of atrial fibrillation on chromosome 4q25, Nature, 448:353-7 (2007).
Gudmundsson et al., Common sequence variants on 2p15 and Xp11.22 confer susceptibility to prostate cancer, Nat. Genet., 40:281-3 (2008).
Gudmundsson et al., Genome-wide association study identifies a second prostate cancer susceptibility variant at 8q24, Nat. Genet., 39:631-7 (2007).
Gunel et al., Mapping a gene causing cerebral cavernous malformation to 7q11.2-q21, Proc. Natl. Acad. Sci. USA, 92(14):6620-4 (1995).
Hassan et al., Genetics and ischaemic stroke, Brain, 123(Pt. 9):1784-812 (2000).
Helgadottir et al., A common variant on chromosome 9p21 affects the risk of myocardial infarction, Science, 316:1491-3 (2007).
Hill et al., Linkage disequilibrium in finite populations, Theor. Appl. Genet., 22:226-31 (1968).
Hoheisel, Microarray technology: beyond transcript profiling and genotype analysis, Nat. Rev. Genet., 7:200-10 (2006).
Hunter, Genetics: a touch of elegance with RNAi, Curr. Biol., 9:R440-2 (1999).
International Preliminary Report on Patentability for corresponding International application No. PCT/IS10/50001, date Oct. 4, 2011.
International Search Report and Written Opinion for corresponding International application No. PCT/IS2010/050001, mailing date Jun. 30, 2010.
Jeffreys et al., Intensely punctate meiotic recombination in the class II region of the major histocompatibility complex, Nat. Genet., 29:217-22 (2001).
Joutel et al., Notch3 mutations in CADASIL, a hereditary adult-onset condition causing stroke and dementia, Nature, 383(6602):707-10 (1996).
Karlin et al., Applications and statistics for multiple high-scoring segments in molecular sequences, Proc. Natl. Acad. Sci. USA, 90:5873-7 (1993).
Kent, BLAT—the BLAST-like alignment tool, Genome Res., 12:656-64 (2002).
Kim et al., Strategies for silencing human disease using RNA interference, Nat. Rev. Genet., 8:173-84 (2007).

(56) References Cited

OTHER PUBLICATIONS

Kim et al., Synthetic dsRNA Dicer substrates enhance RNAi potency and efficacy, Nat. Biotechnol., 23:222-6 (2005).
Kohler et al., Continuous cultures of fused cells secreting antibody of predefined specificity, Nature, 256:495-7 (1975).
Kozbor et al., The production of monoclonal antibodies from human lymphocytes, Immunol. Today, 4:72-9 (1983).
Kraus et al., Detection and isolation of novel protein-tyrosine kinase genes employing reduced stringency hybridization, Methods Enzymol., 200:546-56 (1991).
Kurreck, Antisense technologies. Improvement through novel chemical modifications, Eur. J. Biochem., 270:1628-44 (2003).
Kutyavin et al., A novel endonuclease IV post-PCR genotyping system, Nucleic Acids Res., 34:e128 (2006).
Lavery et al., Antisense and RNAi: powerful tools in drug target discovery and validation, Curr. Opin. Drug Discov. Devel., 6:561-9 (2003).
Lerner, How to make a hybridoma, Yale J. Biol. Med., 54:385-402 (1981).
Levy et al., Mutation of the Alzheimer's disease amyloid gene in hereditary cerebral hemorrhage, Dutch type, Science, 248(4959):1124-6 (1990).
Levy, Epidemiology and classification of atrial fibrillation, J. Cardiovasc. Electrophysiol., 9(8 Suppl):S78-82 (1998).
Lewontin et al., The Interaction of Selection and Linkage. I. General Considerations; Heterotic Models, Genetics, 49:49-67 (1964).
Lip et al., Antithrombotic treatment in atrial fibrillation, Heart, 92:155-61 (2006).
Lloyd-Jones et al., Lifetime risk for development of atrial fibrillation: the Framingham Heart Study, Circulation, 110:1042-6 (2004).
Maniatis et al., The first linkage disequilibrium (LD) maps: delineation of hot and cold blocks by diplotype analysis, Proc. Natl. Acad. Sci USA, 99:2228-33 (2002).
Mantel et al., Statistical aspects of the analysis of data from retrospective studies of disease, J. Natl. Cancer Inst., 22:719-48 (1959).
Marques et al., A structural basis for discriminating between self and nonself double-stranded RNAs in mammalian cells, Nat. Biotechnol., 24:559-65 (2006).
May et al., Crossover clustering and rapid decay of linkage disequilibrium in the Xp/Yp pseudoautosomal gene SHOX, Nat. Genet., 31:272-5 (2002).
McManus et al., Gene silencing in mammals by small interfering RNAs, Nat. Rev. Genet., 3:737-47 (2002).
Mockler et al., Applications of DNA tiling arrays for whole-genome analysis, Genomics, 85:1-15 (2005).
Morinaga et al., A human alpha-fetoprotein enhancer-binding protein, ATBF1, contains four homeodomains and seventeen zinc fingers, Mol. Cell Biol., 11:6041-9 (1991).
Myers et al., A fine-scale map of recombination rates and hotspots across the human genome, Science, 310:321-4 (2005).
Myers et al., Detection of single base substitutions by ribonuclease cleavage at mismatches in RNA:DNA duplexes, Science, 230:1242-6 (1985).
Myers et al., Optimal alignments in linear space, Cabios, 4:11-7 (1988).
Myers et al., The distribution and causes of meiotic recombination in the human genome, Biochem. Soc. Trans., 34:526-30 (2006).
Nicolae et al., Measuring the relative information in allele-sharing linkage studies, Biometrics, 60:368-75 (2004).
Nielsen et al., Peptide nucleic acid (PNA). A DNA mimic with a peptide backbone, Bioconjug. Chem., 5:3-7 (1994).
Nielsen et al., Sequence-selective recognition of DNA by strand displacement with a thymine-substituted polyamide, Science, 254:1497-500 (1991).
Nyren et al., Solid phase DNA minisequencing by an enzymatic luminometric inorganic pyrophosphate detection assay, Anal. Biochem., 208:171-5 (1993).
Olesen et al., Association of the 5-HT2A receptor gene polymorphism 102T/C with ischemic stroke, J. Mol. Neurosci., 30(3): 323-8 (2006).
Orita et al., Detection of polymorphisms of human DNA by gel electrophoresis as single-strand conformation polymorphisms, Proc. Natl. Acad. Sci. USA, 86:2766-70 (1989).
Palsdottir et al., Mutation in cystatin C gene causes hereditary brain haemorrhage, Lancet, 2(8611):603-4 (1988).
Patil et al., Blocks of limited haplotype diversity revealed by high-resolution scanning of human chromosome 21, Science, 294:1719-23 (2001).
Pearson et al., Improved tools for biological sequence comparison, Proc. Natl. Acad. Sci. USA, 85:2444-8 (1988).
Phillips et al., Chromosome-wide distribution of haplotype blocks and the role of recombination hot spots, Nat. Genet., 33:382-7 (2003).
Plasterk et al., The silence of the genes, Curr. Opin. Genet. Dev., 10:562-7 (2000).
Prystowsky, Management of atrial fibrillation: therapeutic options and clinical decisions, Am. J. Cardiol., 85(10A):3D-11D (2000).
Qi et al., Atbf1 is required for the Pit1 gene early activation, Proc. Natl. Acad. Sci. USA, 105:2481-6 (2008).
Ragoussis et al., Affymetrix GeneChip system: moving from research to the clinic, Expert Rev. Mol. Diagn., 6:145-52 (2006).
Redon et al., Global variation in copy number in the human genome, Nature, 444:444-54 (2006).
Reich et al., Linkage disequilibrium in the human genome, Nature, 411:199-204 (2001).
Reynolds et al., Rational siRNA design for RNA interference, Nat. Biotechnol., 22:326-30 (2004).
Risch et al., The future of genetic studies of complex human diseases, Science, 273:1516-7 (1996).
Risch et al., The relative power of family-based and case-control designs for linkage disequilibrium studies of complex human diseases I. DNA pooling, Genome Res., 8:1273-88 (1998).
Ronaghi et al., Analyses of secondary structures in DNA by pyrosequencing, Anal. Biochem., 267:65-71 (1999).
Ronaghi et al., PCR-introduced loop structure as primer in DNA sequencing, Biotechniques, 25:876-8, 880-2, 884 (1998).
Sacco et al., American Heart Association Prevention Conference. IV. Prevention and Rehabilitation of Stroke. Risk factors, Stroke, 28(7):1507-17 (1997).
Sahoo et al., Mutations in the gene encoding KRIT1, a Krev-1/rap1a binding protein, cause cerebral cavernous malformations (CCM1), Hum. Mol. Genet., 8(12): 2325-33 (1999).
Sanger et al., DNA sequencing with chain-terminating inhibitors, Proc. Natl. Acad. Sci. USA, 74:5463-7 (1977).
Sheffield et al., Attachment of a 40-base-pair G + C-rich sequence (GC-clamp) to genomic DNA fragments by the polymerase chain reaction results in improved detection of single-base changes, Proc. Natl. Acad. Sci. USA, 86:232-6 (1989).
Shi, Mammalian RNAi for the masses, Trends Genet., 19:9-12 (2003).
Shuey et al., RNAi: gene-silencing in therapeutic intervention, Drug Discov. Today, 7:1040-6 (2002).
Siolas et al., Synthetic shRNAs as potent RNAi triggers, Nat. Biotechnol., 23:227-31 (2005).
Smith et al., A high-density admixture map for disease gene discovery in african americans, Am. J. Hum. Genet., 74:1001-13 (2004).
Stacey et al., Common variants on chromosomes 2q35 and 16q12 confer susceptibility to estrogen receptor-positive breast cancer, Nat. Genet., 39:865-9 (2007).
Stefansson et al., A common inversion under selection in Europeans, Nat. Genet., 37:129-37 (2005).
Steinthorsdottir et al., A variant in CDKAL1 influences insulin response and risk of type 2 diabetes, Nat. Genet., 39:770-5 (2007).
Stephens et al., Antisense oligonucleotide therapy in cancer, Curr. Opin. Mol. Ther., 5:118-22 (2003).
Strausberg et al., Emerging DNA sequencing technologies for human genomic medicine, Drug Discov. Today, 13:569-77 (2008).
Stroke—1989. *Recommendations on stroke prevention, diagnosis, and therapy. Report of the WHO Task Force on Stroke and other Cerebrovascular Disorders*, Stroke, 20(10):1407-31 (1989).
Stumpf et al., Demography, recombination hotspot intensity, and the block structure of linkage disequilibrium, Curr. Biol., 13:1-8 (2003).

(56) References Cited

OTHER PUBLICATIONS

Styrkarsdottir et al., Multiple genetic loci for bone mineral density and fractures, N. Engl. J. Med., 358:2355-65 (2008).
Terwilliger et al., A haplotype-based 'haplotype relative risk' approach to detecting allelic associations, Hum. Hered., 42:337-46 (1992).
Thompson, Applications of antisense and siRNAs during preclinical drug development, Drug Discov. Today, 7:912-7 (2002).
Thorgeirsson et al., A variant associated with nicotine dependence, lung cancer and peripheral arterial disease, Nature, 452:638-42 (2008).
Torelli et al., ADVANCE and ADAM: two algorithms for the analysis of global similarity between homologous informational sequnces. CABIOS, 10:3-5 (1984).
Tournier-Lasserve et al., Cerebral autosomal dominant arteriopathy with subcortical infarcts and leukoencephalopathy maps to chromosome 19q12, Nat. Genet., 3(3):256-9 (1993).
Van Walraven et al., Oral anticoagulants vs aspirin in nonvalvular atrial fibrillation: an individual patient meta-analysis, JAMA, 288(19):2441-8 (2002).
Vickers et al., Efficient reduction of target RNAs by small interfering RNA and RNase H-dependent antisense agents. A comparative analysis, J. Biol. Chem., 278:7108-18 (2003).
Waldo, The interrelationship between atrial fibrillation and atrial flutter, Prog. Cardiovasc. Dis., 48(1):41-56 (2005).
Wall et al., Haplotype blocks and linkage disequilibrium in the human genome, Nat. Rev. Genet., 4:487-97 (2003).
Wang et al., Antisense anticancer oligonucleotide therapeutics, Curr. Cancer Drug Targets, 1:177-96 (2001).
Wang et al., Distribution of recombination crossovers and the origin of haplotype blocks: the interplay of population history, recombination, and mutation, Am. J. Hum. Genet., 71:1227-34 (2002).
Wichmann et al., KORA-gen—resource for population genetics, controls and a broad spectrum of disease phenotypes, Gesundheitswesen, 67 Suppl 1:S26-30 (2005).
Xia et al., siRNA-mediated gene silencing in vitro and in vivo, Nat. Biotechnol., 20:1006-10 (2002).
Yang et al., Development and validation of stroke risk equation for Hong Kong Chinese patients with type 2 diabetes: the Hong Kong Diabetes Registry, Diabetes Care, 30:65-70 (2007).
Zhang et al., A dynamic programming algorithm for haplotype block partitioning, Proc. Natl. Acad. Sci. USA, 99:7335-9 (2002).

\* cited by examiner

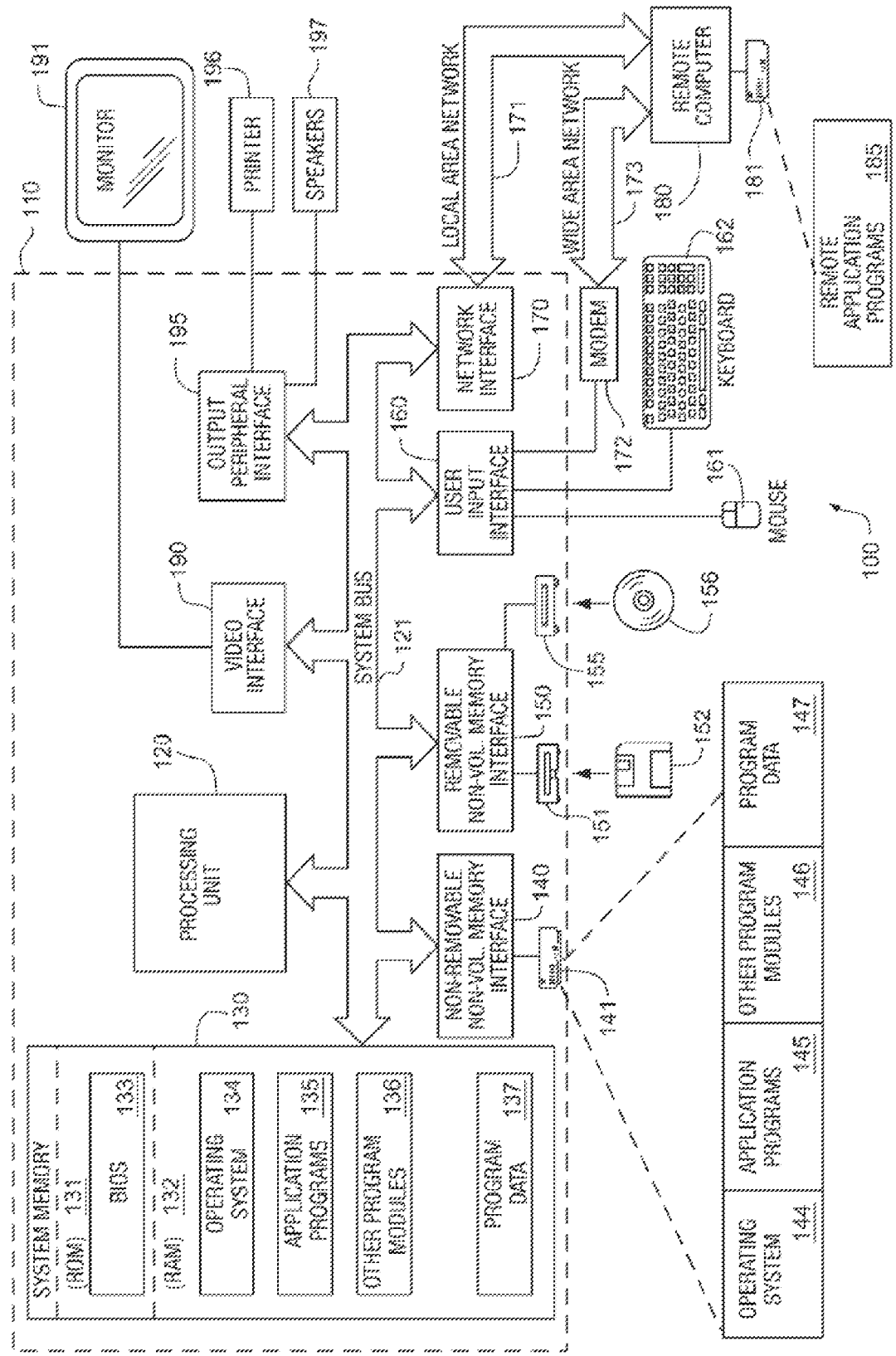

GENETIC MARKERS FOR RISK MANAGEMENT OF ATRIAL FIBRILLATION AND STROKE

CROSS-REFERENCE TO RELATED APPLICATIONS

This application is a U.S. National Phase of International Application No. PCT/IS2010/050001 filed Mar. 30, 2010, incorporated herein by reference, which claims priority benefit of Iceland Patent Application No. 8813 filed Apr. 3, 2009.

INTRODUCTION

Cardiac arrhythmia is a group of medical conditions, in which the electrical activity of the heart is irregular, or is slower or faster than normal. Some arrhythmias are life-threatening, and can cause cardiac arrest or sudden death. Others cause, or predispose to, other aggravating symptoms or disease, including stroke. Fibrillation is a serious form of arrhythmia, in which the heart muscle presents with irregular or quivering motion due to lack of unity in the function of contractile cells. Fibrillation can affect the atrium (Atrial Fibrillation (AF) or Atrial Flutter (AFI)), or the ventricle (Ventricular Fibrillation (VF)).

Atrial fibrillation (AF) is an abnormal heart rhythm (cardiac arrhythmia) which involves the two small, upper heart chambers (the atria). Heart beats in a normal heart begin after electricity generated in the atria by the sinoatrial node spreads through the heart and causes contraction of the heart muscle and pumping of blood. In AF, the regular electrical impulses of the sinoatrial node are replaced by disorganized, rapid electrical impulses which result in irregular heart beat.

Atrial fibrillation is the most common cardiac arrhythmia. The risk of developing atrial fibrillation increases with age—AF affects four percent of individuals in their 80s. An individual may spontaneously alternate between AF and a normal rhythm (paroxysmal atrial fibrillation) or may continue with AF as the dominant cardiac rhythm without reversion to the normal rhythm (chronic atrial fibrillation). Atrial fibrillation is often asymptomatic, but may result in symptoms of palpitations, fainting, chest pain, or even heart failure. These symptoms are especially common when atrial fibrillation results in a heart rate which is either too fast or too slow. In addition, the erratic motion of the atria leads to blood stagnation (stasis) which increases the risk of blood clots that may travel from the heart to the brain and other areas. Thus, AF is an important risk factor for stroke, the most feared complication of atrial fibrillation.

The symptoms of atrial fibrillation may be treated with medications which slow the heart rate. Several medications as well as electrical cardioversion may be used to convert AF to a normal heart rhythm. Surgical and catheter-based therapies may also be used to prevent atrial fibrillation in certain individuals. People with AF are often given blood thinners such as warfarin to protect them from strokes.

Any patient with 2 or more identified episodes of atrial fibrillation is said to have recurrent atrial fibrillation. This is further classified into paroxysmal and persistent based on when the episode terminates without therapy. Atrial fibrillation is said to be paroxysmal when it terminates spontaneously within 7 days, most commonly within 24 hours. Persistent or chronic atrial fibrillation is AF established for more than seven days. Differentiation of paroxysmal from chronic or established AF is based on the history of recurrent episodes and the duration of the current episode of AF (Levy S., *J Cardiovasc Electrophysiol.* 8 Suppl, S78-82 (1998)).

Lone atrial fibrillation (LAF) is defined as atrial fibrillation in the absence of clinical or echocardiographic findings of cardiopulmonary disease.

Atrial fibrillation is usually accompanied by symptoms related to either the rapid heart rate or embolization. Rapid and irregular heart rates may be perceived as palpitations, exercise intolerance, and occasionally produce angina and congestive symptoms of shortness of breath or edema. Sometimes the arrhythmia will be identified with the onset of a stroke or a transient ischemic attack (TIA). It is not uncommon to identify atrial fibrillation on a routine physical examination or electrocardiogram (ECG/EKG), as it may be asymptomatic in some cases. Paroxysmal atrial fibrillation is the episodic occurrence of the arrhythmia and may be difficult to diagnose. Episodes may occur with sleep or with exercise, and their episodic nature may require prolonged ECG monitoring (e.g. a Holter monitor) for diagnosis.

Atrial fibrillation is diagnosed on an electrocardiogram, an investigation performed routinely whenever irregular heart beat is suspected. Characteristic findings include absence of P waves, unorganized electrical activity in their place and irregularity of R-R interval due to irregular conduction of impulses to the ventricles. If paroxysmal AF is suspected, episodes may be documented with the use of Holter monitoring (continuous ECG recording for 24 hours or longer).

While many cases of AF have no definite cause, it may be the result of various other problems (see below). Hence, renal function and electrolytes are routinely determined, as well as thyroid-stimulating hormone and a blood count. A chest X-ray is generally performed. In acute-onset AF associated with chest pain, cardiac troponins or other markers of damage to the heart muscle may be ordered. Coagulation studies (INR/aPTT) are usually performed, as anticoagulant medication may be commenced. A transesophageal echocardiogram may be indicated to identify any intracardiac thrombus (Fuster V., et al., Circulation; 104, 2118-2150 (2001)).

Atrial Flutter (AFI) is characterized by an abnormal fast heart rhythm in the atria. Patients who present with atrial flutter commonly also experience Atrial Fibrillation and vice versa (Waldo, A., *Progr Cardiovasc Disease,* 48:41-56 (2005)). Mechanistically and biologically, AF and AFI are thus likely to be highly related.

AF (and AFI) is linked to several cardiac causes, but may occur in otherwise normal hearts. Known associations include: High blood pressure, Mitral stenosis (e.g. due to rheumatic heart disease or mitral valve prolapse), Mitral regurgitation, Heart surgery, Coronary artery disease, Hypertrophic cardiomyopathy, Excessive alcohol consumption ("binge drinking" or "holiday heart"), Hyperthyroidism, Hyperstimulation of the vagus nerve, usually by having large meals ("binge eating"), Lung pathology (such as pneumonia, lung cancer, pulmonary embolism, Sarcoidosis), Pericarditis, Intense emotional turmoil, and Congenital heart disease.

The normal electrical conduction system of the heart allows the impulse that is generated by the sinoatrial node (SA node) of the heart to be propagated to and stimulate the myocardium (muscle of the heart). When the myocardium is stimulated, it contracts. It is the ordered stimulation of the myocardium that allows efficient contraction of the heart, thereby allowing blood to be pumped to the body. In atrial fibrillation, the regular impulses produced by the sinus node to provide rhythmic contraction of the heart are overwhelmed by the rapid randomly generated discharges produced by larger areas of atrial tissue. An organized electrical impulse in the atrium produces atrial contraction; the lack of such an impulse, as in atrial fibrillation, produces stagnant blood flow, especially in the atrial appendage and predisposes to clotting.

The dislodgement of a clot from the atrium results in an embolus, and the damage produced is related to where the circulation takes it. An embolus to the brain produces the most feared complication of atrial fibrillation, stroke, while an embolus may also lodge in the mesenteric circulation (the circulation supplying the abdominal organs) or digit, producing organ-specific damage.

Treatment of atrial fibrillation is directed by two main objectives: (i) prevent temporary circulatory instability; (ii) prevent stroke. The most common methods for achieving the former includes rate and rhythm control, while anticoagulation is usually the desired method for the latter (Prystowsky E. N., *Am J Cardiol;* 85, 3D-11D (2000); van Walraven C, et al., *Jama.* 288, 2441-2448 (2002)). Common methods for rate control, i.e. for reducing heart rate to normal, include beta blockers (e.g., metotprolol), cardiac glycosides (e.g., digoxin) and calcium channel blockers (e.g., verapamil). All these medications work by slowing down the generation of pulses from the atria, and the conduction from the atria to the ventricles. Other drugs commonly used include quinidine, flecamide, propafenone, disopyramide, sotalol and amiodarone. Rhythm control can be achieved by electrical cardioversion, i.e. by applying DC electrical shock, or by chemical cardioversion, using drugs such as amiodarone, propafenone and flecamide.

Preventive measures for stroke include anticoagulants. Representative examples of anticoagulant agents are Dalteparin (e.g., Fragmin), Danaparoid (e.g., Orgaran), Enoxaparin (e.g., Lovenox), Heparin (various), Tinzaparin (e.g., Innohep), Warfarin (e.g., Coumadin). Some patients with lone atrial fibrillation are sometimes treated with aspirin or clopidogrel. There is evidence that aspirin and clopidogrel are effective when used together, but the combination is still inferior to warfarin (Connolly S., et al. *Lancet;* 367, 1903-1912 (2006)). (2) The new anticoagulant ximelagatran has been shown to prevent stroke with equal efficacy as warfarin, without the difficult monitoring process associated with warfarin and with possibly fewer adverse haemorrhagic events. Unfortunately, ximegalatran and other similar anticoagulant drugs (commonly referred to as direct thrombin inhibitors), have yet to be widely licensed.

Determining who should and should not receive anti-coagulation with warfarin is not straightforward. The CHADS2 score is the best validated method of determining risk of stroke (and therefore who should be anticoagulated). The UK NICE guidelines have instead opted for an algorithm approach. The underlying problem is that if a patient has a yearly risk of stroke that is less than 2%, then the risks associated with taking warfarin outweigh the risk of getting a stroke (Gage B. F. et al. *Stroke* 29, 1083-1091 (1998))

Atrial fibrillation can sometimes be controlled with treatment. The natural tendency of atrial fibrillation, however, is to become a chronic condition. Chronic AF leads to an increased risk of death. Patients with atrial fibrillation are at significantly increased chance of stroke.

Atrial fibrillation is common among older adults. In developed countries, the number of patients with atrial fibrillation is likely to increase during the next 50 years, due to the growing proportion of elderly individuals (Go A. S. et al., *Jama.,* 285, 2370-2375 (2001))(3). In the Framingham study the lifetime risk for development of AF is 1 in 4 for men and women 40 years of age and older. Lifetime risks for AF are high (1 in 6). According to data from the National Hospital Discharge Survey (1996-2001) on cases that included AF as a primary discharge diagnosis found that 45% of the patients are male, and that the mean age for men was 66.8 years and 74.6 for women. The racial breakdown for admissions was found to be 71.2% white, 5.6% black, 2% other races, and 20% not specified. Furthermore, African American patients were, on average, much younger than other races. The incidence in men ranged from 20.58/100,000 persons per year for patients ages 15-44 years to 1203/100,000 persons per years for those ages 85 and older. From 1996-2001, hospitalizations with AF as the first listed diagnosis, increased by 34%.

Stroke is a common and serious disease. Each year in the United States more than 600,000 individuals suffer a stroke and more than 160,000 die from stroke-related causes (Sacco, R. L. et al., *Stroke* 28, 1507-17 (1997)). Furthermore, over 300,000 individuals present with Transient Ischemic Attack, a mild form of stroke, every year in the US. In western countries stroke is the leading cause of severe disability and the third leading cause of death (Bonita, R., *Lancet* 339, 342-4 (1992)). The lifetime risk of those who reach the age of 40 exceeds 10%.

The clinical phenotype of stroke is complex but is broadly divided into ischemic (accounting for 80-90%) and hemorrhagic stroke (10-20%) (Caplan, L. R. *Caplan's Stroke: A Clinical Approach,* 1-556 (Butterworth-Heinemann, 2000)). Ischemic stroke is further subdivided into large vessel occlusive disease (referred to here as carotid stroke), usually due to atherosclerotic involvement of the common and internal carotid arteries, small vessel occlusive disease, thought to be a non-atherosclerotic narrowing of small end-arteries within the brain, and cardiogenic stroke due to blood clots arising from the heart usually on the background of atrial fibrillation or ischemic (atherosclerotic) heart disease (Adams, H. P., Jr. et al., *Stroke* 24, 35-41 (1993)). Therefore, it appears that stroke is not one disease but a heterogeneous group of disorders reflecting differences in the pathogenic mechanisms (Alberts, M. J. *Genetics of Cerebrovascular Disease,* 386 (Futura Publishing Company, Inc., New York, 1999); Hassan, A. & Markus, H. S. *Brain* 123, 1784-812 (2000)). However, all forms of stroke share risk factors such as hypertension, diabetes, hyperlipidemia, and smoking (Sacco, R. L. et al., *Stroke* 28, 1507-17 (1997); Leys, D. et al., *J. Neurol.* 249, 507-17 (2002)). Family history of stroke is also an independent risk factor suggesting the existence of genetic factors that may interact with environmental factors (Hassan, A. & Markus, H. S. *Brain* 123, 1784-812 (2000); Brass, L. M. & Alberts, M. J. *Baillieres Clin. Neurol.* 4, 221-45 (1995)).

The genetic determinants of the common forms of stroke are still largely unknown. There are examples of mutations in specific genes that cause rare Mendelian forms of stroke such as the Notch3 gene in CADASIL (cerebral autosomal dominant arteriopathy with subcortical infarctions and leukoencephalopathy) (Tournier-Lasserve, E. et al., *Nat. Genet.* 3, 256-9 (1993); Joutel, A. et al., *Nature* 383, 707-10 (1996)), Cystatin C in the Icelandic type of hereditary cerebral hemorrhage with amyloidosis (Palsdottir, A. et al., *Lancet* 2, 603-4 (1988)), APP in the Dutch type of hereditary cerebral hemorrhage (Levy, E. et al., *Science* 248, 1124-6 (1990)) and the KRIT1 gene in patients with hereditary cavernous angioma (Gunel, M. et al., *Proc. Natl. Acad. Sci. USA* 92, 6620-4 (1995); Sahoo, T. et al., *Hum. Mol. Genet.* 8, 2325-33 (1999)). None of these rare forms of stroke occur on the background of atherosclerosis, and therefore, the corresponding genes are not likely to play roles in the common forms of stroke which most often occur with atherosclerosis.

It is very important for the health care system to develop strategies to prevent stroke. Once a stroke happens, irreversible cell death occurs in a significant portion of the brain supplied by the blood vessel affected by the stroke. Unfortunately, the neurons that die cannot be revived or replaced from a stem cell population. Therefore, there is a need to prevent strokes from happening in the first place. Although we already know of certain clinical risk factors that increase stroke risk (listed above), there is an unmet medical need to define the genetic factors involved in stroke to more precisely define stroke risk. Further, if predisposing alleles are common in the general population and the specificity of predicting a disease based on their presence is low, additional loci such as protective loci are needed for meaningful prediction of disposition of the disease state. There is also a great need for therapeutic agents for preventing the first stroke or further strokes in individuals who have suffered a previous stroke or transient ischemic attack.

AF is an independent risk factor for stroke, increasing risk about 5-fold. The risk for stroke attributable to AF increases with age. AF is responsible for about 15-20% of all strokes. AF is also an independent risk factor for stroke recurrence and stroke severity. A recent report showed people who had AF and were not treated with anticoagulants had a 2.1-fold increase in risk for recurrent stroke and a 2.4 fold increase in risk for recurrent severe stroke. People who have stroke caused by AF have been reported as 2.23 times more likely to be bedridden compared to those who have strokes from other causes.

There is a need for an understanding of the susceptibility factors leading to increased predisposition for AF and stroke. Identification of at-risk variants for AF can, for example, be useful for assessing which individuals are at particularly high risk for AF and subsequent stroke. Furthermore, preventive treatment can be administered to individuals suffering from AF and who are carriers of at-risk susceptibility variants for AF and/or stroke. Finally, identification of at-risk variants for AF and/or stroke can lead to the identification of new targets for drug therapy, as well as the development of novel therapeutic measures.

SUMMARY OF THE INVENTION

As described herein, certain polymorphic markers have been shown to be associated with risk of Atrial Fibrillation, Atrial Flutter and Stroke. Such markers are useful in a number of diagnostic applications, as described further herein. The markers can also be used in certain aspects that relate to development of markers for diagnostic use, systems and apparati for diagnostic use, as well as in methods that include selection of individuals based on their genetic status with respect to such variants. These and other aspects of the invention are described in more detail herein.

In one aspect the invention relates to a method of determining a susceptibility to a condition selected from the group consisting of: a cardiac arrhythmia selected from Atrial Fibrillation and Atrial Flutter, and Stroke, the method comprising obtaining sequence data about a human individual identifying at least one allele of at least one polymorphic marker, wherein different alleles of the at least one polymorphic marker are associated with different susceptibilities to the condition in humans, and determining a susceptibility to the condition from the sequence data, wherein the at least one polymorphic marker is selected from the group consisting of rs7193343, rs10077199, rs10490066, rs10516002, rs10519674, rs1394796, rs2935888, rs4560443, rs6010770 and rs7733337, and markers in linkage disequilibrium therewith.

As described in further detail herein, polymorphic markers can comprise variations comprising one or more nucleotides at the nucleotide level. Sequence data indicative of particular polymorphisms, in particular with respect to specific alleles of a polymorphism, is thus indicative of the nucleotides that are present at the specific polymorphic site(s) that characterize the polymorphism. For polymorphisms that comprise a single nucleotide, (so called single nucleotide polymorphisms (SNPs)), the sequence data thus includes at least sequence for the single nucleotide characteristic of the polymorphism.

The invention in another aspect relates to a method for determining a susceptibility to a condition selected from the group consisting of cardiac arrhythmia selected from Atrial Fibrillation and Atrial Flutter, and Stroke, in a human individual, comprising determining the presence or absence of at least one allele of at least one polymorphic marker in a nucleic acid sample obtained from the individual, or in a genotype dataset from the individual, wherein the at least one polymorphic marker is selected from the group consisting of rs7193343, rs10077199, rs10490066, rs10516002, rs10519674, rs1394796, rs2935888, rs4560443, rs6010770 and rs7733337, and markers in linkage disequilibrium therewith, and wherein determination of the presence of the at least one allele is indicative of a susceptibility to the condition.

The invention further relates to a method of assessing a susceptibility to a condition selected from the group consisting of: a cardiac arrhythmia selected from atrial fibriallation and atrial flutter, and stroke, in a human individual, comprising (i) obtaining sequence information about the individual for at least one polymorphic marker in SEQ ID NO:1, wherein different alleles of the at least one polymorphic marker are associated with different susceptibilities to the condition in humans; (ii). identifying the presence or absence of at least one allele in the at least one polymorphic marker that correlates with increased occurrence of the condition in humans; wherein determination of the presence of the at least one allele identifies the individual as having elevated susceptibility to the condition, and wherein determination of the absence of the at least one allele identifies the individual as not having the elevated susceptibility.

The invention also provides a method of determining a susceptibility to a condition selected from the group consisting of: a cardiac arrhythmia selected from Atrial Fibrillation and Atrial Flutter, and Stroke, the method comprising obtaining sequence data about a human individual identifying at least one allele of at least one polymorphic marker, wherein different alleles of the at least one polymorphic marker are associated with different susceptibilities to the condition in humans, and determining a susceptibility to the condition from the sequence data, wherein the at least one polymorphic marker is a marker associated with the human ZFHX3 gene.

The invention also relates to a method of screening a candidate marker for assessing susceptibility to a condition selected from the group consisting of a cardiac arrhythmia selected from Atrial Fibrillation and Atrial Flutter, and Stroke, comprising analyzing the frequency of at least one allele of a polymorphic marker selected from the group consisting of rs7193343, rs10077199, rs10490066, rs10516002, rs10519674, rs1394796, rs2935888, rs4560443, rs6010770 and rs7733337, and markers in linkage disequilibrium therewith, in a population of human individuals diagnosed with the condition, wherein a significant difference in frequency of the at least one allele in the population of human individuals diagnosed with the condition as compared to the frequency of the at least one allele in a control population of human individuals is indicative of the marker being useful as a susceptibility marker for the condition.

Another aspect of the invention relates to a method of identification of a marker for use in assessing susceptibility to a condition selected from the group consisting of: a cardiac arrhythmia selected from Atrial Fibrillation and Atrial Flutter, and Stroke, in human individuals, the method comprising: (1) identifying at least one polymorphic marker within SEQ ID NO:1, or at least one polymorphic marker in linkage disequilibrium with at least one marker within SEQ ID NO:1; (2) obtaining sequence information about the at least one polymorphic marker in a group of individuals diagnosed with the condition; and (3) obtaining sequence information about the at least one polymorphic marker in a group of control individuals; wherein determination of a significant difference in frequency of at least one allele in the at least one polymorphism in individuals diagnosed with the condition as compared with the frequency of the at least one allele in the control group is indicative of the at least one polymorphism being useful for assessing susceptibility to the condition.

The invention furthermore relates to a method of predicting prognosis of an individual diagnosed with a condition selected from the group consisting of: a cardiac arrhythmia selected from Atrial Fibrillation and Atrial Flutter, and Stroke, the method comprising obtaining sequence data about a human individual identifying at least one allele of at least one polymorphic marker selected from the group consisting of rs7193343, rs10077199, rs10490066, rs10516002, rs10519674, rs1394796, rs2935888, rs4560443, rs6010770 and rs7733337, and markers in linkage disequilibrium therewith, wherein different alleles of the at least one polymorphic marker are associated with different susceptibilities to the conditions in humans, and predicting prognosis of the condition from the sequence data.

The invention in a further aspect relates to a method of assessing probability of response of a human individual to a therapeutic agent for preventing, treating and/or ameliorating symptoms associated with a condition selected from the group consisting of: a cardiac arrhythmia selected from Atrial Fibriallation and Atrial Flutter, and Stroke, comprising obtaining sequence data about a human individual identifying at least one allele of at least one polymorphic marker selected from the group consisting of rs7193343, rs10077199, rs10490066, rs10516002, rs10519674, rs1394796, rs2935888, rs4560443, rs6010770 and rs7733337, and markers in linkage disequilibrium therewith, wherein different alleles of the at least one polymorphic marker are associated with different probabilities of response to the therapeutic agent in humans, and determining the probability of a positive response to the therapeutic agent from the sequence data.

The invention also provides kits useful in the diagnostic applications described herein. Accordingly, in one aspect, the invention relates to a kit for assessing susceptibility to a condition selected from the group consisting of: a cardiac arrhythmia selected from Atrial Fibrillation and Atrial Flutter, and Stroke, the kit comprising reagents for selectively detecting at least one allele of at least one polymorphic marker in the genome of the individual, wherein the polymorphic marker is selected from the group consisting of rs7193343, rs10077199, rs10490066, rs10516002, rs10519674, rs1394796, rs2935888, rs4560443, rs6010770 and rs7733337, and markers in linkage disequilibrium therewith, and a collection of data comprising correlation data between the at least one polymorphism and susceptibility to the condition.

The invention further provides use of an oligonucleotide probe in the manufacture of a diagnostic reagent for diagnosing and/or assessing a susceptibility to a condition selected from the group consisting of: a cardiac arrhythmia selected from Atrial Fibrillation and Atrial Flutter, and Stroke, wherein the probe is capable of hybridizing to a segment of a nucleic acid whose nucleotide sequence is given by SEQ ID NO:1, and wherein the segment is 15-500 nucleotides in length.

Computer-implemented aspects of the invention include computer-readable media and computer systems and apparati. One aspect relates to a computer-readable medium having computer executable instructions for determining susceptibility to a condition selected from the group consisting of: a cardiac arrhythmia selected from Atrial Fibrillation and Atrial Flutter, and Stroke, the computer readable medium comprising (1) data indicative of at least one polymorphic marker; and (2) a routine stored on the computer readable medium and adapted to be executed by a processor to determine risk of developing the condition for the at least one polymorphic marker; wherein the at least one polymorphic marker is selected from the group consisting of rs7193343, rs10077199, rs10490066, rs10516002, rs10519674, rs1394796, rs2935888, rs4560443, rs6010770 and rs7733337, and markers in linkage disequilibrium therewith.

Another computer-implemented aspect relates to an apparatus for determining a genetic indicator for a condition selected from the group consisting of: a cardiac arrhythmia selected from Atrial Fibrillation and Atrial Flutter, and Stroke, in a human individual, comprising a processor; and a computer readable memory having computer executable instructions adapted to be executed on the processor to analyze marker and/or haplotype information for at least one human individual with respect to at least one polymorphic marker selected from the group consisting of rs7193343, rs10077199, rs10490066, rs10516002, rs10519674, rs1394796, rs2935888, rs4560443, rs6010770 and rs7733337, and markers in linkage disequilibrium therewith, and generate an output based on the marker or haplotype information, wherein the output comprises a measure of susceptibility of the at least one marker or haplotype as a genetic indicator of the condition for the human individual.

These and other aspects of the invention will be described in detail in the following. Particular embodiments will be described, in particular as they relate to the selection and use of polymorphic variants and haplotypes. It should be understood that all combinations of features described herein in the following are contemplated, even if the combination of feature is not specifically found in the same sentence or paragraph herein. This includes in particular the use of all markers disclosed herein, alone or in combination, for analysis individually or in haplotypes, in all aspects of the invention as described herein.

The procedures, uses, or methods of the invention in some embodiments further comprise a step of administering to an individual determined to be at increased risk for developing cardiac arrhythmia or stroke a composition comprising at least one therapeutic agent effective to treat or prevent cardiac arrhythmia or stroke, or prevent symptoms associated with cardiac arrhythmia or stroke. Thus, the invention can be used to determine whether an individual is suitable for a particular treatment module.

It should be understood that all combinations of features described herein are contemplated, even if the combination of feature is not specifically found in the same sentence or paragraph herein. This includes in particular the use of all markers disclosed herein, alone or in combination, for analysis individually or in haplotypes, in all aspects of the invention as described herein.

BRIEF DESCRIPTION OF THE DRAWINGS

The foregoing and other objects, features and advantages of the invention will be apparent from the following more particular description of preferred embodiments of the invention.

FIG. 1 provides a diagram illustrating a computer-implemented system utilizing risk variants as described herein.

DETAILED DESCRIPTION

Definitions

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometime referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including SNPs, mini- or microsatellites, translocations and copy number variations (insertions, deletions, duplications). Polymorphic markers can be of any measurable frequency in the population. For mapping of disease genes, polymorphic markers with population frequency higher than 5-10% are in general most useful. However, polymorphic markers may also have lower population frequencies, such as 1-5% frequency, or even lower frequency, in particular copy number variations (CNVs). The term shall, in the present context, be taken to include polymorphic markers with any population frequency.

An "allele" refers to the nucleotide sequence of a given locus (position) on a chromosome. A polymorphic marker allele thus refers to the composition (i.e., sequence) of the marker on a chromosome. Genomic DNA from an individual contains two alleles (e.g., allele-specific sequences) for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

Sequence conucleotide ambiguity as described herein is as proposed by IUPAC-IUB. These codes are compatible with the codes used by the EMBL, GenBank, and PIR databases.

| IUB code | Meaning |
| --- | --- |
| A | Adenosine |
| C | Cytidine |
| G | Guanine |
| T | Thymidine |
| R | G or A |

-continued

| IUB code | Meaning |
| --- | --- |
| Y | T or C |
| K | G or T |
| M | A or C |
| S | G or C |
| W | A or T |
| B | C, G or T |
| D | A, G or T |
| H | A, C or T |
| V | A, C or G |
| N | A, C, G or T (Any base) |

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population. An "indel" is a common form of polymorphism comprising a small insertion or deletion that is typically only a few nucleotides long.

A "haplotype," as described herein, refers to a segment of genomic DNA that is characterized by a specific combination of alleles arranged along the segment. For diploid organisms such as humans, a haplotype comprises one member of the pair of alleles for each polymorphic marker or locus along the segment. In a certain embodiment, the haplotype can comprise two or more alleles, three or more alleles, four or more alleles, or five or more alleles. Haplotypes are described herein in the context of the marker name and the allele of the marker in that haplotype, e.g., "4 rs7193343" refers to the 4 allele of marker rs7193343 being in the haplotype, and is equivalent to "rs7193343 allele 4". Furthermore, allelic codes in haplotypes are as for individual markers, i.e. 1=A, 2=C, 3=G and 4=T.

The term "susceptibility", as described herein, refers to the proneness of an individual towards the development of a certain state (e.g., a certain trait, phenotype or disease), or towards being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of atrial fibrillation and/or stroke, as characterized by a relative risk (RR) or odds ratio (OR) of greater than one for the particular allele or haplotype. Alternatively, the markers and/or haplotypes of the invention are characteristic of decreased susceptibility (i.e., decreased risk) of atrial fibrillation and/or stroke, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or they can contain information about multiple markers, and they may also comprise other factors, such as particulars about diseases diagnoses, racial information, biomarkers, biochemical measurements, therapeutic methods or drugs, etc.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" as described herein, refers to a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including a blood sample, sample of amniotic fluid, sample of cerebrospinal fluid, or tissue sample from skin, muscle, buccal or conjunctival mucosa, placenta, gastrointestinal tract or other organs.

The term "atrial fibrillation therapeutic agent" refers to an agent that can be used to ameliorate or prevent symptoms associated with atrial fibrillation. Similarly the term "stroke therapeutic agent" refers to an agent that can be used to ameliorate or prevent symptoms associated with stroke, including ischemic stroke.

The term "atrial fibrillation-associated nucleic acid", as described herein, refers to a nucleic acid that has been found to be associated to atrial fibrillation and/or stroke. This includes, but is not limited to, the markers and haplotypes described herein and markers and haplotypes in strong linkage disequilibrium (LD) therewith. In one embodiment, an atrial fibrillation-associated nucleic acid refers to an LD-block found to be associated with atrial fibrillation through at least one polymorphic marker located within the LD block.

The term "antisense agent" or "antisense oligonucleotide" refers, as described herein, to molecules, or compositions comprising molecules, which include a sequence of purine an pyrimidine heterocyclic bases, supported by a backbone, which are effective to hydrogen bond to a corresponding contiguous bases in a target nucleic acid sequence. The backbone is composed of subunit backbone moieties supporting the purine an pyrimidine heterocyclic bases at positions which allow such hydrogen bonding. These backbone moieties are cyclic moieties of 5 to 7 atoms in size, linked together by phosphorous-containing linkage units of one to three atoms in length. In certain preferred embodiments, the antisense agent comprises an oligonucleotide molecule.

The term "ZFHX3", in the present context, refers to the zinc finger homeobox 3 gene on chromosome 16q22. This gene is sometimes also called AT motif-binding factor 1 (ATBF1).

The term "LD Block C16", as described herein, refers to the Linkage Disequilibrium (LD) block on Chromosome 16 between markers rs16971447 and rs9940321, corresponding to positions 71,565,471-71,631,309 of NCBI (National Center for Biotechnology Information) Build 36 (SEQ ID NO:1).

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNPsite; the original allele and the mutated allele. Due to natural genetic drift and possibly also selective pressure, the original mutation has resulted in a polymorphism characterized by a particular frequency of its alleles in any given population. Many other types of sequence variants are found in the human genome, including mini- and microsatellites, and insertions, deletions and inversions (also called copy number variations (CNVs)). A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

Due to their abundance, SNPs account for a majority of sequence variation in the human genome. Over 6 million SNPs have been validated to date (http://www.ncbi.nlm.nih.gov/projects/SNP/snp_summary.cgi). However, CNVs are receiving increased attention. These large-scale polymorphisms (typically 1 kb or larger) account for polymorphic variation affecting a substantial proportion of the assembled human genome; known CNVs covery over 15% of the human genome sequence (Estivill, X Armengol; L., *PloS Genetics* 3:1787-99 (2007). A http://projects.tcag.ca/variation/). Most of these polymorphisms are however very rare, and on average affect only a fraction of the genomic sequence of each individual. CNVs are known to affect gene expression, phenotypic variation and adaptation by disrupting gene dosage, and are also known to cause disease (microdeletion and microduplication disorders) and confer risk of common complex diseases, including HIV-1 infection and glomerulonephritis (Redon, R., et al. *Nature* 23:444-454 (2006)). It is thus possible that either previously described or unknown CNVs represent causative variants in linkage disequilibrium with the markers described herein to be associated with Atrial Fibrillation, Atrial Flutter and Stroke. Methods for detecting CNVs include comparative genomic hybridization (CGH) and genotyping, including use of genotyping arrays, as described by Carter (*Nature Genetics* 39:S16-S21 (2007)). The Database of Genomic Variants (http://projects.tcag.ca/variation/) contains updated information about the location, type and size of described CNVs. The database currently contains data for over 15,000 CNVs.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, i.e. A and G. Alternatively, by designing an assay that is designed to detect the complimentary strand on the DNA template, the presence of the complementary bases T and C can be measured. Quantitatively (for example, in terms of risk estimates), identical results would be obtained from measurement of either DNA strand (+ strand or − strand).

Polymorphic markers (variants) can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (e.g., Chen, X. et al., *Genome Res.* 9(5): 492-98 (1999); Kutyavin et al., *Nucleic Acid Res.* 34:e128 (2006)), utilizing PCR, LCR, Nested PCR and other techniques for nucleic acid amplification. Specific commercial methodologies available for SNP genotyping include, but are not limited to, TaqMan genotyping assays and SNPlex platforms (Applied Biosystems), gel electrophoresis (Applied Biosystems), mass spectrometry (e.g., MassARRAY system from Sequenom), minisequencing methods, real-time PCR, Bio-Plex system (BioRad), CEQ and SNPstream systems (Beckman), array hybridization technology (e.g., Affymetrix GeneChip; Perlegen), BeadArray Technologies (e.g., Illumina GoldenGate and Infinium assays), array tag technology (e.g., Parallele), and endonuclease-based fluorescence hybridization technology (Invader; Third Wave). Some of the available array platforms, including Affymetrix SNP Array 6.0 and Illumina CNV370-Duo and 1M BeadChips, include SNPs that tag certain CNVs. This allows detection of CNVs via surrogate SNPs included in these platforms. Thus, by use of these or other methods available to the person skilled in the art, one or more alleles at polymorphic markers, including microsatellites, SNPs or other types of polymorphic markers, can be identified.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet.* 29:217-222 (2001); May, C. A., et al., *Nature Genet.* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.50 (50%) and another element occurs at a frequency of 0.50 (50%), then the predicted occurrance of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurence of each allele or haplotype in the population. For populations of diploids, e.g., human populations, individuals will typically have two alleles or allelic combinations for each genetic element (e.g., a marker, haplotype or gene).

Many different measures have been proposed for assessing the strength of linkage disequilibrium (LD; reviewed in Devlin, B. & Risch, N., *Genomics* 29:311-22 (1995))). Most capture the strength of association between pairs of biallelic sites. Two important pairwise measures of LD are $r^2$ (sometimes denoted $\Delta^2$) and |D'| (Lewontin, R., *Genetics* 49:49-67 (1964); Hill, W. G. & Robertson, A. *Theor. Appl. Genet.* 22:226-231 (1968)). Both measures range from 0 (no disequilibrium) to 1 ('complete' disequilibrium), but their interpretation is slightly different. |D'| is defined in such a way that it is equal to 1 if just two or three of the possible haplotypes are present, and it is <1 if all four possible haplotypes are present. Therefore, a value of |D'| that is <1 indicates that historical recombination may have occurred between two sites (recurrent mutation can also cause |D'| to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, or at least 0.99. In one preferred embodiment, the significant $r^2$ value can be at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. It is measured by correlation coefficient or |D'| ($r^2$ up to 1.0 and |D'| up to 1.0). In certain embodiments, linkage disequilibrium is defined in terms of values for both the $r^2$ and |D'| measures. In one such embodiment, a significant linkage disequilibrium is defined as $r^2>0.1$ and |D'|>0.8. In another embodiment, a significant linkage disequilibrium is defined as $r^2>0.2$ and |D'|>0.9. Other combinations and permutations of values of $r^2$ and |D'| for determining linkage disequilibrium are also contemplated, and are also within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http://www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were independent at the population level (i.e., no LD), then every single one of them would need to be investigated in association studies, to assess all the different polymorphic states. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, *Science* 273:1516-1517 (1996); Maniatis, N., et al., *Proc Natl Acad Sci USA* 99:2228-2233 (2002); Reich, D E et al, *Nature* 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., *Nature Reviews Genetics* 4:587-597 (2003); Daly, M. et al., *Nature Genet.* 29:229-232 (2001); Gabriel, S. B. et al., *Science* 296:2225-2229 (2002); Patil, N. et al., *Science* 294:1719-1723 (2001); Dawson, E. et al., *Nature* 418:544-548 (2002); Phillips, M. S. et al., *Nature Genet.* 33:382-387 (2003)).

There are two main methods for defining these haplotype blocks: blocks can be defined as regions of DNA that have limited haplotype diversity (see, e.g., Daly, M. et al., *Nature Genet.* 29:229-232 (2001); Patil, N. et al., *Science* 294:1719-1723 (2001); Dawson, E. et al., *Nature* 418:544-548 (2002); Zhang, K. et al., *Proc. Natl. Acad. Sci. USA* 99:7335-7339 (2002)), or as regions between transition zones having extensive historical recombination, identified using linkage disequilibrium (see, e.g., Gabriel, S. B. et al., *Science* 296:2225-2229 (2002); Phillips, M. S. et al., *Nature Genet.* 33:382-387 (2003); Wang, N. et al., *Am. J. Hum. Genet.* 71:1227-1234 (2002); Stumpf, M. P., and Goldstein, D. B., *Curr. Biol.* 13:1-8 (2003)). More recently, a fine-scale map of recombination rates and corresponding hotspots across the human genome has been generated (Myers, S., et al., *Science* 310: 321-32324 (2005); Myers, S. et al., *Biochem Soc Trans* 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks (LD blocks) can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait, and as such are useful for use in the methods and kits of the present invention. One or more causative (functional) variants or mutations may reside within the region found to be associating to the disease or trait. The functional variant may be another SNP, a tandem repeat polymorphism (such as a minisatellite or a microsatellite), a transposable element, or a copy number variation, such as an inversion, deletion or insertion. Such variants in LD with the variants described herein may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc. B*, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a susceptibility region, for example within an LD block, association of all possible combinations of genotyped markers within the region is studied. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of a significant marker and/or haplotype association.

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics*, 60(2):368-75 (2004)) as a natural extension of information measures defined for linkage analysis, and is implemented in NEMO.

Statistical Analysis

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families to the study, first and second-degree relatives can be eliminated from the patient list. Furthermore, the test can be repeated for association correcting for any remaining relatedness among the patients, by extending a variance adjustment procedure previously described (Risch, N. & Teng, *J. Genome Res.*, 8:1273-1288 (1998)) for sibships so that it can be applied to general familial relationships, and present both adjusted and unadjusted p-values for comparison. The method of genomic controls (Devlin, B. & Roeder, K. *Biometrics* 55:997 (1999)) can also be used to adjust for the relatedness of the individuals and possible stratification. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, risk $(h_i)$/risk $(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

An association signal detected in one association study may be replicated in a second cohort, ideally from a different population (e.g., different region of same country, or a different country) of the same or different ethnicity. The advantage of replication studies is that the number of tests performed in the replication study is usually quite small, and hence the less stringent the statistical measure that needs to be applied. For example, for a genome-wide search for susceptibility variants for a particular disease or trait using 300,000 SNPs, a correction for the 300,000 tests performed (one for each SNP) can be performed. Since many SNPs on the arrays typically used are correlated (i.e., in LD), they are not independent. Thus, the correction is conservative. Nevertheless, applying this correction factor requires an observed P-value of less than $0.05/300,000=1.7\times10^{-7}$ for the signal to be considered significant applying this conservative test on results from a single study cohort. Obviously, signals found in a genome-wide association study with P-values less than this conservative threshold are a measure of a true genetic effect, and replication in additional cohorts is not necessarily from a statistical point of view. Importantly, however, signals with P-values that are greater than this threshold may also be due to a true genetic effect. Thus, since the correction factor depends on the number of statistical tests performed, if one signal (one SNP) from an initial study is replicated in a second case-control cohort, the appropriate statistical test for significance is that for a single statistical test, i.e., P-value less than 0.05. Replication studies in one or even several additional case-control cohorts have the added advantage of providing assessment of the association signal in additional populations, thus simultaneously confirming the initial finding and providing an assessment of the overall significance of the genetic variant(s) being tested in human populations in general.

The results from several case-control cohorts can also be combined to provide an overall assessment of the underlying effect. The methodology commonly used to combine results from multiple genetic association studies is the Mantel-Haenszel model (Mantel and Haenszel, *J Natl Cancer Inst* 22:719-48 (1959)). The model is designed to deal with the situation where association results from different populations, with each possibly having a different population frequency of the genetic variant, are combined. The model combines the results assuming that the effect of the variant on the risk of the disease, a measured by the OR or RR, is the same in all populations, while the frequency of the variant may differ between the populations. Combining the results from several populations has the added advantage that the overall power to detect a real underlying association signal is increased, due to the increased statistical power provided by the combined cohorts. Furthermore, any deficiencies in individual studies, for example due to unequal matching of cases and controls or population stratification will tend to balance out when results from multiple cohorts are combined, again providing a better estimate of the true underlying genetic effect.

Methods of Determining Susceptibility to Atrial Fibrillation, Atrial Flutter and Stroke The present inventors have for the first time shown that certain polymorphic variants are associated with risk of developing Atrial Fibrillation, Atrial Flutter and Stroke. Certain alleles of certain polymorphic markers have been found to be present at increased frequency in individuals with diagnosis of these conditions, compared with controls. These polymorphic markers are thus associated with risk of these conditions. Without intending to being bound to a particular theory, the particular polymorphic markers described herein, as well as markers in linkage disequilibrium with these polymorphic markers, are contemplated to be useful as markers for determining susceptibility to any one or more, or any combination, of these conditions. These markers are believed to be useful in a range of diagnostic applications, as described further herein.

Accordingly, in one aspect the invention provides a method of determining a susceptibility to a condition selected from the group consisting of: a cardiac arrhythmia selected from Atrial Fibrillation and Atrial Flutter, and Stroke, the method comprising: obtaining sequence data about a human individual identifying at least one allele of at least one polymorphic marker, wherein different alleles of the at least one polymorphic marker are associated with different susceptibilities to the condition in humans, and determining a susceptibility to the condition from the sequence data, wherein the at least one polymorphic marker is selected from the group consisting of rs7193343, rs10077199, rs10490066, rs10516002, rs10519674, rs1394796, rs2935888, rs4560443, rs6010770 and rs7733337, and markers in linkage disequilibrium therewith.

Nucleic acid sequence data can be obtained for example by analyzing sequence of the at least one polymorphic marker in a biological sample from the individual. Alternatively, nucleic acid sequence data can be obtained in a genotype dataset from the human individual and analyzing sequence of the at least one polymorphic marker in the dataset. Such analysis in certain embodiments comprises determining the presence or absence of a particular allele of specific polymorphic markers.

In certain embodiments, the method comprises obtaining sequence data in vitro. This means that sequence data is obtained by in vitro means. For example, the method may comprise obtaining sequence data from a sample from the individual, or the method may comprise obtaining sequence data from a dataset or other preexisting record about the individual. In one embodiment, the method comprises obtaining sequence data from a sample from the individual, or from a preexisting record about the individual. In one embodiment, the preexisting record is a sequence dataset. In another embodiment, the preexisting record is a genotype dataset.

In certain embodiments of the invention, the at least one polymorphic marker is selected from the group consisting of rs1531202, rs2124786, rs7690053, rs17686902, rs2168580, rs2881736, rs17636187, rs2347824, rs17636490, rs4035252, rs12501809, rs4560443, rs11131484, rs17688509, rs6852697, rs17637486, rs1316996, rs1375470, rs10027594, rs1349182, rs6551792, rs1449196, rs2881806, rs2053844, rs17084483, rs1449187, rs10028878, rs1579965, rs17697026, rs11728458, rs10519674, rs7164994, rs16954910, rs8040523, rs7723988, rs11739151, rs6556151, rs4242182, rs2381939, rs14459, rs4868444, rs10057011, rs7733337, rs12995889, rs10497971, rs6734836, rs10186681, rs1394781, rs13019524, rs4627509, rs12105481, rs1394796, rs4673664, rs6757140, rs7569142, rs1505367, rs1394791, rs1505376, rs2062930, rs1505371, rs17259208, rs1505370, rs2170529, rs10168850, rs17325821, rs17325842, rs10497975, rs6735807, rs6892188, rs2407066, rs1986932, rs17248426, rs1604827, rs6866140, rs702604, rs2407068, rs271247, rs7729734, rs3776742, rs7713737, rs10077199, rs8091729, rs9946582, rs9319738, rs8083791, rs12455127, rs17832178, rs11874708, rs10516002, rs12957615, rs1046789, rs16983293, rs6010770, rs2982506, rs2982508, rs2982510, rs2935888, rs2294752, rs7591835, rs6759758, rs10490066, rs11125830, rs16971447, rs16971471, rs7193343, rs719353, rs719354, rs2106261, rs1548374, rs879324, rs8057081, rs12932445, rs9940321, rs340263, rs391398, rs340234, rs340233, rs340229, rs340261, rs340293, rs340241, rs4679844, rs7618072, rs9855092, and rs1501293.

In certain embodiments, the markers in linkage disequilibrium with rs7193343 are selected from the group consisting of rs16971447, rs16971471, rs719353, rs719354, rs2106261, rs1548374, rs879324, rs8057081, rs12932445, and rs9940321. In certain embodiments, markers in linkage disequilibrium with rs7618072 are selected from the group consisting of rs7618072, rs340263, rs391398, rs340234, rs340233, rs340229, rs340261, rs340293, rs340241, rs4679844, rs9855092, and rs1501293. In certain embodiments, markers in linkage disequilibrium with rs4560443 are selected from the group consisting of rs1531202, rs2124786, rs7690053, rs17686902, rs2168580, rs2881736, rs17636187, rs2347824, rs17636490, rs4035252, rs12501809, rs4560443, rs11131484, rs17688509, rs6852697, rs17637486, rs1316996, rs1375470, rs10027594, rs1349182, rs6551792, rs1449196, rs2881806, rs2053844, rs17084483, rs1449187, rs10028878, rs1579965, rs17697026, and rs11728458. In certain embodiments, markers in linkage disequilibrium with rs10519674 are selected from the group consisting of rs10519674, rs7164994, rs16954910, and rs8040523. In certain embodiments, markers in linkage disequilibrium with rs7733337 are selected from the group consisting of rs7723988, rs11739151, rs6556151, rs4242182, rs2381939, rs14459, rs4868444, rs10057011, and rs7733337. In certain embodiments, markers in linkage disequilibrium with rs1394796 are selected from the group consisting of rs12995889, rs10497971, rs6734836, rs10186681, rs1394781, rs13019524, rs4627509, rs12105481, rs1394796, rs4673664, rs6757140, rs7569142, rs1505367, rs1394791, rs1505376, rs2062930, rs1505371, rs17259208, rs1505370, rs2170529, rs10168850, rs17325821, rs17325842, rs10497975, and rs6735807. In certain embodiments, markers in linkage disequilibrium with rs10077199 are selected from the group consisting of rs6892188, rs2407066, rs1986932, rs17248426, rs1604827, rs6866140, rs702604, rs2407068, rs271247, rs7729734, rs3776742, rs7713737, and rs10077199. In certain embodiments, markers in linkage disequilibrium with rs10516002 are selected from the group consisting of rs8091729, rs9946582, rs9319738, rs8083791, rs12455127, rs17832178, rs11874708, rs10516002, and rs12957615. In certain embodiments, markers in linkage disequilibrium with rs6010770 are selected from the group consisting of rs1046789, rs16983293, and rs6010770. In certain embodiments, markers in linkage disequilibrium with rs2935888 are selected from the group consisting of rs2982506, rs2982508, rs2982510, rs2935888, and rs2294752. In certain embodiments, markers in linkage disequilibrium with rs10490066 are selected from the group consisting of rs7591835, rs6759758, rs10490066, and rs11125830.

In preferred embodiments, the markers useful in the methods of the invention are selected from the group consisting of rs7193343, rs10077199, rs10490066, rs10516002, rs10519674, rs1394796, rs2935888, rs4560443, rs6010770 and rs7733337. In one preferred embodiment, the marker is rs7193343. In another preferred embodiment, the marker is rs7618072.

Individuals who carry at least one copy of a marker allele selected from the group consisting of at least one allele is selected from the group consisting of the T allele of rs7193343, the T allele of rs7618072, the T allele of rs10077199, the A allele of rs10490066, the A allele of rs10516002, the G allele of rs10519674, the C allele of rs1394796, the T allele of rs2935888, the T allele of rs4560443, the G allele of rs6010770 and the T allele of rs7733337 are in certain embodiment at increased susceptibility of the condition.

The risk is in certain embodiments characterized by a particular value of the relative risk (RR) conferred by the risk variants (at-risk alleles). In certain embodiments, risk is characterized by values of relative risk of at least 1.10, at least 1.11, at least 1.12, at least 1.13, at least 1.14, at least 1.15, at least 1.16, at least 1.17, at least 1.18, at least 1.19 or at least 1.20.

Homozygous individuals carrying two copies of at-risk variants in their genome are at particularly high risk of the condition. Thus, certain embodiments relate to determination of a susceptibility, wherein individuals carrying two copies of an at-risk variant for the condition are particularly high risk of the condition.

In certain embodiments of the invention, the sequence data is amino acid sequence data. Polymorphic markers can result in alterations in the amino acid sequence of encoded polypeptide or protein sequence. In certain embodiments, the analysis of amino acid sequence data comprises determining the presence or absence of an amino acid substitution in the amino acid encoded by the at least one polymorphic marker. Sequence data can in certain embodiments be obtained by analyzing the amino acid sequence encoded by the at least one polymorphic marker in a biological sample obtained from the individual.

In general, sequence data can be obtained by analyzing a sample from an individual, or by analyzing information about specific markers in a genotype database. In certain embodiments, sequence data can be obtained through nucleic acid sequence information or amino acid sequence information from a preexisting record. Such a preexisting record can be any documentation, database or other form of data storage containing such information.

Determination of a susceptibility or risk of an individual for a particular condition in general comprises comparison of the genotype information (sequence information) to a record (e.g., a dataset) or database providing a correlation about particular polymorphic marker(s) and susceptibility to a particular condition. Thus, in specific embodiments, determining a susceptibility comprises comparing sequence data for an individual to a database containing correlation data between at least one polymorphic marker and susceptibility to the condition. In certain embodiments, the database comprises at least one measure of susceptibility to the condition for at least one polymorphic marker. In certain embodiments, the database comprises a look-up table comprising at least one measure of susceptibility to the condition for at least one polymorphic marker. The measure of susceptibility may for example in the form of relative risk (RR), absolute risk (AR), percentage (%) or other convenient measure for describing genetic susceptibility of individuals.

Certain embodiments of the invention relate to markers located within the LD Block C16 as defined herein. Thus, in certain embodiments, sequence data is obtained about at least one marker within LDBlock C16. In certain embodiments, surrogate markers of marker rs7193343 are located within LD Block C16 as set forth in SEQ ID NO:1. It is however also contemplated that surrogate markers may be located outside the LD Block C16 as defined in physical terms (i.e., in terms of genomic locations; SEQ ID NO:1). Thus, other embodiments of the invention are not confined to markers located within the physical boundaries of LD Block C16 as defined, but are useful surrogate markers due to being in LD with at least one marker within LD Block C16 (e.g., rs7193343).

Another aspect of the invention relates to a method for determining a susceptibility to a condition selected from the group consisting of: a cardiac arrhythmia selected from Atrial Fibrillation and Atrial Flutter, and Stroke, in a human individual comprising determining the presence or absence of at least one allele of at least one polymorphic marker in a nucleic acid sample obtained from the individual, or in a genotype dataset from the individual, wherein the at least one polymorphic marker is selected from the group consisting of rs7193343, rs7618072, rs10077199, rs10490066, rs10516002, rs10519674, rs1394796, rs2935888, rs4560443, rs6010770 and rs7733337, and markers in linkage disequilibrium therewith, and wherein determination of the presence of the at least one allele is indicative of a susceptibility to the condition. Determination of the presence of an allele that correlates with the condition is indicative of an increased susceptibility to the condition. Individuals who are homozygous for such alleles are particularly susceptible to the condition. On the other hand, individuals who do not carry such at-risk alleles are at a decreased susceptibility of developing the condition. For SNPs, such individuals will be homozygous for the alternate (protective) allele of the polymorphism.

Determination of susceptibility is in some embodiments reported using non-carriers of the at-risk alleles of polymorphic markers. In certain embodiments, susceptibility is reported based on a comparison with the general population, e.g. compared with a random selection of individuals from the population.

In certain embodiments, polymorphic markers are detected by sequencing technologies. Obtaining sequence information about an individual identifies particular nucleotides at particular positions in the genome, i.e. in the context of a nucleotide sequence. For SNPs, sequence information about a single unique sequence site (a single nucleotide position) is sufficient to identify alleles for that particular SNP. For markers comprising more than one nucleotide, sequence information about the genomic region of the individual that contains the polymorphic site identifies the alleles of the individual for the particular site. The sequence information can be obtained from a sample from the individual. In certain embodiments, the sample is a nucleic acid sample. In certain other embodiments, the sample is a protein sample.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have also been developed, and such methods are also contemplated to be useful for obtaining sequence information. These include pyrosequencing technology (Ronaghi, M. et al. *Anal Biochem* 267:65-71 (1999); Ronaghi, et al. *Biotechniques* 25:876-878 (1998)), e.g. 454 pyrosequencing (Nyren, P., et al. *Anal Biochem* 208:171-175 (1993)), Illumina/Solexa sequencing technology (http://www.illumina.com; see also Strausberg, R L, et al *Drug Disc Today* 13:569-577 (2008)), and Supported Oligonucleotide Ligation and Detection Platform (SOLID) technology (Applied Biosystems, http://www.appliedbiosystems.com); Strausberg, R L, et al *Drug Disc Today* 13:569-577 (2008).

It is possible to impute or predict genotypes for un-genotyped relatives of genotyped individuals. For every un-genotyped case, it is possible to calculate the probability of the genotypes of its relatives given its four possible phased genotypes. In practice it may be preferable to include only the genotypes of the case's parents, children, siblings, half-siblings (and the half-sibling's parents), grand-parents, grand-children (and the grand-children's parents) and spouses. It will be assumed that the individuals in the small sub-pedigrees created around each case are not related through any path not included in the pedigree. It is also assumed that alleles that are not transmitted to the case have the same frequency—the population allele frequency. The probability of the genotypes of the case's relatives can then be computed by:

$$Pr(\text{genotypes of relatives}; \theta) = \sum_{h \in \{AA, AG, GA, GG\}} Pr(h; \theta) Pr(\text{genotypes of relatives} \mid h),$$

where $\theta$ denotes the A allele's frequency in the cases. Assuming the genotypes of each set of relatives are independent, this allows us to write down a likelihood function for $\theta$:

$$L(\theta) = \prod_i Pr(\text{genotypes of relatives of case } i; \theta). \qquad (*)$$

This assumption of independence is usually not correct. Accounting for the dependence between individuals is a difficult and potentially prohibitively expensive computational task. The likelihood function in (*) may be thought of as a pseudolikelihood approximation of the full likelihood function for $\theta$ which properly accounts for all dependencies. In general, the genotyped cases and controls in a case-control association study are not independent and applying the case-control method to related cases and controls is an analogous approximation. The method of genomic control (Devlin, B. et al., *Nat Genet.* 36, 1129-30; author reply 1131 (2004)) has proven to be successful at adjusting case-control test statistics for relatedness. We therefore apply the method of genomic control to account for the dependence between the terms in our pseudolikelihood and produce a valid test statistic.

Fisher's information can be used to estimate the effective sample size of the part of the pseudolikelihood due to un-genotyped cases. Breaking the total Fisher information, I, into the part due to genotyped cases, $I_g$, and the part due to ungenotyped cases, $I_u$, $I=I_g+I_u$, and denoting the number of genotyped cases with N, the effective sample size due to the un-genotyped cases is estimated by $$\frac{I_u}{I_g} N.$$

In the present context, and individual who is at an increased susceptibility (i.e., increased risk) for a particular condition, is an individual in whom at least one specific allele at one or more polymorphic marker or haplotype conferring increased susceptibility (increased risk) for the condition is identified (i.e., at-risk marker alleles or haplotypes). The at-risk marker or haplotype is one that confers an increased risk (increased susceptibility) of the condition. In one embodiment, significance associated with a marker or haplotype is measured by a relative risk (RR). In another embodiment, significance associated with a marker or haplotye is measured by an odds ratio (OR). In a further embodiment, the significance is measured by a percentage. In one embodiment, a significant increased risk is measured as a risk (relative risk and/or odds ratio) of at least 1.05, including but not limited to: at least 1.10, at least 1.11, at least 1.12, at least 1.13, at least 1.14, at least 1.15, at least 1.16, at least 1.17, at least 1.18, at least 1.19, at least 1.20, at least 1.30, at least 1.40, at least 1.50, at least 1.60, at least 1.70, at least 1.80, at least 1.90, and at least 2.0. In a particular embodiment, a risk (relative risk and/or odds ratio) of at least 1.08 is significant. In another particular embodiment, a risk of at least 1.13 is significant. In yet another embodiment, a risk of at least 1.19 is significant. Other cutoffs are also contemplated, e.g., at least 1.15, 1.25, 1.35, and so on, and such cutoffs are also within scope of the present invention. In other embodiments, a significant increase in risk is at least about 5%, including but not limited to about 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, and at least 100%. In one particular embodiment, a significant increase in risk is at least 10%. In another particular embodiment, a significant increase in risk is at least 12%. In another particular embodiment, a significant increase in risk is at least 15%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

In certain embodiments, it is useful to determine risk for individuals who are homozygous for particular variants. For example, individuals who are homozygous carriers of at-risk variants are at particularly high risk of developing the particular condition. Such individuals carry two copies of the at-risk variant in their genome, and since the effect of each allele is usually independent, the effect of having two copies of an at-risk variant leads to an overall risk that is the risk for one copy of the variant squared.

An at-risk polymorphic marker or haplotype as described herein is one where at least one allele of at least one marker or haplotype is more frequently present in an individual at risk for, or diagnosed with a condition selected from the group consisting of: a cardiac arrhythmia selected from Atrial Fibrillation and Atrial Flutter, and Stroke (affected), compared to the frequency of its presence in a comparison group (control), such that the presence of the marker or haplotype is indicative of susceptibility to the condition. The control group may in one embodiment be a population sample, i.e. a random sample from the general population. In another embodiment, the control group is represented by a group of individuals who are disease-free. Such disease-free controls may in one embodiment be characterized by the absence of one or more specific disease-associated symptoms for the particular conditions. Alternatively, the disease-free controls are those that have not been diagnosed with the condition. In another embodiment, the disease-free control group is characterized by the absence of one or more risk factors for the condition. Such risk factors are in one embodiment at least one environmental risk factor. In certain embodiments, the risk factors comprise at least one additional genetic risk factor for the condition, e.g., risk factors for Atrial Fibrillation, Atrial Flutter and/or stroke.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes. Other statistical tests of association known to the skilled person are also contemplated and are also within scope of the invention.

In other embodiments of the invention, an individual who is at a decreased susceptibility (i.e., at a decreased risk) for a condition is an individual in whom at least one specific allele at one or more polymorphic marker or haplotype conferring decreased susceptibility for the condition is identified. The marker alleles and/or haplotypes conferring decreased risk are also said to be protective. In one aspect, the protective marker or haplotype is one that confers a significant decreased risk (or susceptibility) of the condition. In one embodiment, significant decreased risk is measured as a relative risk (or odds ratio) of less than 0.95, including but not limited to less than 0.9, less than 0.8, less than 0.7, less than 0.6, less than 0.5, less than 0.4, less than 0.3, less than 0.2 and less than 0.1. In one particular embodiment, significant decreased risk is less than 0.90. In another embodiment, significant decreased risk is less than 0.85. In yet another embodiment, significant decreased risk is less than 0.80. In another embodiment, the decrease in risk (or susceptibility) is at least 10%, including but not limited to at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, and at least 50%. In one particular embodiment, a significant decrease in risk is at least about 10%. In another embodiment, a significant decrease in risk is at least about 15%. In another embodiment, the decrease in risk is at least about 20%. Other cutoffs or ranges as deemed suitable by the person skilled in the art to characterize the invention are however also contemplated, and those are also within scope of the present invention.

The person skilled in the art will appreciate that for markers with two alleles present in the population being studied (such as SNPs), and wherein one allele is found in increased frequency in a group of individuals with a particular condition (e.g., Atrial Fibrillation, Atrial Flutter, Stroke), compared with controls, the other allele of the marker will be found in decreased frequency in the group of individuals, compared with controls. In such a case, one allele of the marker (the one found in increased frequency in individuals with the condition) will be the at-risk allele, while the other allele will be a protective allele.

A genetic variant associated with a disease or a trait can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n \times 2^P$; where n is the number autosomal loci and p the number of gonosomal (sex chromosomal) loci. Overall risk assessment calculations for a plurality of risk variants usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk—is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider a total of eleven variants that are described herein to be associated with risk of Atrial Fibrillation, Atrial Flutter and/or Stroke (rs7193343, rs7618072, rs10077199, rs10490066, rs10516002, rs10519674, rs1394796, rs2935888, rs4560443, rs6010770 and rs7733337). All of these markers are on the autosomes. The total number of theoretical genotypic combinations is then $3^{11}=177147$. As another example, we can consider the markers rs7193343 (described herein), rs2200733 and rs10033464 (Gudbjartsson, D F, et al. Nature 448:353-7 (2007)). For these three variants, all on the autosomes, the number of theoretical genotype combinations is $3^3=27$. Some of the theoretical genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

It will be apparent to the skilled person that any one, or a combination of, the markers described herein, can be evaluated to perform overall risk assessment. The variants can also be combined with any other genetic markers conferring risk of Atrial Fibrillation/Atrial Flutter and/or Stroke (e.g., rs2200733 and rs10033464). Thus, in one embodiment, marker rs7193343, or a marker in linkage disequilibrium therewith, is evaluated in combination with marker rs2200733 and/or marker rs10033464. Alternatively, combinations of markers in linkage disequilibrium with these markers can be evaluated.

The procedures or methods of the invention in one embodiment entail at least one polymorphic marker or haplotype comprising a contiguous nucleic acid fragment of LD block C16 as defined herein, or the complement thereof, wherein the fragment is less than 500 nucleotides in size and specifically hybridizes to a complimentary segment of LD block C16. In one embodiment, the fragment is more than 15 nucleotides and less than 400 nucleotides in size, and wherein the fragment specifically hybridizes to a complimentary segment of LD block C16.

Some embodiments of the invention relate to a further step of assessing at least one additional biomarker for atrial fibrillation, atrial flutter or stroke, wherein combining the genetic information from the markers provides risk assessment for atrial fibrillation, atrial flutter and/or stroke. In some of these embodiments, the biomarker is a genetic marker or haplotype, i.e. genetic risk factors shown to be, or contemplated to be, related to increased or decreased risk of atrial fibrillation, atrial flutter and/or stroke. In other embodiments the biomarker is a protein biomarker. The protein biomarker is in some embodiments selected from fibrin D-dimer, prothrombin activation fragment 1.2 (F1.2), thrombin-antithrombin III complexes (TAT), fibrinopeptide A (FPA), lipoprotein-associated phospholipase A2 (Ip-PLA2), beta-thromboglobulin, platelet factor 4, P-selectin, von Willebrand Factor, pro-natriuretic peptide (BNP), matrix metalloproteinase-9 (MMP-9), PARK7, nucleoside diphosphate kinase (NDKA), tau, neuron-specific enolase, B-type neurotrophic growth factor, astroglial protein S-100b, glial fibrillary acidic protein, C-reactive protein, seum amyloid A, marix metalloproteinase-9, vascular and intracellular cell adhesion molecules, tumor necrosis factor alpha, and interleukins, including interleukin-1, -6, and -8). In one embodiment, the at least one biomarker includes progenitor cells. In particular embodiments, more than one biomarker is determined. In a preferred embodiment, the biomarker is measured in plasma from the individual. Other embodiments further relate to combining non-genetic information to make risk assessment, diagnosis, or prognosis of atrial fibrillation, and/or stroke in the individual. The non-genetic information can comprise age, age at onset of disease, gender, ethnicity, previous disease diagnosis, e.g., diagnosis of cardiag arrhythmia (e.g., atrial fibrillation) and stroke, medical history of the individual, family history of disease, biochemical measurements, and clinical measurements (e.g., blood pressure, serum lipid levels). Analysis of such combined information from various genetic markers, or genetic markers plus non-genetic markers is possible by methods known to those skilled in the art. In one embodiment, analysis is performed calculating overall risk by logistic regression.

The invention further relates to a method of diagnosing increased susceptibility of stroke in a human individual, comprising the steps of (a) determining whether the individual has experienced symptoms associated with a condition selected from the group consisting of Atrial Fibrillation, Atrial Flutter or a Transient Ischemic Attack; (b) determining whether a nucleic acid sample from the individual, or a genotype dataset from the individual, comprises at least one copy of an at-risk allele of at least one polymorphic marker selected from the group consisting of rs7193343, rs7618072, rs10077199, rs10490066, rs10516002, rs10519674, rs1394796, rs2935888, rs4560443, rs6010770 and rs7733337, and markers in linkage disequilibrium therewith; wherein the presence of symptoms associated with the condition and the presence of the at least one copy of the at-risk allele is indicative of increased susceptibility of stroke. In one preferred embodiment, the at least one polymorphic marker is selected from the group consisting of rs7193343, and markers in linkage disequilibrium therewith.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3. The creation of a model to calculate the overall genetic risk involves two steps: i) conversion of odds-ratios for a single genetic variant into relative risk and ii) combination of risk from multiple variants in different genetic loci into a single relative risk value deriving risk from odds-ratios. Most gene discovery studies for complex diseases that have been published to date in authoritative journals have employed a case-control design because of their retrospective setup. These studies sample and genotype a selected set of cases (people who have the specified disease condition) and control individuals. The interest is in genetic variants (alleles) which frequency in cases and controls differ significantly.

The results are typically reported in odds-ratios, that is the ratio between the fraction (probability) with the risk variant (carriers) versus the non-risk variant (non-carriers) in the groups of affected versus the controls, i.e. expressed in terms of probabilities conditional on the affection status:

$$OR=(Pr(c|A)/Pr(nc|A))/(Pr(c|C)/Pr(nc|C))$$

Sometimes it is however the absolute risk for the disease that we are interested in, i.e. the fraction of those individuals carrying the risk variant who get the disease or in other words the probability of getting the disease. This number cannot be directly measured in case-control studies, in part, because the ratio of cases versus controls is typically not the same as that in the general population. However, under certain assumption, we can estimate the risk from the odds-ratio.

It is well known that under the rare disease assumption, the relative risk of a disease can be approximated by the odds-ratio. This assumption may however not hold for many common diseases. Still, it turns out that the risk of one genotype variant relative to another can be estimated from the odds-ratio expressed above. The calculation is particularly simple under the assumption of random population controls where the controls are random samples from the same population as the cases, including affected people rather than being strictly unaffected individuals. To increase sample size and power, many of the large genome-wide association and replication studies used controls that were neither age-matched with the cases, nor were they carefully scrutinized to ensure that they did not have the disease at the time of the study. Hence, while not exactly, they often approximate a random sample from the general population. It is noted that this assumption is rarely expected to be satisfied exactly, but the risk estimates are usually robust to moderate deviations from this assumption.

Calculations show that for the dominant and the recessive models, where we have a risk variant carrier, "c", and a non-carrier, "nc", the odds-ratio of individuals is the same as the risk-ratio between these variants:

$$OR=Pr(A|c)/Pr(A|nc)=r$$

And likewise for the multiplicative model, where the risk is the product of the risk associated with the two allele copies, the allelic odds-ratio equals the risk factor:

$$OR=Pr(A|a)/Pr(A|ab)=Pr(A|ab)/Pr(A|bb)=r$$

Here "a" denotes the risk allele and "b" the non-risk allele. The factor "r" is therefore the relative risk between the allele types.

For many of the studies published in the last few years, reporting common variants associated with complex diseases, the multiplicative model has been found to summarize the effect adequately and most often provide a fit to the data superior to alternative models such as the dominant and recessive models.

The risk relative to the average population risk. It is most convenient to represent the risk of a genetic variant relative to the average population since it makes it easier to communicate the lifetime risk for developing the disease compared with the baseline population risk. For example, in the multiplicative model we can calculate the relative population risk for variant "aa" as:

$$RR(aa)=Pr(A|aa)/Pr(A)=(Pr(A|aa)/Pr(A|bb))/(Pr(A)/Pr(A|bb))=r^2/(Pr(aa)r^2+Pr(ab)r+Pr(bb))=r^2/(p^2r^2+2pq\ r+q^2)=r^2/R$$

Here "p" and "q" are the allele frequencies of "a" and "b" respectively. Likewise, we get that RR(ab)=r/R and RR(bb)=1/R. The allele frequency estimates may be obtained from the publications that report the odds-ratios and from the HapMap database. Note that in the case where we do not know the genotypes of an individual, the relative genetic risk for that test or marker is simply equal to one.

As an example, for Atrial Fibrillation, allele T of the disease-associated marker rs7193343 has an allelic OR of 1.22 and a frequency (p) around 0.2 in white populations (Table 1). The genotype relative risk compared to genotype CC (homozygous for the alternate allele of rs7193343) are estimated based on the multiplicative model.

For TT it is 1.22×1.22=1.49; for CT it is simply the OR 1.22, and for CC it is 1.0 bp definition.

The frequency of allele C is q=1−p=1−0.2=0.8. Population frequency of each of the three possible genotypes at this marker is:

$$Pr(TT)=p^2=0.04, Pr(CT)=2pq=0.32, \text{ and } Pr(CC)=q^2=0.64$$

The average population risk relative to genotype CC (which is defined to have a risk of one) is:

$$R=0.04\times1.49+0.32\times1.22+0.64\times1=1.09$$

Therefore, the risk relative to the general population (RR) for individuals who have one of the following genotypes at this marker is:

$$RR(TT)=1.49/1.09=1.37, RR(CT)=1.22/1.09=1.12, RR(TT)=1/1.09=0.92.$$

Combining the risk from multiple markers. When genotypes of many SNP variants are used to estimate the risk for an individual, unless otherwise stated, a multiplicative model for risk can be assumed. This means that the combined genetic risk relative to the population is calculated as the product of the corresponding estimates for individual markers, e.g. for two markers g1 and g2:

$$RR(g1,g2)=RR(g1)RR(g2)$$

The underlying assumption is that the risk factors occur and behave independently, i.e. that the joint conditional probabilities can be represented as products:

$$Pr(A|g1,g2)=Pr(A|g1)Pr(A|g2)/Pr(A) \text{ and } Pr(g1,g2)= Pr(g1)Pr(g2)$$

Obvious violations to this assumption are markers that are closely spaced on the genome, i.e. in linkage disequilibrium such that the concurrence of two or more risk alleles is correlated. In such cases, we can use so called haplotype modeling where the odds-ratios are defined for all allele combinations of the correlated SNPs.

As is in most situations where a statistical model is utilized, the model applied is not expected to be exactly true since it is not based on an underlying bio-physical model. However, the multiplicative model has so far been found to fit the data adequately, i.e. no significant deviations are detected for many common diseases for which many risk variants have been discovered.

As an example, let's consider a case of 8 markers that are associated with a particular trait or disease, along with the risk relative to the population at each marker:

| Marker 1 | TT | Calculated risk: | RR(TT) = 1.37 |
| --- | --- | --- | --- |
| Marker 2 | CT | Calculated risk: | RR(CC) = 1.56 |
| Marker 3 | AC | Calculated risk: | RR(AC) = 1.39 |
| Marker 4 | GT | Calculated risk: | RR(GT) = 0.99 |
| Marker 5 | AA | Calculated risk: | RR(AA) = 1.19 |
| Marker 6 | GG | Calculated risk: | RR(GG) = 1.21 |
| Marker 7 | GG | Calculated risk: | RR(GG) = 0.82 |
| Marker 8 | AA | Calculated risk: | RR(AA) = 1.14 |

Combined, the overall risk relative to the population for an individual with the above genotype combination is: $1.25 \times 0.96 \times 1.39 \times 0.99 \times 1.19 \times 1.21 \times 0.82 \times 1.14 = 2.22$.

We can combine risk for any combination of markers in an analogous fashion. For example, for any combination of the markers described herein (e.g., rs7193343, rs7618072, rs10077199, rs10490066, rs10516002, rs10519674, rs1394796, rs2935888, rs4560443, rs6010770 and rs7733337, or surrogate markers) we can determine overall risk in an analogous fashion. We can also determine overall risk for any one, or a combination of, these markers, with other markers described to be associated with risk of Atrial Fibrillation, Atrial Flutter and/or Stroke, such as the markers rs2200733 and rs100334464 on chromosome 4q25. Calculated combined risk can be obtained for any combination of these markers, or combinations with other markers associated with risk of prostate cancer, such as the eight markers listed in the above.

Risk Assessment for Atrial Fibrillation, Atrial Flutter and Stroke

As described herein, certain polymorphic markers and haplotypes comprising such markers are found to be useful for risk assessment of atrial fibrillation, atrial flutter and/or stroke. Risk assessment can involve the use of any one or a plurality of such markers. Particular alleles of polymorphic markers (e.g., SNPs) are found more frequently in individuals with atrial fibrillation, atrial flutter and/or stroke, than in individuals without diagnosis of these conditions. Therefore, these marker alleles have predictive value for detecting a susceptibility to atrial fibrillation, atrial flutter and stroke in an individual. Tagging markers in linkage disequilibrium with at-risk variants (or protective variants) described herein can also be used as surrogates for these markers (and/or haplotypes). Such surrogate markers can be located within a particular haplotype block or LD block (e.g., LD Block C16). Such surrogate markers can also sometimes be located outside the physical boundaries of such a haplotype block or LD block, either in close vicinity of the LD block/haplotype block, but possibly also located in a more distant genomic location.

Long-distance LD can for example arise if particular genomic regions (e.g., genes) are in a functional relationship. For example, if two genes encode proteins that play a role in a shared metabolic pathway, then particular variants in one gene may have a direct impact on observed variants for the other gene. Let us consider the case where a variant in one gene leads to increased expression of the gene product. To counteract this effect and preserve overall flux of the particular pathway, this variant may have led to selection of one (or more) variants at a second gene that confers decreased expression levels of that gene. These two genes may be located in different genomic locations, possibly on different chromosomes, but variants within the genes are in apparent LD, not because of their shared physical location within a region of high LD, but rather due to evolutionary forces. Such LD is also contemplated and within scope of the present invention. The skilled person will appreciate that many other scenarios of functional gene-gene interaction are possible, and the particular example discussed here represents only one such possible scenario.

Markers in linkage disequilibrium with any marker shown to be associated with a disease (e.g., Atrial Fibrillation, Atrial Flutter or Stroke) are, by necessity, also associated with the disease. Thus, the surrogate markers of rs7193343 presented in Table 5 must also be associated with Atrial Fibrillation, Atrial Flutter and Stroke. This fact is obvious to the skilled person, who thus knows that surrogate markers may be suitably selected to test an association determined for any particular anchor marker. The stronger the linkage disequilibrium of the surrogate marker to the anchor marker, the better the surrogate, and thus the mores similar the association detected by the surrogate will be to the association detected by the anchor marker. Surrogate markers with values of $r^2$ equal to 1 to the anchor marker (risk marker) are perfect surrogates for the at-risk variant, i.e. genotypes for one marker perfectly predicts genotypes for the other. In other words, the surrrogate will, by necessity, give exactly the same association data to any particular disease as the anchor marker. Markers with smaller values of $r^2$ than 1 can also be selected as surrogates for the at-risk anchor variant. Surrogate markers with smaller values of $r^2$ than 1 may be variants with risk values smaller than for the anchor marker. Alternatively, such surrogate markers may represent variants with relative risk values as high as or possibly even higher than the at-risk variant. In this scenario, the at-risk variant identified may not be the functional variant itself, but is in this instance in linkage disequilibrium with the true functional variant. The functional variant may for example be a tandem repeat, such as a minisatellite or a microsatellite, a transposable element (e.g., an Alu element), or a structural alteration, such as a deletion, insertion or inversion (sometimes also called copy number variations, or CNVs). The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation identify and genotype surrogate markers in linkage disequilibrium with the markers and/or haplotypes as described herein. The tagging or surrogate markers in LD with the at-risk variants detected, also have predictive value for detecting association to the disease, or a susceptibility to the disease, in an individual. These tagging or surrogate markers that are in LD with the markers of the present invention can also include other markers that distinguish among haplotypes, as these similarly have predictive value for detecting susceptibility to the particular disease. In one embodiment, the surrogate markers have values of $r^2$ greater than 0.8 to the anchor marker. In another embodiment, the surrogate markers have values of $r^2$ greater than 0.5 to the anchor marker. In yet another embodiment, the surrogate markers have values of $r^2$ greater than 0.2 to the anchor marker. Other values of $r^2$ may also suitably be used to select surrogate markers, as deemed appropriate by the skilled person.

The present invention can in certain embodiments be practiced by assessing a sample comprising genomic DNA from an individual. Such assessment typically steps that detect the presence or absence of at least one allele of at least one polymorphic marker (e.g., obtain sequence information about at least one polymorphic marker), using methods well known to the skilled person and further described herein, and based on the outcome of such assessment, determine whether the individual from whom the sample is derived is at increased or decreased risk (increased or decreased susceptibility) of atrial fibrillation, atrial flutter and/or stroke. Detecting particular alleles of polymorphic markers can in certain embodiments be done by obtaining nucleic acid sequence data about a particular human individual that identifies at least one allele of at least one polymorphic marker. Different alleles of the at least one marker are associated with different susceptibility to the disease in humans. Obtaining nucleic acid sequence data can comprise nucleic acid sequence at a single nucleotide position, which is sufficient to identify alleles at SNPs. The nucleic acid sequence data can also comprise sequence at any other number of nucleotide positions, in particular for genetic markers that comprise multiple nucleotide positions, and can be anywhere from two to hundreds of thousands, possibly even millions, of nucleotides (in particular, in the case of copy number variations (CNVs)).

In certain embodiments, the invention can be practiced utilizing a dataset comprising information about the genotype status of at least one polymorphic marker associated with a disease (or markers in linkage disequilibrium with at least one marker associated with the disease). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with the disease. A positive result for a variant (e.g., marker allele) associated with the disease, is indicative of the individual from which the dataset is derived is at increased susceptibility (increased risk) of the disease.

In certain embodiments of the invention, a polymorphic marker is correlated to a disease by referencing genotype data for the polymorphic marker to a look-up table that comprises correlations between at least one allele of the polymorphism and the disease. The genotype data is suitably genotype data obtained by analyzing a sample from the individual. In some embodiments, the sample is a nucleic acid sample. In certain embodiments, the genotype data is nucleic acid sequence data. In some embodiments, the table comprises a correlation for one polymorphism. In other embodiments, the table comprises a correlation for a plurality of polymorphisms. In both scenarios, by referencing to a look-up table that gives an indication of a correlation between a marker and the disease, a risk for the disease, or a susceptibility to the disease, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

In certain embodiments of the invention, a plurality of variants (genetic markers, biomarkers and/or haplotypes) is used for overall risk assessment. These variants are in one embodiment selected from the variants as disclosed herein. Other embodiments include the use of the variants of the present invention in combination with other variants known to be useful for diagnosing a susceptibility to atrial fibrillation and/or stroke. In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses or other methods known to the skilled person, may subsequently be used to determine the overall risk conferred based on the genotype status at the multiple loci. Assessment of risk based on such analysis may subsequently be used in the methods, uses and kits of the invention, as described herein.

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined, as discussed in the above. Such markers and/or haplotypes may in those cases be also used as surrogate markers and/or haplotypes for the markers and/or haplotypes physically residing within the haplotype block as defined. As a consequence, markers and haplotypes in LD (typically characterized by inter-marker $r^2$ values of greater than 0.1, such as $r^2$ greater than 0.2, including $r^2$ greater than 0.3, also including markers correlated by values for $r^2$ greater than 0.4) with the markers and haplotypes described herein are also within the scope of the invention, even if they are physically located beyond the boundaries of the haplotype block as defined.

For polymorphic markers comprising two alleles, the opposite allele to the allele found to be in excess in patients (at-risk allele) is found in decreased frequency in patients. These marker alleles are thus protective for the condition affecting the patients, i.e. they confer a decreased risk or susceptibility of individuals carrying these marker alleles will develop the condition.

Certain variants of the present invention, including certain haplotypes comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker allele or haplotype found to be associated with a condition such as atrial fibrillation, atrial flutter and/or stroke, is one in which the marker allele or haplotype is more frequently present in patients, compared to the frequency of its presence in healthy individuals (control), or in randomly selected individuals from the population, wherein the presence of the marker allele or haplotype is indicative of a susceptibility to the condition. In other embodiments, at-risk markers in linkage disequilibrium with one or more markers shown herein to be associated with atrial fibrillation, atrial flutter and/or stroke are tagging markers that are more frequently present in patients, compared to the frequency of their presence in healthy individuals (control) or in randomly selected individuals from the population, wherein the presence of the tagging markers is indicative of increased susceptibility to the condition. In a further embodiment, at-risk markers alleles (i.e. conferring increased susceptibility) in linkage disequilibrium with one or more markers found to be associated with atrial fibrillation, atrial flutter and/or stroke are markers comprising one or more allele that is more frequently present in patients, compared to the frequency of their presence in healthy individuals (control), wherein the presence of the markers is indicative of increased susceptibility to the condition.

Study Population

In a general sense, the methods and kits of the invention can be utilized from samples containing nucleic acid material (DNA or RNA) from any source and from any individual, or from genotype data derived from such samples. In preferred embodiments, the individual is a human individual. The individual can be an adult, child, or fetus. The nucleic acid source may be any sample comprising nucleic acid material, including biological samples, or a sample comprising nucleic acid material derived therefrom. The present invention also provides for assessing markers and/or haplotypes in individuals who are members of a target population.

Such a target population is in one embodiment a population or group of individuals at risk of developing the disease, based on other genetic factors, biomarkers, biophysical parameters (e.g., weight, BMD, blood pressure, lipid measurements), or general health and/or lifestyle parameters (e.g., history of atrial fibrillation, stroke or related diseases, previous diagnosis or family history of these diseases).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset or age at diagnosis of atrial fibrillation, atrial flutter and/or stroke, in any of the age ranges described in the above. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either gender, males or females. In a preferred embodiment, the invention relates to risk of atrial fibrillation, atrial flutter, and/or stroke with an early age at onset. In one embodiment, the age of onset in the individual is of less than 80 years. In another embodiment, the age of onset in the individual is of less than 70 years. In yet another embodiment, the age of onset in the individual is of less than 60 years. Other age cutoffs are possible in alternative embodiments of the invention, and are also contemplated, including, but not limited to, age of onset of less than 75 years, less than 65 years, and less than 55 years.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Styrkarsdottir, U., et al. *N Engl J Med* Apr. 29, 2008 (Epub ahead of print); Thorgeirsson, T., et al. *Nature* 452:638-42 (2008); Gudmundsson, J., et al. *Nat. Genet.* 40:281-3 (2008); Stacey, S. N., et al., *Nat. Genet.* 39:865-69 (2007); Helgadottir, A., et al., *Science* 316:1491-93 (2007); Steinthorsdottir, V., et al., *Nat. Genet.* 39:770-75 (2007); Gudmundsson, J., et al., *Nat. Genet.* 39:631-37 (2007); Frayling, T M, *Nature Reviews Genet.* 8:657-662 (2007); Amundadottir, L. T., et al., *Nat. Genet.* 38:652-58 (2006); Grant, S. F., et al., *Nat. Genet.* 38:320-23 (2006)). Thus, genetic findings in the Icelandic population have in general been replicated in other populations, including populations from Africa and Asia.

It is thus believed that the markers of the present invention found to be associated with atrial fibrillation, atrial flutter and/or stroke will show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Czech, Greek and Turkish populations. The invention furthermore in other embodiments can be practiced in specific human populations that include Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Orogen, She, Tujia, Tu, Xibo, Yi, Mongolan, Naxi, Cambodian, Japanese, Yakut, Melanesian, Papuan, Karitianan, Surui, Colmbian, Maya and Pima.

In certain embodiments, the invention relates to populations that include black African ancestry such as populations comprising persons of African descent or lineage. Black African ancestry may be determined by self reporting as African-Americans, Afro-Americans, Black Americans, being a member of the black race or being a member of the negro race.

For example, African Americans or Black Americans are those persons living in North America and having origins in any of the black racial groups of Africa. In another example, self-reported persons of black African ancestry may have at least one parent of black African ancestry or at least one grandparent of black African ancestry. In another embodiment, the invention relates to individuals of Caucasian origin.

The racial contribution in individual subjects may also be determined by genetic analysis. Genetic analysis of ancestry may be carried out using unlinked microsatellite markers such as those set out in Smith et al. (*Am J Hum Genet.* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, have different population frequency in different populations, or are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will develop cardiac arrhythmia (e.g., atrial fibrillation or atrial flutter) and/or stroke. The variants described herein do however indicate increased and/or decreased likelihood that individuals carrying the at-risk or protective variants of the invention will develop symptoms associated with cardiac arrhythmia (e.g., atrial fibrillation or atrial flutter) and/or stroke. This information is however extremely valuable in itself, as outlined in more detail in the below, as it can be used to, for example, initiate preventive measures at an early stage, perform regular physical and/or mental exams to monitor the progress and/or appearance of symptoms, or to schedule exams at a regular interval to identify the condition in question, so as to be able to apply treatment at an early stage.

The knowledge about a genetic variant that confers a risk of developing cardiac arrhythmia (e.g., atrial fibrillation or atrial flutter) and/or stroke offers the opportunity to apply a genetic test to distinguish between individuals with increased risk of developing the disease (i.e. carriers of the at-risk variant) and those with decreased risk of developing the disease (i.e. carriers of the protective variant). The core values of genetic testing, for individuals belonging to both of the above mentioned groups, are the possibilities of being able to diagnose cardiac arrhythmia (e.g., atrial fibrillation or atrial flutter) and/or stroke, or a predisposition to cardiac arrhythmia (e.g., atrial fibrillation or atrial flutter) and/or stroke at an early stage and provide information to the clinician about prognosis of cardiac arrhythmia (e.g., atrial fibrillation or atrial flutter) and/or stroke in order to be able to apply the most appropriate treatment.

Individuals with a family history of cardiac arrhythmia (e.g., atrial fibrillation or atrial flutter) and/or stroke and carriers of at-risk variants may benefit from genetic testing since the knowledge of the presence of a genetic risk factor, or evidence for increased risk of being a carrier of one or more risk factors, may provide increased incentive for implementing a healthier lifestyle, by avoiding or minimizing known environmental risk factors for cardiovascular diseases related to cardiac arrhythmia (e.g., atrial fibrillation or atrial flutter) and/or stroke. Genetic testing of cardiac arrhythmia (e.g., atrial fibrillation or atrial flutter) and/or stroke patients may furthermore give valuable information about the primary cause of the disease and can aid the clinician in selecting the best treatment options and medication for each individual.

The present invention furthermore relates to risk assessment for cardiac arrhythmia (e.g., atrial fibrillation or atrial flutter) and/or stroke, including determining whether an individual is at risk for developing cardiac arrhythmia (e.g., atrial fibrillation or atrial flutter) and/or stroke. The polymorphic markers of the present invention can be used alone or in combination, as well as in combination with other factors, including other genetic risk factors or biomarkers, for risk assessment of an individual for cardiac arrhythmia (e.g., atrial fibrillation or atrial flutter) and/or stroke. Many factors known to affect the predisposition of an individual towards developing risk of cardiovascular disease are susceptibility factors for cardiac arrhythmias (e.g., atrial fibrillation or atrial flutter) and/or stroke, and are known to the person skilled in the art and can be utilized in such assessment. These include, but are not limited to, age, gender, smoking status, physical activity, waist-to-hip circumference ratio, family history of cardiac arrhythmia (in particular atrial fibrillation and/or atrial flutter) and/or stroke, previously diagnosed cardiac arrhythmia (e.g., atrial fibrillation or atrial flutter) and/or stroke, obesity, hypertriglyceridemia, low HDL cholesterol, hypertension, elevated blood pressure, cholesterol levels, HDL cholesterol, LDL cholesterol, triglycerides, apolipoprotein AI and B levels, fibrinogen, ferritin, C-reactive protein and leukotriene levels. Particular biomarkers that have been associated with Atrial fibrillation/Atrial flutter and stroke are discussed in Allard et al. (*Clin Chem* 51:2043-2051 (2005) and Becker (*J Thromb Thrombolys* 19:71-75 (2005)). These include, but are not limited to, fibrin D-dimer, prothrombin activation fragment 1.2 (F1.2), thrombin-antithrombin III complexes (TAT), fibrinopeptide A (FPA), lipoprotein-associated phospholipase A2 (Ip-PLA2), beta-thromboglobulin, platelet factor 4, P-selectin, von Willebrand Factor, pro-natriuretic peptide (BNP), matrix metalloproteinase-9 (MMP-9), PARK7, nucleoside diphosphate kinase (NDKA), tau, neuron-specific enolase, B-type neurotrophic growth factor, astroglial protein S-100b, glial fibrillary acidic protein, C-reactive protein, seum amyloid A, marix metalloproteinase-9, vascular and intracellular cell adhesion molecules, tumor necrosis factor alpha, and interleukins, including interleukin-1, -6, and -8). Circulating progenitor cells have also been implicated as being useful biomarkers for AF. In particular embodiments, more than one biomarker is determined for an individual, and combined with results of a determination of at least one polymorphic marker as described herein. Preferably, biomarker is measured in plasma or serum from the individual. Alternatively, the biomarker is determined in other suitable tissues containing measurable amounts of the biomarker, and such embodiments are also within scope of the invention.

Methods known in the art can be used for overall risk assessment, including multivariate analyses or logistic regression.

Atrial fibrillation is a disease of great significance both to the individual patient and to the health care system as a whole. It can be a permanent condition but may also be paroxysmal and recurrent in which case it can be very challenging to diagnose. The most devastating complication of atrial fibrillation and atrial flutter is the occurrence of debilitating stroke.

Importantly the risk of stroke is equal in permanent and paroxysmal atrial fibrillation. It has repeatedly been shown that therapy with warfarin anticoagulation can significantly reduce the risk of first or further episodes of stroke in the setting of atrial fibrillation. Therefore, anticoagulation with warfarin is standard therapy for almost all patients with atrial fibrillation for stroke-prevention, whether they have the permanent or paroxysmal type. The only patients for whom warfarin is not strongly recommended are those younger than 65 years old who are considered low-risk, i.e., they have no organic heart disease, including, neither hypertension no coronary artery disease, no previous history of stroke or transient ischemic attacks and no diabetes. This group has a lower risk of stroke and stroke-prevention with aspirin is recommended.

Due to the nature of paroxysmal atrial fibrillation it can be very difficult to diagnose. When the patient seeks medical attention due to disease-related symptoms, such as palpitations, chest pain, shortness of breath, dizziness, heart failure, transient ischemic attacks or even stroke, normal heart rhythm may already be restored precluding diagnosis of the arrhythmia. In these cases cardiac rhythm monitoring is frequently applied in the attempt to diagnose the condition. The cardiac rhythm is commonly monitored continuously for 24 to 48 hours. Unfortunately atrial fibrillation episodes are unpredictable and frequently missed by this approach. The opportunity to diagnose the arrhythmia, institute recommended therapy, and possibly prevent a debilitating first or recurrent stroke may be missed with devastating results to the patient. Prolonged and more complex cardiac rhythm monitoring measures are available and applied occasionally when the suspicion of atrial fibrillation is very strong. These tests are expensive, the diagnostic yield with current approach is often low, and they are used sparingly for this indication. In these circumstances additional risk stratification with genetic testing may be extremely helpful. Understanding that the individual in question carries either an at-risk or a protective genetic variant can be an invaluable contribution to diagnostic and/or treatment decision making. This way, in some cases, unnecessary testing and therapy may be avoided, and in other cases, with the help of more aggressive diagnostic approach, the arrhythmia may be diagnosed and/or proper therapy initiated and later complications of disease diminished.

How Genetic Testing May Directly Affect Choice of Treatment

When individuals present with their first (diagnosed) episode of paroxysmal atrial fibrillation and either spontaneously convert to sinus rhythm or undergo electrical or chemical cardioversion less than 48 hours into the episode, the decision to initiate, or not to initiate, anticoagulation therapy, is individualized based on the risk profile of the patient in question and the managing physicians preference. This can be a difficult choice to make since committing the patient to anticoagulation therapy has a major impact on the patients life.

Often the choice is made to withhold anticoagulation in such a situation and this may be of no significant consequence to the patient. On the other hand the patient may later develop a stroke and the opportunity of prevention may thus have been missed. In such circumstances, knowing that the patient is a carrier of the at-risk variant may be of great significance and support initiation of anticoagulation treatment.

Individuals who are diagnosed with atrial fibrillation under the age of 65 and are otherwise considered low risk for stroke, i.e. have no organic heart disease, no hypertension, no diabetes and no previous history of stroke, are generally treated with aspirin only for stroke-prevention and not anticoagulation. If such a patient is found to be carrier for the at-risk variants described herein, this could be considered support for initiating anticoagulation earlier than otherwise recommended. This would be a reasonable consideration since the results of stroke from atrial fibrillation can be devastating.

Ischemic stroke is generally classified into five subtypes based on suspected cause; large artery atherosclerosis, small artery occlusion, cardioembolism (majority due to atrial fibrillation), stroke of other determined cause and stroke of undetermined cause (either no cause found or more than 1 plausible cause). Importantly, strokes due to cardioembolism have the highest recurrence, are most disabling and are associated with the lowest survival. It is therefore imperative not to overlook atrial fibrillation as the major cause of stroke, particularly since treatment measures vary based on the subtype. Therefore, if an individual is diagnosed with stroke or a transient ischemic attack and a plausible cause is not identified despite standard work-up, knowing that the patient is a carrier of the at-risk variant may be of great value and support either initiation of anticoagulation treatment or more aggressive diagnostic testing in the attempt to diagnose atrial fibrillation.

Furthermore, the markers of the present invention can be used to increase power and effectiveness of clinical trials. Thus, individuals who are carriers of at least one at-risk variant of the present invention, i.e. individuals who are carriers of at least one allele of at least one polymorphic marker conferring increased risk of developing cardiac arrhythmia (e.g., atrial fibrillation or atrial flutter) and/or stroke may be more likely to respond to a particular treatment modality, e.g., as described in the above. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain sub-group of the population. Thus, one possible outcome of such a trial is that carriers of certain genetic variants, e.g., the markers and haplotypes of the present invention, are statistically significantly likely to show positive response to the therapeutic agent, i.e. experience alleviation of symptoms associated with cardiac arrhythmia (e.g., atrial fibrillation or atrial flutter) and/or stroke when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of the two, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Diagnostic and Screening Methods

In certain embodiments, the present invention pertains to methods of diagnosing, or aiding in the diagnosis of, certain conditions, including cardiac arrhythmia (atrial fibrillation, atrial flutter) and stroke. In other embodiments, the invention pertains to methods of determining a susceptibility to one or more of these conditions, by detecting particular alleles at genetic markers that appear more frequently in subjects with these conditions or subjects who are susceptible to these conditions. In particular embodiments, the invention comprises detecting the presence or absence of at least one allele of at least one polymorphic marker (e.g., the markers described herein). The present invention describes methods whereby detection of particular alleles of particular markers or haplotypes is indicative of a susceptibility to one or more of these conditions. Such prognostic or predictive assays can also be useful to determine suitable prophylactic treatment of a subject, or for selection of individuals for whom particular treatment is suitable The present invention pertains in some embodiments to methods of clinical applications of diagnosis, e.g., diagnosis performed by a medical professional. In other embodiments, the invention pertains to methods of diagnosis or determination of a susceptibility performed by a layman. The layman can be the customer of a genotyping or genetic health service. The layman may also be a genotype or genetic health service provider, who performs genotype analysis on a DNA sample from an individual, or a dataset comprising genotype information, in order to provide service related to genetic risk factors for particular traits or diseases, based on the genotype status of the individual (i.e., the customer). Recent technological advances in genotyping technologies, including high-throughput genotyping of SNP markers, such as Molecular Inversion Probe array technology (e.g., Affymetrix GeneChip), and BeadArray Technologies (e.g., Illumine GoldenGate and Infinium assays) have made it possible for individuals to have their own genome assessed for up to one million SNPs simultaneously, at relatively little cost. The resulting genotype information, which can be made available to the individual, can be compared to information about disease or trait risk associated with various SNPs, including information from public literature and scientific publications. The diagnostic application of disease-associated alleles as described herein, can thus for example be performed by the individual, through analysis of his/her genotype data, by a health professional based on results of a clinical test, or by a third party, including the genotype service provider. The third party may also be service provider (e.g., a genetic health service provider) who interprets genotype information from the customer to provide service related to specific genetic risk factors, including the genetic markers described herein. In other words, the diagnosis or determination of a susceptibility of genetic risk can be made by health professionals, genetic counselors, third parties providing genotyping service, third parties providing risk assessment service or by the layman (e.g., the individual), based on information about the genotype status of an individual and knowledge about the risk conferred by particular genetic risk factors (e.g., particular SNPs). In the present context, the term "diagnosing", "diagnose a susceptibility" and "determine a susceptibility" is meant to refer to any available diagnostic method, including those mentioned above.

In certain embodiments, a sample containing genomic DNA from an individual is collected. Such sample can for example be a buccal swab, a saliva sample, a blood sample, or other suitable samples containing genomic DNA, as described further herein. In certain embodiments, the sample is obtained by non-invasive means (e.g., for obtaining a buccal sample, saliva sample, hair sample or skin sample). In certain embodiments, the sample is obtained by non-surgical means, i.e. in the absence of a surgical intervention on the individual that puts the individual at substantial health risk. Such embodiments may, in addition to non-invasive means also include obtaining sample by extracting a blood sample (e.g., a venous blood sample). The genomic DNA obtained from the individual is then analyzed using any common technique available to the skilled person, such as high-throughput array technologies. Results from such genotyping are stored in a convenient data storage unit, such as a data carrier, including computer databases, data storage disks, or by other convenient data storage means. In certain embodiments, the computer database is an object database, a relational database or a post-relational database. The genotype data is subsequently analyzed for the presence of certain variants known to be susceptibility variants for a particular human condition, such as the genetic variants described herein. Genotype data can be retrieved from the data storage unit using any convenient data query method. Calculating risk conferred by a particular genotype for the individual can be based on comparing the genotype of the individual to previously determined risk (expressed as a relative risk (RR) or and odds ratio (OR), for example) for the genotype, for example for an heterozygous carrier of an at-risk variant for a particular disease or trait (such as atrial fibrillation, atrial flutter and/or stroke). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. Using the population average may in certain embodiments be more convenient, since it provides a measure which is easy to interpret for the user, i.e. a measure that gives the risk for the individual, based on his/her genotype, compared with the average in the population. The calculated risk estimated can be made available to the customer via a website, preferably a secure website.

In certain embodiments, a service provider will include in the provided service all of the steps of isolating genomic DNA from a sample provided by the customer, performing genotyping of the isolated DNA, calculating genetic risk based on the genotype data, and report the risk to the customer. In some other embodiments, the service provider will include in the service the interpretation of genotype data for the individual, i.e., risk estimates for particular genetic variants based on the genotype data for the individual. In some other embodiments, the service provider may include service that includes genotyping service and interpretation of the genotype data, starting from a sample of isolated DNA from the individual (the customer).

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

In addition, in certain other embodiments, the present invention pertains to methods of determining a decreased susceptibility to a condition selected from the group consisting of cardiac arrhythmia (e.g., atrial fibrillation, atrial flutter) and stroke, by detecting particular genetic marker alleles or haplotypes that appear less frequently in individuals with these conditions than in individual that do not have these conditions, or in the general population.

As described and exemplified herein, particular marker alleles are associated with atrial fibrillation, atrial flutter and stroke. In one embodiment, the marker allele or haplotype is one that confers a significant risk or susceptibility to these conditions. In another embodiment, the invention relates to a method of determining a susceptibility to atrial fibrillation, atrial flutter and/or stroke in a human individual, the method comprising determining the presence or absence of at least one allele of at least one polymorphic marker in a nucleic acid sample obtained from the individual, wherein the at least one polymorphic marker is selected from the group consisting of the polymorphic markers rs7193343, rs7618072, rs10077199, rs10490066, rs10516002, rs10519674, rs1394796, rs2935888, rs4560443, rs6010770 and rs7733337, and markers in linkage disequilibrium therewith. In a preferred embodiment, the at least one marker is selected from the group consisting of rs7193343, and markers in linkage disequilibrium therewith. In another embodiment, the invention pertains to methods of determining a susceptibility to atrial fibrillation, atrial flutter and/or stroke in a human individual, by screening for at least one marker allele selected from the group consisting of the T allele of rs7193343, the T allele of rs7618072, the T allele of rs10077199, the A allele of rs10490066, the A allele of rs10516002, the G allele of rs10519674, the C allele of rs1394796, the T allele of rs2935888, the T allele of rs4560443, the G allele of rs6010770 and the T allele of rs7733337, and marker alleles in linkage disequilibrium therewith. In a preferred embodiment, the marker allele is selected from the group consisting of rs7193343, and marker alleles in linkage disequilibrium therewith. In another embodiment, the marker allele or haplotype is more frequently present in a subject having, or who is susceptible to, atrial fibrillation, atrial flutter and/or stroke (affected), as compared to the frequency of its presence in a healthy subject (control, such as population controls). In certain embodiments, the significance of association of the at least one marker allele or haplotype is characterized by a p value<0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to atrial fibrillation, atrial flutter and/or stroke. These diagnostic methods involve determining whether particular alleles or haplotypes that are associated with risk of these conditions are present in particular individuals. The haplotypes described herein include combinations of alleles at various genetic markers (e.g., SNPs, microsatellites or other genetic variants). The detection of the particular genetic marker alleles that make up particular haplotypes can be performed by a variety of methods described herein and/or known in the art. For example, genetic markers can be detected at the nucleic acid level (e.g., by direct nucleotide sequencing, or by other genotyping means known to the skilled in the art) or at the amino acid level if the genetic marker affects the coding sequence of a protein (e.g., by protein sequencing or by immunoassays using antibodies that recognize such a protein). The marker alleles or haplotypes of the present invention correspond to fragments of a genomic segments (e.g., genes) associated with atrial fibrillation, atrial flutter and/or stroke. Such fragments encompass the DNA sequence of the polymorphic marker or haplotype in question, but may also include DNA segments in strong LD (linkage disequilibrium) with the marker or haplotype. In one embodiment, such segments comprises segments in LD with the marker or haplotype as determined by a value of $r^2$ greater than 0.2 and/or |D'|>0.8).

In one embodiment, determination of a susceptibility can be accomplished using hybridization methods. (see Current Protocols in Molecular Biology, Ausubel, F. et al., eds., John Wiley & Sons, including all supplements). The presence of a specific marker allele can be indicated by sequence-specific hybridization of a nucleic acid probe specific for the particular allele. The presence of more than one specific marker allele or a specific haplotype can be indicated by using several sequence-specific nucleic acid probes, each being specific for a particular allele. A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample. The invention can also be reduced to practice using any convenient genotyping method, including commercially available technologies and methods for genotyping particular polymorphic markers.

To determine a susceptibility, a hybridization sample can be formed by contacting the test sample containing a nucleic acid, such as a genomic dna sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of the nucleotide sequence of LD Block C16, optionally comprising at least one allele of a marker described herein, or the nucleic acid probe can comprise all or a portion of the nucleotide sequence of any one of the markers rs16971447, rs16971471, rs7193343, rs719353, rs719354, rs2106261, rs1548374, rs879324, rs8057081, rs12932445 and rs9940321 as described herein, or the probe can be the complementary sequence of such a sequence. In a particular embodiment, the nucleic acid probe is a portion of the nucleotide sequence of LD Block C16, as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular genetic composition (i.e., a particular haplotype, which may be tagged by one or many tagging markers).

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

Alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with atrial fibrillation, atrial flutter and stroke. Hybridization of the PNA probe is thus diagnostic for these conditions.

In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis, for example by using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s). Further, the expression of the variant(s) can be quantified as physically or functionally different.

In another embodiment of the methods of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes. Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid that contains a polymorphic marker or haplotype, and the presence of specific alleles can then be detected directly by sequencing the polymorphic site (or multiple polymorphic sites in a haplotype) of the genomic DNA in the sample.

In another embodiment, arrays of oligonucleotide probes that are complementary to target nucleic acid sequence segments from a subject, can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Bier, F. F., et al. *Adv Biochem Eng Biotechnol* 109:433-53 (2008); Hoheisel, J. D., *Nat Rev Genet.* 7:200-10 (2006); Fan, J. B., et al. *Methods Enzymol* 410:57-73 (2006); Raqoussis, J. & Elvidge, G., *Expert Rev Mol Diagn* 6:145-52 (2006); Mockler, T. C., et al *Genomics* 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. No. 6,858,394, U.S. Pat. No. 6,429,027, U.S. Pat. No. 5,445,934, U.S. Pat. No. 5,700,637, U.S. Pat. No. 5,744,305, U.S. Pat. No. 5,945,334, U.S. Pat. No. 6,054,270, U.S. Pat. No. 6,300,063, U.S. Pat. No. 6,733,977, U.S. Pat. No. 7,364,858, EP 619 321, and EP 373 203, the entire teachings of which are incorporated by reference herein.

Other methods of nucleic acid analysis that are available to those skilled in the art can be used to detect a particular allele at a polymorphic site. Representative methods include, for example, direct manual sequencing (Church and Gilbert, *Proc. Natl. Acad. Sci. USA,* 81: 1991-1995 (1988); Sanger, F., et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA,* 86:232-236 (1989)), mobility shift analysis (Orita, M., et al., *Proc. Natl. Acad. Sci. USA,* 86:2766-2770 (1989)), restriction enzyme analysis (Flavell, R., et al., *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize nucleotide mismatches, such as *E. coli* mutS protein; and allele-specific PCR.

In another embodiment of the invention, determination of a susceptibility can be made by examining expression and/or composition of a polypeptide encoded by a nucleic acid associated with a condition selected from the group consisting of atrial fibrillation, atrial flutter and/or stroke in those instances where the genetic marker(s) or haplotype(s) of the present invention result in a change in the composition or expression of the polypeptide. In one such embodiment, the polypeptide is a ZFHX3 polypeptide. Thus, determination of a susceptibility to the condition can be made by examining expression and/or composition of one of these polypeptides, or another polypeptide encoded by a nucleic acid associated with the condition, in those instances where the genetic marker or haplotype of the present invention results in a change in the composition or expression of the polypeptide. The markers of the present invention that show association to the condition may play a role through their effect on one or more of such nearby genes (e.g., ZFHX3). Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) presented herein affect the expression of a nearby gene. In one embodiment, the gene is the ZFHX3 gene. It is well known that regulatory element affecting gene expression may be located far away, even as far as tenths or hundreds of kilobases away, from the promoter region of a gene. By assaying for the presence or absence of at least one allele of at least one polymorphic marker of the present invention, it is thus possible to assess the expression level of such nearby genes. It is thus contemplated that the detection of the markers or haplotypes of the present invention can be used for assessing expression for one or more of such genes.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a particular nucleic acid. An alteration in expression of a polypeptide encoded by the nucleic acid can be, for example, an alteration in the quantitative polypeptide expression (i.e., the amount of polypeptide produced). An alteration in the composition of a polypeptide encoded by the nucleic acid is an alteration in the qualitative polypeptide expression (e.g., expression of a mutant polypeptide or of a different splicing variant). In one embodiment, diagnosis of a susceptibility is made by detecting a particular splicing variant, or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, atrial fibrillation, atrial flutter and/or stroke. In one embodiment, the control sample is from a subject that does not possess a marker allele or haplotype associated with these conditions, as described herein. Similarly, the presence of one or more different splicing variants in the test sample, or the presence of significantly different amounts of different splicing variants in the test sample, as compared with the control sample, can be indicative of a susceptibility to the condition. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with the condition can be used (e.g., an antibody against a ZFHX3 protein or a fragment thereof). Antibodies can be polyclonal or monoclonal. An intact antibody, or a fragment thereof (e.g., Fv, Fab, Fab', F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of a polypeptide in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, determination of a susceptibility to atrial fibrillation, atrial flutter and/or stroke is made by detecting at least one marker or haplotype of the present invention, in combination with an additional protein-based, RNA-based or DNA-based assay.

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid, means for analyzing the nucleic acid sequence of a nucleic acid, means for analyzing the amino acid sequence of a polypeptide encoded by a nucleic acid as described herein, etc. The kits can for example include necessary buffers, nucleic acid primers for amplifying nucleic acids of the invention (e.g., a nucleic acid segment comprising one or more of the polymorphic markers as described herein), and reagents for allele-specific detection of the fragments amplified using such primers and necessary enzymes (e.g., dna polymerase). Additionally, kits can provide reagents for assays to be used in combination with the methods of the present invention, e.g., reagents for use with other diagnostic assays for atrial fibrillation, atrial flutter and/or stroke.

In one embodiment, the invention pertains to a kit for assaying a sample from a subject to detect a susceptibility to a condition selected from the group consisting of atrial fibrillation, atrial flutter and stroke in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism associated with disease risk. In one such embodiment, the polymorphism is selected from the group consisting of rs7193343, rs7618072, rs10077199, rs10490066, rs10516002, rs10519674, rs1394796, rs2935888, rs4560443, rs6010770 and rs7733337, and markers in linkage disequilibirium therewith. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are associated with risk of the condition.

In another embodiment, the kit comprises one or more labeled nucleic acids capable of allele-specific detection of one or more specific polymorphic markers or haplotypes, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers rs7193343, rs7618072, rs10077199, rs10490066, rs10516002, rs10519674, rs1394796, rs2935888, rs4560443, rs6010770 and rs7733337, and markers in linkage disequilibrium therewith. In another embodiment, the marker or haplotype to be detected comprises one or more markers, two or more markers, three or more markers, four or more markers or five or more markers selected from the group consisting of rs7193343, and markers in linkage disequilibrium therewith. In one embodiment, the marker or haplotype to be detected comprises one or more markers, two or more markers, three or more markers, four or more markers or five or more markers selected from the group consisting of rs16971447, rs16971471, rs719353, rs719354, rs2106261, rs1548374, rs879324, rs8057081, rs12932445, and rs9940321.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. As explained in the above, the detection oligonucleotide probe comprises a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe.

The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

In one embodiment, the DNA template is amplified by means of Whole Genome Amplification (WGA) methods, prior to assessment for the presence of specific polymorphic markers as described herein. Standard methods well known to the skilled person for performing WGA may be utilized, and are within scope of the invention. In one such embodiment, reagents for performing WGA are included in the reagent kit.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one embodiment, determination of the presence of a particular marker allele or haplotype is indicative of a susceptibility (increased susceptibility or decreased susceptibility) to atrial fibrillation, atrial flutter and/or stroke. In another embodiment, determination of the presence of the marker allele or haplotype is indicative of response to a therapeutic agent for atrial fibrillation, atrial flutter and/or stroke. In another embodiment, the presence of the marker allele or haplotype is indicative of prognosis of atrial fibrillation, atrial flutter and/or stroke. In yet another embodiment, the presence of the marker or haplotype is indicative of progress of treatment of a condition selected from atrial fibrillation, atrial flutter and/or stroke. Such treatment may include intervention by surgery, medication or by other means (e.g., lifestyle changes).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or rnai molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit. In certain embodiments, the kit further comprises a collection of data comprising correlation data between the polymorphic markers assessed by the kit and susceptibility to prostate cancer and/or colorectal cancer.

Therapeutic Agents

Treatment of Atrial Fibrillation and Atrial flutter is generally directed by two main objectives: (i) to prevent stroke and (ii) to treat symptoms.

(i) Stroke Prevention

Anticoagulation is the therapy of choice for stroke prevention in atrial fibrillation and is indicated for the majority of patients with this arrhythmia. The only patients for whom anticoagulation is not strongly recommended are those younger than 65 years old who are considered low-risk, i.e., they have no organic heart disease, no hypertension, no previous history of stroke or transient ischemic attacks and no diabetes. This group as a whole has a lower risk of stroke and stroke prevention with aspirin is generally recommended. For all other patients, anticoagulation is indicated whether the atrial fibrillation is permanent, recurrent paroxysmal or recurrent persistent. It cannot be generalized how patients who present with their first episode of paroxysmal atrial fibrillation should be treated and the decision needs to be individualized for each patient. Anticoagulation is also indicated even when the patient with atrial fibrillation is felt to be maintained in sinus rhythm with antiarrhythmic therapy (rhythm controlled) since this type of therapy does not affect stroke risk.

Anticoagulants. Anticoagulation is recommended in atrial fibrillation, as detailed above, for prevention of cardioembolism and stroke. The most widely studied oral anticoagulant is warfarin and this medication is universally recommended for chronic oral anticoagulation in atrial fibrillation. Warfarin has few side effects aside from the risk of bleeding but requires regular and careful monitoring of blood values during therapy (to measure the effect of the anticoagulation). The oral anticoagulant ximelagatran showed promise in stroke prevention in patients with atrial fibrillation and had the advantage of not requiring regular monitoring like warfarin. Ximelagatran was found however to cause unexplained liver injury and was withdrawn from the market in 2006. Several agents are available for intravenous and/or subcutaneous therapy, including heparin and the low molecular weight heparins (e.g. enoxaparin, dalteparin, tinzaparin, ardeparin, nadroparin and reviparin). These medications are recommended when rapid initiation of anticoagulation is necessary or if oral anticoagulation therapy has to be interrupted in high risk patients or for longer than one week in other patients for example due to a series of procedures. Other parenteral anticoagulants are available but not specifically recommended as therapy in atrial fibrillation; e.g., the factor Xa inhibitors fondaparinux and idraparinux, the thrombin-inhibitors lepirudin, bivalirudin and argatroban as well as danaparoid.

(ii) Symptom Control. Medical and surgical therapy applied to control symptoms of atrial fibrillation is tailored to the individual patient and consists of heart rate and/or rhythm control with medications, radiofrequency ablation and/or surgery.

Antiarrhythmic medications. In general terms, antiarrhythmic agents are used to suppress abnormal rhythms of the heart that are characteristic of cardiac arrhythmias, including atrial fibrillation and atrial flutter. One classification of antiarrhythmic agents is the Vaughan Williams classification, in which five main categories of antiarrhythmic agents are defined.

Class I agents are fast sodium channel blockers and are subclassified based on kinetics and strength of blockade as well as their effect on repolarization. Class Ia includes disopyramide, moricizine, procainamide and quinidine. Class Ib agents are lidocaine, mexiletine, tocamide, and phenyloin. Class Ic agents are encamide, flecamide, propafenone, ajmaline, cibenzoline and detajmium. Class II agents are beta blockers, they block the effects of catecholamines at beta-adrenergic receptors. Examples of beta blockers are esmolol, propranolol, metoprolol, alprenolol, atenolol, carvedilol, bisoprolol, acebutolol, nadolol, pindolol, labetalol, oxprenotol, penbutolol, timolol, betaxolol, cartelol, sotalol and levobunolol. Class III agents have mixed properties but are collectively potassium channel blockers and prolong repolarization. Medications in this category are amiodarone, azimilide, bretylium, dofetilide, tedisamil, ibutilide, sematilide, sotalol, N-acetyl procainamide, nifekalant hydrochloride, vernakalant and ambasilide. Class IV agents are calcium channel blockers and include verapamil, mibefradil and diltiazem. Finally, class V consists of miscellaneous antiarrhythmics and includes digoxin and adenosine.

Heart rate control, Pharmacologic measures for maintenance of heart rate control include beta blockers, calcium channel blockers and digoxin. All these medications slow the electrical conduction through the atrioventricular node and slow the ventricular rate response to the rapid atrial fibrillation. Some antiarrhythmics used primarily for rhythm control (see below) also slow the atrioventricular node conduction rate and thus the ventricular heart rate response. These include some class III and Ic medications such as amiodarone, sotalol and flecamide.

Cardioversion. Cardioversion of the heart rhythm from atrial fibrillation or atrial flutter to sinus rhythm can be achieved electrically, with synchronized direct-current cardioversion, or with medications such as ibutilide, amiodarone, procainamide, propafenone and flecamide.

Heart Rhythm Control

Medications used for maintenance of sinus rhythm, i.e. rhythm control, include mainly antiarrhythmic medications from classes III, Ia and Ic. Examples are sotalol, amiodarone and dofetilide from class III, disopyramide, procainamide and quinidine from class Ia and flecinide and propafenone from class Ic. Treatment with these antiarrhythmic medications is complicated, can be hazardous, and should be directed by physicians specifically trained to use these medications. Many of the antiarrhythmics have serious side effects and should only be used in specific populations. For example, class Ic medications should not be used in patients with coronary artery disease and even if they can suppress atrial fibrillation, they can actually promote rapid ventricular response in atrial flutter. Class Ia medications can be used as last resort in patients without structural heart diseases. Sotalol (as most class III antiarrhythmics) can cause significant prolongation of the QT interval, specifically in patients with renal failure, and promote serious ventricular arrhythmias. Both sotalol and dofetilide as well as the Ia medications need to be initiated on an inpatient basis to monitore the QT interval. Although amiodarone is usually well tolerated and is widely used, amiodarone has many serious side effects with long-term therapy.

The variants (markers and/or haplotypes) disclosed herein can also be useful for identifying novel therapeutic drug targets for atrial fibrillation, atrial flutter and/or stroke. For example, genes containing, or in linkage disequilibrium with, one or more of these variants (e.g., the ZFHX3 gene), or their products, as well as genes or their products that are directly or indirectly regulated by or interact with these variant genes or their products, can be targeted for the development of therapeutic agents to treat atrial fibrillation, atrial flutter and/or stroke, or prevent or delay onset of symptoms associated with any of these conditions. Therapeutic agents may comprise one or more of, for example, small non-protein and non-nucleic acid molecules, proteins, peptides, protein fragments, nucleic acids (dna, rna), pna (peptide nucleic acids), or their derivatives or mimetics which can modulate the function and/or levels of the target genes or their gene products.

The nucleic acids and/or variants described herein, or nucleic acids comprising their complementary sequence, may be used as antisense constructs to control gene expression in cells, tissues or organs. The methodology associated with antisense techniques is well known to the skilled artisan, and is for example described and reviewed in *AntisenseDrug Technology: Principles, Strategies, and Applications*, Crooke, ed., Marcel Dekker Inc., New York (2001). In general, antisense agents (antisense oligonucleotides) are comprised of single stranded oligonucleotides (RNA or DNA) that are capable of binding to a complimentary nucleotide segment. By binding the appropriate target sequence, an RNA-RNA, DNA-DNA or RNA-DNA duplex is formed. The antisense oligonucleotides are complementary to the sense or coding strand of a gene. It is also possible to form a triple helix, where the antisense oligonucleotide binds to duplex DNA.

Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today*, 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, Eur. *J. Biochem.* 270:1628-44 (2003), Dias et al., *Mol. Cancer. Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002).

In certain embodiments, the antisense agent is an oligonucleotide that is capable of binding to a nucleotide segment of the ZFHX3 gene. Antisense nucleotides can be from 5-500 nucleotides in length, including 5-200 nucleotides, 5-100 nucleotides, 10-50 nucleotides, and 10-30 nucleotides. In certain preferred embodiments, the antisense nucleotide is from 14-50 nucleotides in length, including 14-40 nucleotides and 14-30 nucleotides. In certain such embodiments, the antisense nucleotide is capable of binding to a nucleotide segment of the ZFHX3 gene. In certain embodiments, the antisense nucleotide comprises at least one polymorphic marker disclosed herein, e.g. a polymorphic marker selected from the group consisting of rs7193343, rs7618072, rs10077199, rs10490066, rs10516002, rs10519674, rs1394796, rs2935888, rs4560443, rs6010770 and rs7733337, and markers in linkage disequilibrium therewith Thus, the variants described herein can also be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule. As antisense molecules can be used to inactivate mRNA so as to inhibit gene expression, and thus protein expression, the molecules can be used for atrial fibrillation and/or stroke treatment. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in C. elegans (Fire et al., Nature 391:806-11 (1998)), and in recent years its potential use in treatment of human atrial fibrillation and/or stroke has been actively pursued (reviewed in Kim & Rossi, Nature Rev. Genet. 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, Drug Discovery Today, 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, Nature Rev. Genet. 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (FEBS Lett. 579:5974-81 (2005)). Chemically synthetic siRNAs and shRNAs are substrates for in vivo processing, and in some cases provide more potent gene-silencing than shorter designs (Kim et al., Nature Biotechnol. 23:222-226 (2005); Siolas et al., Nature Biotechnol. 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., Nature Biotechnol. 23:559-565 (2006); Brummelkamp et al., Science 296: 550-553 (2002)).

Since RNAi molecules, including siRNA, miRNA and shRNA, act in a sequence-dependent manner, the variants presented herein can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off atrial fibrillation and/or stroke-associated genes or atrial fibrillation and/or stroke-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, Nat. Rev. Genet. 8:173-184 (2007), Chen & Rajewsky, Nat. Rev. Genet. 8: 93-103 (2007), Reynolds, et al., Nat. Biotechnol. 22:326-330 (2004), Chi et al., Proc. Natl. Acad. Sci. USA 100:6343-6346 (2003), Vickers et al., J. Biol. Chem. 278:7108-7118 (2003), Agami, Curr. Opin. Chem. Biol. 6:829-834 (2002), Layery, et al., Curr. Opin. Drug Discov. Devel. 6:561-569 (2003), Shi, Trends Genet. 19:9-12 (2003), Shuey et al., Drug Discov. Today 7:1040-46 (2002), McManus et al., Nat. Rev. Genet. 3:737-747 (2002), Xia et al., Nat. Biotechnol. 20:1006-10 (2002), Plasterk et al., curr. Opin. Genet. Dev. 10:562-7 (2000), Bosher et al., Nat. Cell Biol. 2:E31-6 (2000), and Hunter, Curr. Biol. 9: R440-442 (1999).

A genetic defect leading to increased predisposition or risk for development of a disease, such as atrial fibrillation, atrial flutter and/or stroke, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the adminstered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat atrial fibrillation, atrial flutter and/or stroke. Thus, the variants of the invention are useful as targets for the identification and/or development of therapeutic agents. In certain embodiments, such methods include assaying the ability of an agent or compound to modulate the activity and/or expression of a nucleic acid that includes at least one of the variants (markers and/or haplotypes) of the present invention, or the encoded product of the nucleic acid. In certain embodiments, the nucleic acid is a ZFHX3 nucleic acid. This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating a condition selected from the group consisting of atrial fibrillation, atrial flutter and stroke can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods of Treatment As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different response, e.g. a different response rate, to a particular treatment modality. This means that a patient diagnosed with a condition selected from the group consisting of atrial fibrillation, atrial flutter and stroke, and carrying a certain allele at a polymorphic or haplotype of the present invention (e.g., the at-risk and protective alleles and/or haplotypes of the invention) would respond better to, or worse to, a specific therapeutic, drug and/or other therapy used to treat the condition. Therefore, the presence or absence of the marker allele or haplotype could aid in deciding what treatment should be used for a the patient. For example, for a newly diagnosed patient, the presence of a marker or haplotype of the present invention may be assessed (e.g., through testing DNA derived from a blood sample, as described herein). If the patient is positive for a marker allele or haplotype (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

Thus, the invention in certain aspects relates to a method of assessing probability of response of a human individual to a therapeutic agent for preventing, treating and/or ameliorating symptoms associated with a condition selected from the group consisting of: a cardiac arrhythmia selected from Atrial Fibriallation and Atrial Flutter, and Stroke, comprising obtaining sequence data about a human individual identifying at least one allele of at least one polymorphic marker selected from the group consisting of rs7193343, rs7618072, rs10077199, rs10490066, rs10516002, rs10519674, rs1394796, rs2935888, rs4560443, rs6010770 and rs7733337, and markers in linkage disequilibrium therewith, wherein different alleles of the at least one polymorphic marker are associated with different probabilities of response to the therapeutic agent in humans, and determining the probability of a positive response to the therapeutic agent from the sequence data.

In one embodiment, the therapeutic agent is selected from the group consisting of: an anticoagulant, an anti-arrhythmic agent, a hear rate control agent, a cardioversion agent, or a heart rhythm control agent. In another embodiment, the therapeutic agent is selected from the group consisting of warfarin, heparin, low molecular weight heparins, factor Xa inhibitors, and thrombin inhibitors, sodium channel blockers, beta blockers, potassium channel blockers, and calcium channel blockers.

In another embodiment, the therapeutic agent is selected from warfarin ((RS)-4-hydroxy-3-(3-oxo-1-phenylbutyl)-2H-chromen-2-one), ximelagatran (ethyl 2-[[(1R)-1-cyclohexyl-2-[(2S)-2-[[4-(N'-hydroxycarbamimidoyl) phenyl] methylcarbamoyl]azetidin-1-yl]-2-oxo-ethyl]amino] acetate), heparin, enoxaparin (LMW heparin), dalteparin, tinzaparin, ardeparin, nadroparin, reviparin, fondaparinux (a synthetic pentasaccharide; 2-deoxy-6-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-O-2-O-sulfo-α-L-idopyranouronosyl-(1→4)-O-methyl-2-deoxy-6-O-sulfo-2-(sulfoamino)-α-D-glucopyranoside, decasodium salt), idraparinux (Nonasodium (2S,3S,4S,5R,6R)-6-[(2R,3R,4S,5R,6R)-6-[(2R,3S,4S,5R,6R)-2-carboxylato-4,5-dimethoxy-6-[(2R,3R,4S,5R,6S)-6-methoxy-4,5-disulfonatooxy-2-(sulfonatooxymethyl)oxan-3-yl]oxyoxan-3-yl] oxy-4,5-disulfonatooxy-2-(sulfonatooxymethyl) oxan-3-yl] oxy-4,5-dimethoxy-3-[(2R,3R,4S,5R,6R)-3,4,5-trimethoxy-6-(sulfonatooxymethyl)oxan-2-yl]oxyoxane-2-carboxylate), lepirudin (direct thrombin inhibitor), bivalirudin ((15S,21S,24S,27S,30S)-15-(2-amino-2-oxoethyl)-1-[(2S)-1-{(2S)-2-[({(2S)-1-[(2R)-2-amino-3-phenylpropanoyl]pyrrolidin-2-yl}carbonyl)amino]-5-carbamimidamidopentanoyl}pyrrolidin-2-yl]-24-benzyl-30-({(2S,3S)-1-[(2S)-2-{[(2S)-4-carboxy-1-{[(2S)-4-carboxy-1-{[(2S)-1-{[(1S)-1-carboxy-3-methylbutyl]amino}-3-(4-hydroxyphenyl)-1-oxopropan-2-yl]amino}-1-oxobutan-2-yl]amino}-1-oxobutan-2-yl]carbamoyl]pyrroli\ndin-1-yl]-3-methyl-1-oxopentan-2-yl}carbamoyl)-27-(2-carboxyethyl)-21-(carboxymethyl)-1,4,7,10,13,16,19,22,25,28-decaoxo-2,5,8,11,14,17,20,23,26,29-decaazatritriacontan-33-oic acid), argatroban ((2R,4R)-1-[(2S)-5-(diaminomethylidene amino)-2-[[(3R)-3-methyl-1,2,3,4-tetrahydroquinolin-8-yl] sulfonylamino]pentanoyl]-4-methyl-piperidine-2-carboxylic acid), danaparoid (a derivative of heparine), disopyramide (4-(diisopropylamino)-2-phenyl-2-(pyridin-2-yl) butanamide), moricizine (ethyl[10-(3-morpholin-4-ylpropanoyl)-10H-phenothiazin-2-yl]carbamate), procainamide(4-amino-N-(2-diethylaminoethyl) benzamide), quinidine ((9S)-6'-methoxycinchonan-9-ol), lidocaine (2-(diethylamino)-N-(2,6-dimethylphenyl)acetamide), mexiletine (1-(2,6-dimethylphenoxy) propan-2-amine), tocainide (N-(2,6-dimethylphenyl)alaninamide), phenyloin (5,5-diphenylimidazolidine-2,4-dione), encainide (4-methoxy-N-{2-[1-(piperidin-1-yl)propan-2-yl] phenyl}benzamide), flecainide (N-(piperidin-2-ylmethyl)-2,5-bis(2,2,2-trifluoroethoxy) benzamide), propafenone (1-{2-[2-hydroxy-3-(propylamino)propoxy]phenyl}-3-phenylpropan-1-one), ajmaline ((1R,9R,10S,13R,14R,16S,18S)-13-ethyl-8-methyl-8,15-diazahexacyclo[14.2.1.0$^{1,9}$.0$^{2,7}$.0$^{12,17}$]nonadeca-2(7),3,5-triene-14,18-diol), cibenzoline (2-(2,2-diphenylcyclopropyl)-4,5-dihydro-1H-imidazole), detajmium (7-(3-(diethylamino)-2-hydroxypropyl)-17,21-dihydroxyajmalanium), esmolol (methyl 3-{4-[2-hydroxy-3-(propan-2-ylamino)propoxy]phenyl}propanoate), propranolol (2-hydroxy-3-(naphthalen-1-yloxy) propyl] (propan-2-yl) amine), metoprolol ({2-hydroxy-3-[4-(2-methoxyethyl) phenoxy]propyl}(propan-2-yl) amine), alprenolol ({2-hydroxy-3-[2-(prop-2-en-1-yl)phenoxy]propyl}(propan-2-yl) amine), atenolol (2-{4-[2-hydroxy-3-(propan-2-ylamino) propoxy]phenyl}acetamide), carvedilol ([3-(9H-carbazol-4-yloxy)-2-hydroxypropyl][2-(2-methoxyphenoxy)ethyl] amine), bisoprolol ([2-hydroxy-3-(4-{[2-(propan-2-yloxy) ethoxy]methyl}phenoxy)propyl](propan-2-yl)amine), acebutolol (N-{3-acetyl-4-[2-hydroxy-3-(propan-2-ylamino) propoxy]phenyl}butanamide), nadolol ((2R,3S)-5-[3-(tert-butylamino)-2-hydroxypropoxy]-1,2,3,4-tetrahydronaphthalene-2,3-diol), pindolol ([2-hydroxy-3-(1H-indol-4-yloxy)propyl](propan-2-yl)amine), labetalol (2-hydroxy-5-{1-hydroxy-2-[(4-phenylbutan-2-yl)amino] ethyl}benzamide), oxprenotol, penbutolol (1-(tert-butylamino)-3-(2-cyclopentylphenoxy)propan-2-ol), timolol ((2S)-1-(tert-butylamino)-3-[(4-morpholin-4-yl-1,2,5-thiadiazol-3-yl)oxy]propan-2-ol), betaxolol ((3-{4-[2-(cyclopropyl-methoxy)ethyl]phenoxy}-2-hydroxypropyl)(propan-2-yl)amine), carteolol (5-[3-(tert-butylamino)-2-hydroxypropoxy]-1,2,3,4-tetrahydroquinolin-2-one), sotalol (N-{4-[1-hydroxy-2-(propan-2-ylamino)ethyl] phenyl}methanesulfonamide), levobunolol (5-(2-hydroxy-3-tert-butylamino-propoxy)tetralin-1-one), amiodarone ((2-{4-[(2-butyl-1-benzofuran-3-yl)carbonyl]-2,6-diiodophenoxy}ethyl)diethylamine), azimilide (1-({(E)-[5-(4-chlorophenyl)furan-2-yl]methylidene}amino)-3-[4-(4-methylpiperazin-1-yl)butyl]imidazolidine-2,4-dione), bretylium ([(2-bromophenyl)methyl](ethyl)dimethylazanium), dofetilide (N-[4-(2-{[2-(4-methane-sulfonamidophenoxy)ethyl](methyl)amino}ethyl)phenyl]methanesulfonamide), tedisamil (3,7-bis(cyclopropylmethyl)-3,7-diazaspiro [bicyclo[3.3.1]nonane-9,1'-cyclopentane]), ibutilide (N-(4-{4-[ethyl(heptyl)amino]-1-hydroxybutyl}phenyl) methanesulfonamide), sematilide (N-(2-Diethylaminoethyl)-4-methanesulfonamidobenzamide), N-acetyl procainamide(4-acetylamino-N-(2-diethylaminoethyl)benzamide), nifekalant hydrochloride (6-[2-[N-(2-Hydroxyethyl)-3-(4-nitrophenyl)propylamino]ethylamino]-1,3-dimethyl-2,4 (1H,3H)-pyrimidinedione hydrochloride), vernakalant ((3R)-1-{(1R,2R)-2-[2-(3,4-dimethoxyphenyl) ethoxy] cyclohexyl}pyrrolidin-3-ol), ambasilide (3-(p-Aminobenzoyl)-7-benzyl-3,7-diazabicyclo(3.3.1)nonane), verapamil (2-(3,4-dimethoxyphenyl)-5-[2-(3,4-dimethoxyphenyl) ethyl-methyl-amino]-2-propan-2-yl-pentanenitrile), mibefradil ((1S,2S)-2-(2-((3-(1H-benzo[d]imidazol-2-yl)propyl) (methyl)amino)ethyl)-6-fluoro-1-isopropyl-1,2,3,4-tetrahydronaphthalen-2-yl 2-methoxyacetate), diltiazem ([2-(2-dimethylaminoethyl)-5-(4-methoxyphenyl)-3-oxo-6-thia-2-azabicyclo[5.4.0]undeca-7,9,11-trien-4-yl]ethanoate), digoxin (4-[(3S,5R,8R,9S,10S,12R,13S,14S)-3-[(2S,4S,5R,6R)-5-[(2S,4S,5R,6R)-5-[(2S,4S,5R,6R)-4,5-dihydroxy-6-methyl-oxan-2-yl]oxy-4-hydroxy-6-methyl-oxan-2-yl]oxy-4-hydroxy-6-methyl-oxan-2-yl]oxy-12,14-dihydroxy-10,13-dimethyl-1,2,3,4,5,6,7,8,9,11,12,15,16,17-tetradecahydrocyclopenta[a]phenanthren-17-yl]-5H-furan-2-one), adenosine ((2R,3R,4S,5R)-2-(6-amino-9H-purin-9-yl)-5-(hydroxymethyl)oxolane-3,4-diol), ibutilide (N-(4-{4-[ethyl(heptyl)amino]-1-hydroxybutyl}phenyl) methanesulfonamide), amiodarone ((2-{4-[(2-butyl-1-benzofuran-3-yl)carbonyl]-2,6-diiodophenoxy}ethyl) diethylamine), procainamide(4-amino-N-(2-diethylaminoethyl)benzamide), propafenone (1-{2-[2-hydroxy-3-(propylamino)propoxy]phenyl}-3-phenylpropan-1-one) and flecainide (N-(piperidin-2-ylmethyl)-2,5-bis(2,2,2-trifluoroethoxy)benzamide).

Yet another aspect of the invention relates to a method of predicting prognosis of an individual diagnosed with, a cardiac arrhythmia and/or stroke, the method comprising determining the presence or absence of at least one allele of at least one polymorphic marker in a nucleic acid sample obtained from the individual, wherein the at least one polymorphic marker is selected from the group consisting of rs7193343, rs7618072, rs10077199, rs10490066, rs10516002, rs10519674, rs1394796, rs2935888, rs4560443, rs6010770 and rs7733337, and markers in linkage disequilibrium therewith, wherein determination of the presence of the at least one allele is indicative of a worse prognosis of the cardiac arrhythmia and/or stroke in the individual.

Methods of monitoring progress of a treatment of an individual undergoing treatment for a cardiac arrhythmia (Atrial Fibrillation, Atrial Flutter) and/or stroke are also within scope of the invention, the methods comprising determining the presence or absence of at least one allele of at least one polymorphic marker in a nucleic acid sample obtained from the individual, wherein the at least one polymorphic marker is selected from the group consisting of rs7193343, rs7618072, rs10077199, rs10490066, rs10516002, rs10519674, rs1394796, rs2935888, rs4560443, rs6010770 and rs7733337, and markers in linkage disequilibrium therewith, wherein determination of the presence of the at least one allele is indicative of the treatment outcome of the individual.

The present invention also relates to methods of monitoring progress or effectiveness of a treatment for atrial fibrillation, atrial flutter and/or stroke. This can be done based on the genotype and/or haplotype status of the markers and haplotypes of the present invention, i.e., by assessing the absence or presence of at least one allele of at least one polymorphic marker as disclosed herein, or by monitoring expression of genes that are associated with the variants (markers and haplotypes) of the present invention. The risk gene mRNA or the encoded polypeptide can be measured in a tissue sample (e.g., a peripheral blood sample, or a biopsy sample). Expression levels and/or mrna levels can thus be determined before and during treatment to monitor its effectiveness. Alternatively, or concomitantly, the genotype and/or haplotype status of at least one risk variant as described herein is determined before and during treatment to monitor its effectiveness.

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway, in samples taken before and during treatment. Alternatively, metabolites belonging to the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of at least one at-risk variant of the present invention may be more likely to respond favorably to a particular treatment modality. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain subgroup of the population. Thus, one possible outcome of such a trial is that carriers of certain genetic variants, e.g., the markers and haplotypes of the present invention, are statistically significantly likely to show positive response to the therapeutic agent, i.e. experience alleviation of symptoms when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of lifestyle changes and administration of particular treatment, can be realized by the utilization of the at-risk variants of the present invention. Thus, the knowledge of an individual's status for particular markers of the present invention, can be useful for selection of treatment options that target genes or gene products affected by the at-risk variants of the invention. In certain embodiments, the gene or gene product is a ZFHX3 gene or its gene products. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

FIG. 1 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method or apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 1, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Although the forgoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

While the risk evaluation system and method, and other elements, have been described as preferably being implemented in software, they may be implemented in hardware, firmware, etc., and may be implemented by any other processor. Thus, the elements described herein may be implemented in a standard multi-purpose CPU or on specifically designed hardware or firmware such as an application-specific integrated circuit (ASIC) or other hard-wired device as desired, including, but not limited to, the computer 110 of FIG. 1. When implemented in software, the software routine may be stored in any computer readable memory such as on a magnetic disk, a laser disk, or other storage medium, in a RAM or ROM of a computer or processor, in any database, etc. Likewise, this software may be delivered to a user or a diagnostic system via any known or desired delivery method including, for example, on a computer readable disk or other transportable computer storage mechanism or over a communication channel such as a telephone line, the internet, wireless communication, etc. (which are viewed as being the same as or interchangeable with providing such software via a transportable storage medium).

Thus, many modifications and variations may be made in the techniques and structures described and illustrated herein without departing from the spirit and scope of the present invention. Thus, it should be understood that the methods and apparatus described herein are illustrative only and are not limiting upon the scope of the invention.

Accordingly, the invention relates to computer-implemented applications using the polymorphic markers and haplotypes described herein, and genotype and/or disease-association data derived therefrom. Such applications can be useful for storing, manipulating or otherwise analyzing genotype data that is useful in the methods of the invention. One example pertains to storing genotype information derived from an individual on readable media, so as to be able to provide the genotype information to a third party (e.g., the individual, a guardian of the individual, a health care provider or genetic analysis service provider), or for deriving information from the genotype data, e.g., by comparing the genotype data to information about genetic risk factors contributing to increased susceptibility to a condition selected from Atrial Fibrillation, Atrial Flutter and Stroke, and reporting results based on such comparison.

In certain embodiments, computer-readable media comprise capabilities of storing (i) identifier information for at least one polymorphic marker or a haplotype, as described herein; (ii) an indicator of the frequency (e.g., the presence or absence) of at least one allele of said at least one marker, or the frequency of a haplotype, in individuals with a particular condition or disease; and (iii) an indicator of the risk associated with the marker or haplotype (e.g., the risk conferred by particular alleles or haplotypes).

The markers and haplotypes described herein to be associated with increased susceptibility (e.g., increased risk) of conditions such as atrial fibrillation, atrial flutter and/or stroke, are in certain embodiments useful for interpretation and/or analysis of genotype data. thus in certain embodiments, an identification of an at-risk allele for these conditions, as shown herein, or an allele at a polymorphic marker in LD with any one of such markers is indicative of the individual from whom the genotype data originates is at increased risk of the condition. In one such embodiment, genotype data is generated for at least one polymorphic marker shown herein to be associated with atrial fibrillation, atrial flutter and/or stroke, or a marker in linkage disequilibrium therewith. The genotype data is subsequently made available to a third party, such as the individual from whom the data originates, his/her guardian or representative, a physician or health care worker, genetic counsellor, or insurance agent, for example via a user interface accessible over the internet, together with an interpretation of the genotype data, e.g., in the form of a risk measure (such as an absolute risk (AR), risk ratio (RR) or odds ratio (OR)) for the disease. In another embodiment, at-risk markers identified in a genotype dataset derived from an individual are assessed and results from the assessment of the risk conferred by the presence of such at-risk variants in the dataset are made available to the third party, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived.

Nucleic Acids and Polypeptides

The nucleic acids and polypeptides described herein can be used in methods and kits of the present invention. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.*, 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions×100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20). Another example of an algorithm is BLAT (Kent, W. J. *Genome Res.* 12:656-64 (2002)).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988).

In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of LD Block C16, or a nucleotide sequence comprising, or consisting of, the complement of the nucleotide sequence of LD Block C16, wherein the nucleotide sequence comprises at least one polymorphic allele contained in the markers and haplotypes described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radio labeled, fluorescently labeled) and used as a probe for screening a cDNA library derived from human cells. The cDNA can be derived from mRNA and contained in a suitable vector. Corresponding clones can be isolated, DNA obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

Antibodies

The invention also provides antibodies which bind to an epitope comprising either a variant amino acid sequence (e.g., comprising an amino acid substitution) encoded by a variant allele or the reference amino acid sequence encoded by the corresponding non-variant or wild-type allele. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immune reacting with a particular epitope of a polypeptide of the invention. A monoclonal antibody composition thus typically displays a single binding affinity for a particular polypeptide of the invention with which it immune reacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. N. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention, such as variant proteins that are encoded by nucleic acids that contain at least one polymorpic marker of the invention, can be used to identify individuals that require modified treatment modalities.

Antibodies can furthermore be useful for assessing expression of variant proteins in disease states, such as in active stages of a disease, or in an individual with a predisposition to a disease related to the function of the protein (e.g., an ZFHX3 protein). Antibodies specific for a variant protein of the present invention that is encoded by a nucleic acid that comprises at least one polymorphic marker or haplotype as described herein can be used to screen for the presence of the variant protein, for example to screen for a predisposition to atrial fibrillation, atrial flutter and/or stroke as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting examples.

EXAMPLE 1

Atrial fibrillation (AF) is a common condition with a lifetime risk of one in four for men and women 40 years of age and older (Lloyd-Jones, D. M. et al. *Circulation* 110, 1042-6 (2004)). The disease carries significant mortality as well as morbidity and is a major risk factor for cardioembolic stroke (CES), one form of ischemic stroke (IS). AF increases the risk of stroke four to fivefold across all age groups and accounts for 10-15% of all IS (Lip, G. Y. & Boos, *Heart* 92, 155-61 (2006)).

A previous genome-wide association study in Iceland identified sequence variants close to the PITX2 gene on chromosome 4q25 that confer risk of AF and atrial flutter (AFI) (Gudbjartsson, D. F. et al. *Nature* 448, 353-7 (2007)). To search for additional variants that associate with AF, we increased the Icelandic sample size of this association study to 2,385 AF/AFI cases and 33,752 controls. In a follow up study we used additional study groups of European ancestry as described in the following.

Methods.

Study Population-Atrial Fibrillation

ICELAND: This study included all patients diagnosed with AF and/or AFI (International Classification of Diseases (ICD) 10 code I48 and ICD 9 code 427.3) at Landspitali University Hospital in Reykjavik, the only tertiary referral centre in Iceland, and at Akureyri Regional Hospital, the second largest hospital in Iceland, from 1987 to 2008. All diagnoses were confirmed with a 12-lead electrocardiogram (ECG). All AF/AFI cases were included except those that occurred only immediately after cardiac surgery. A set of 2,385 cases (1,411 males and 973 females) were successfully genotyped in accordance with our quality control criteria. The mean age at first diagnosis was 72.9 (SD=12.0) years. The follow-up group of 989 patients (661 males and 328 females) had a mean age at diagnosis of 67.0 (SD=13.5) years. The AF/AFI-free controls (13,960 males and 19.783 females at the initial genome-wide screening and 1,137 males and 890 females at the follow-up stage) used in this study consisted of controls randomly selected from the Icelandic genealogical database and individuals from other ongoing related, but not cardiovascular, genetic studies at deCODE. Controls with first-degree relatives (siblings, parents or offspring) with AF/AFI, or a first-degree control relative, were excluded from the analysis. The study was approved by the Data Protection Commission of Iceland and the National Bioethics Committee of Iceland. Written informed consent was obtained from all patients, relatives and controls. Personal identifiers associated with medical information and blood samples were encrypted with a third-party encryption system as described previously (Grant, S. F. et al., *Nat Genet.* 38, 320-3 (2006)).

NORWAY: The Tromsø Study is a population-based prospective study with repeated health surveys in the municipality of Tromsø, Norway. So far, more than 50,000 individuals have been examined. The population is being followed-up on an individual level with registration and validation of diseases and death and an endpoint registry has been established for CVD. Discharge diagnosis lists of CVD have been retrieved from the University Hospital of North Norway in Tromsø, and medical records for all individuals with a CV discharge diagnosis (including visits to out-patient clinics, out of hospital journals, autopsy records and death certificates) have been reviewed.

AF has been registered from 1986-2004 as part of the ongoing CV endpoint registration in the Tromsø Study. We searched the hospital discharge diagnosis registry for ICD-9 codes 427.0 (paroxysmal supraventricular tachycardia (SVT)) and 427.3 (AF) and ICD-10 codes 147.1 (SVT) and 148 (AF/AFI). The date of first ECG-verified AF was recorded, as well as whether the AF was paroxysmal, chronic (persistent or permanent), or of unknown type. We also included AFI in the case group. People with postoperative AF only (<=28 days after the procedure) are registered, but are not included as cases. If AF occurred in the postoperative period, but then continued as a paroxysmal or chronic AF, that subject was included as a case. For the current project, we drew one sex- and age matched control for each case of AF from the population based Tromsø 4 survey. We also surveyed hospital records of controls and excluded all those with possible AF, AFI, SVT and other unspecified arrhythmias.

UNITED STATES: All study subjects from the United States were recruited from the Vanderbilt AF Registry, a clinical and genetic registry at the Vanderbilt University Medical Center in Nashville, Tenn. At enrollment into the registry, a detailed medical and drug history is obtained from all patients and patients are also asked to complete a symptom questionnaire. Patients with history of AF only associated with cardiac surgery were excluded from this study. Written informed consent was obtained from all patients under a protocol approved by the Vanderbilt University Institutional Review Board.

HONG KONG: All subjects in the Hong Kong study population were of southern Han Chinese ancestry residing in Hong Kong. The cases consisted of 217 individuals (49.1% males, mean age 68.1 (SD=9.6)) selected from the Prince of Wales Hospital Diabetes Registry (Yang, X. et al., *Diabetes Care* 30, 65-70 (2007)) and 116 subjects (30.2% male, mean age 76.1 (SD=10.9)) from the Stroke Registry (Baum, L. et al., *Clin Chem Lab Med* 42, 1370-6 (2004)). All subjects were diagnosed by ECG as having AF. The controls consisted of 2,836 subjects without evidence of AF. Informed consent was obtained for each participating subject. This study was approved by the Clinical Research Ethics Committee of the Chinese University of Hong Kong.

Study Population-Stroke

ICELAND: Icelandic stroke patients were recruited from a registry of over 4,000 individuals diagnosed with ischemic stroke or transient ischemic attack (TIA) at the only University hospital in Reykjavik, the Landspitali University Hospital, during the years 1993 to 2006. Stroke patients have been enrolled since 1998 through the cardiovascular disease (CVD) genetics program at deCODE (mean age±SD: 77.2±11.3 years, 45% females for whole sample set). Stroke diagnosis was clinically confirmed by neurologists, based on the traditional WHO criteria of stroke (Report of the WHO Task Force on Stroke and other Cerebrovascular Disorders. *Stroke* 20, 1407-31 (1989)) and imaging evidence. The study was approved by the Data Protection Commission of Iceland (DPC) and the National Bioethics Committee of Iceland. All participants gave informed consent.

SWEDEN: Swedish patients with ischemic stroke attending the stroke unit or the stroke outpatient clinic at Karolinska University Hospital, Huddinge unit in Stockholm, Sweden, were recruited from 1996 to 2002 as part of an ongoing genetic epidemiology study, the South Stockholm Ischemic Stroke Study (SSISS) (mean age±SD: 67.3±11.8 years, 44% females). The Swedish controls used in this study are population-based controls recruited from the same region in central Sweden as the patients, representing the general population in this area. The individuals were either blood donors recruited at the Huddinge or Karolinska University Hospitals or healthy volunteers (recruited in 1990-1994) recruited by the Clinical Chemistry Department at the Karolinska University Hospital to represent a normal reference population. The study was approved by the Bioethics Committee of the Karolinska Institute.

GERMANY: The German population referred to as Germany-S, consisted of patients with ischemic stroke consecutively recruited during the period 2001-2006 at the stroke unit of the Department of Neurology, Klinikum Grosshadern, University of Munich, Germany (mean age 65.3 (SD=13.7) years, 38% females). The control group consisted of age and gender matched individuals without history of cardiovascular disease. These were selected from the KORA S4 study, a community based epidemiological project near Munich (Wichmann, H. E., et. al., *Gesundheitswesen* 67 Suppl 1, S26-30 (2005)). The study was approved by the local ethics committee and informed consent was obtained from all individuals (or relatives or legal guardians).

The second German population, referred to as Germany-W, recruited ischemic stroke patients through hospitals participating in the regional Westphalian Stroke Register, located in the west of the country, during the period 2000-2003 (mean age 70.4 (SD=12.6) years, 53% females). Population controls without a self-reported history of stroke were drawn from the cross-sectional, prospective, population based Dortmund Health Study (Berger, K. et al., *Hum Genet.* 121, 169-78 (2007)), conducted in the same region, and subsequently frequency matched to cases. Both studies were approved by the ethics committee of the University of Muenster. All participants gave their informed consent.

EGLAND: Ischemic stroke patients of European descent attending a cerebrovascular service were recruited 1995-2002. All cases were phenotyped by one experienced stroke neurologist with review of original imaging (mean age 64.6 (SD=12.7) years, 41% females). Community controls free of symptomatic cerebrovascular disease were also recruited by sampling family doctor lists from the same geographical region as the patients. Sampling was stratified to provide a similar distribution of age and gender as in the patient group. The study was approved by local research ethics committees and informed consent was obtained from all participants.

Stroke Phenotyping

Only patients with ischemic but not with hemorrhagic stroke were included in the study. All patients had clinically relevant diagnostic workup performed, including brain imaging with computed tomography (CT) and/or magnetic resonance imaging (MRI) as well as ancillary diagnostic investigations including duplex ultrasonography of the carotid and vertebral arteries, echocardiography, Holter monitoring, MR-angiography, CT-angiography and blood tests. Patients were classified into etiologic subtypes according to the Trial of Org 10172 in Acute Stroke Treatment (TOAST) (Adams, H. P., Jr. et al., *Stroke* 24, 35-41 (1993)). The classification was performed independently for each stroke population but in a standardized manner. The TOAST classification includes six categories: (1) large-artery occlusive disease (large vessel disease), (2) cardioembolism (cardiogenic stroke), (3) small vessel disease (lacunar stroke), (4) other determined etiology, (5) etiology unknown despite diagnostic efforts, or (6) more than one etiology. Patients classified into the TOAST categories 4-6 were excluded from the stroke population from Germany-W. In Iceland, patients were classified as having large-artery occlusive disease if stenosis was ≥70% which is a stricter criterion than usually used i.e. ≥50%. The proportion of patients with CE ischemic stroke that had atrial fibrillation were 79% in Iceland, 73% in Germany-S and Sweden, 71% in Germany-W and 56% in UK. Breakdown of the ischemic stroke (IS) patients into subtypes according to the TOAST classification system (Adams, H. P., Jr. et al., *Stroke* 24, 35-41 (1993)) in the sample sets from Iceland, Germany-S, Sweden, Germany-W and UK was listed previously (Gretarsdottir, S. et al., *Ann Neurol* 64, 402-9 (2008)).

Genotyping

A genome-wide scan for sequence variants associating with atrial fibrillation in Iceland was performed and followed up the most significant associations in samples from Iceland, Norway and USA ILLUMINA GENOME-WIDE GENOTYPING: All Icelandic case and control samples were assayed with the Illumina HumanHap300 and HumanHapCNV370 bead chips (Illumina, SanDiego, Calif., USA) containing 317,503 and 370,404 haplotype tagging SNPs derived from phase I of the International HapMap project. Only SNPs present on both chips were included in the analysis and SNPs were excluded if they had (a) yield lower than 95% in cases or controls, (b) minor allele frequency less than 1% in the population, or (c) showed significant deviation from Hardy-Weinberg equilibrium in the controls (P<0.001). Any samples with a call rate below 98% were excluded from the analysis. The final analysis included 304,226 SNPs.

SINGLE SNP GENOTYPING: Single SNP genotyping for all samples was carried out at deCODE genetics in Reykjavik, Iceland, applying the same platform to all populations studied, the Centaurus (Nanogen) platform (Kutyavin, I. V. et al., *Nucleic Acids Res* 34, e128 (2006)). The quality of each Centaurus SNP assay was evaluated by genotyping each assay in the CEU and/or YRI HapMap samples and comparing the results with the HapMap data. Assays with >1.5% mismatch rate were not used and a linkage disequilibrium (LD) test was used for markers known to be in LD.

Association Analysis

For association analysis we utilized a standard likelihood ratio statistic, implemented in the NEMO software (Gretarsdottir, S. et al., *Nat Genet.* 35, 131-8 (2003)) to calculate two-sided P values and odds ratios (ORs) for each individual allele, assuming a multiplicative model for risk, i.e. that the risk of the two alleles a person carries multiplies (Rice, J. A. *Mathematical statistics and data analysis*, xx, 602, A49 p. (Duxbury Press, Belmont, Calif., 1995)).

Allelic frequencies, rather than carrier frequencies are presented for the markers and P values are given after adjustment for the relatedness of the subjects. When estimating genotype specific OR, genotype frequencies in the population were estimated assuming Hardy-Weinberg equilibrium.

Results from multiple case-control groups were combined using a Mantel-Haenszel model (Mantel, N. & Haenszel, *J Natl Cancer Inst* 22, 719-48 (1959)) in which the groups were allowed to have different population frequencies for alleles, haplotypes and genotypes but were assumed to have common relative risks.

Correction for Relatedness and Genomic Control.

Some of the individuals in both the Icelandic patient and control groups are related to each other, causing the chi-square test statistic to have a mean greater than 1 and median greater than $0.675^2$. We estimated the inflation factor for the genome-wide association by calculating the median of the 304,226 chi-square statistics, which was a method of genomic control (Devlin, B. & Roeder, K. *Biometrics* 55, 997-1004 (1999)) to adjust for both relatedness and potential population stratification. The inflation factor was estimated as 1.11 and the results presented from the genome-wide association are based on adjusting the chi-square statistics by dividing each of them by this factor. To adjust the association results for the Icelandic follow-up sample set, and the combined replication and discovery sample set, where association results for a genome-wide set of SNPs is not available, we used a previously described procedure where we simulated genotypes through the genealogy of 708,683 Icelanders to estimate the adjustment factor (Stefansson, H. et al., *Nat Genet.* 37, 129-37 (2005)). The adjustment factors for the replication and combined set of AF cases and controls were 1.11 and 1.15, respectively. The same procedure was used to adjust the association with IS and CES and the correction factors used there were 1.08 for IS and 1.03 for CES.

Results.

A sequence variant, rs7193343-T, in the ZFHX3 gene on chromosome 16q22 associated significantly with atrial fibrillation (AF) (combined OR=1.22, $P=4.1 \cdot 10^{-11}$). This variant also associates with ischemic stroke (OR=1.11, P=0.00054) and cardioembolic stroke (OR=1.22, P=0.00021) in a combined analysis of five stroke sample sets. Another variant, rs7618072-G on chromosome 3 showed borderline association with AF.

Of the top ten SNPs from our genome-wide analysis, the seven most significant variants correspond to the previously reported signal on chromosome 4q25 (Gudbjartsson, D. F. et al., *Nature* 448, 353-7 (2007), (Table 1). The remaining three SNPs have not been associated with AF/AFI before.

TABLE 1

Shows the ten most significant SNPs identified through a genome-wide association scan of Icelandic AF/AFI patients.

| | | | N | | Frequency | | | |
|---|---|---|---|---|---|---|---|---|
| SNP/Allele | Chr | Position | Cases | Ctrls | Cases | Ctrls | OR | P |
| rs2220427 | 4 | 4 112,072,493 | 2,380 | 33,685 | 0.158 | 0.117 | 1.42 | $1.4 \cdot 10^{-14}$ |
| rs2200733 | 4 | 4 112,067,773 | 2,385 | 33,749 | 0.157 | 0.117 | 1.42 | $1.4 \cdot 10^{-14}$ |
| rs2634073 | 3 | 4 112,023,387 | 2,381 | 33,712 | 0.791 | 0.837 | 0.73 | $1.4 \cdot 10^{-14}$ |
| rs13141190 | 3 | 4 112,086,218 | 2,385 | 33,745 | 0.578 | 0.636 | 0.78 | $2.3 \cdot 10^{-14}$ |
| rs1448817 | 3 | 4 111,998,657 | 2,383 | 33,718 | 0.292 | 0.247 | 1.25 | $1.6 \cdot 10^{-10}$ |
| rs2723316 | 4 | 4 111,991,891 | 2,384 | 33,747 | 0.335 | 0.296 | 1.20 | $5.9 \cdot 10^{-8}$ |

TABLE 1-continued

Shows the ten most significant SNPs identified through a genome-wide association scan of Icelandic AF/AFI patients.

| SNP/Allele | Chr | Chr | Position | N Cases | N Ctrls | Frequency Cases | Frequency Ctrls | OR | P |
|---|---|---|---|---|---|---|---|---|---|
| rs16997168 | 4 | 4 | 111,986,643 | 2,385 | 33,745 | 0.183 | 0.153 | 1.25 | $1.3 \cdot 10^{-7}$ |
| rs958800 | 4 | 4 | 87,071,478 | 2,384 | 33,743 | 0.315 | 0.280 | 1.18 | $2.0 \cdot 10^{-6}$ |
| rs7618072 | 4 | 3 | 160,164,264 | 2,385 | 33,712 | 0.759 | 0.726 | 1.19 | $2.4 \cdot 10^{-6}$ |
| rs7193343 | 4 | 16 | 71,586,661 | 2,381 | 33,723 | 0.229 | 0.199 | 1.20 | $3.1 \cdot 10^{-6}$ |

Shown are the allele, chromosome and chromosome position, number of cases and controls successfully genotyped, the allele frequency, OR and P value for each SNP. Allelic codes are A = 1, C = 2, G = 3, T = 4.

To follow up our findings we genotyped the three SNPs in three additional sample sets of European ancestry, from Iceland (roughly 1000 cases and 2,400 controls), Norway (725 cases and 725 controls) and the US (735 cases and 729 controls). One of the three SNPs; rs958800 did not associate significantly with AF/AFI in the follow-up samples and failed to reach genome-wide significance (Table 2). A second variant, rs7618072-T showed borderline association with AF/Afl, mainly due to the combined Icelandic cohorts (Table 2).

TABLE 2

Association of rs958800-T and rs7618072-T with AF/AFI.

| Sample (cases/controls) | Risk allele frequency | OR (95% CI) | P-value |
|---|---|---|---|
| rs958800 T | | | |
| Iceland | | | |
| Discovery (2384/33743) | 0.315 (0.280) | 1.18 (1.10, 1.26) | 2.00E−06 |
| Follow-up (656/2325) | 0.284 (0.290) | 0.97 (0.84, 1.12) | 0.68 |
| Combined (3305/36210) | 0.309 (0.281) | 1.15 (1.08, 1.22) | 5.10E−06 |
| Other European ancestry | | | |
| Norway (705/694) | 0.249 (0.245) | 1.02 (0.86, 1.21) | 0.81 |
| US (721/730) | 0.250 (0.251) | 0.99 (0.84, 1.18) | 0.95 |
| Combined | — (—) | 1.01 (0.89, 1.14) | 0.90 |
| All European ancestry | | | |
| Combined | — (—) | 1.11 (1.05, 1.17) | 0.00018 |
| rs7618072 T | | | |
| Iceland | | | |
| Discovery (2385/33712) | 0.759 (0.726) | 1.19 (1.11, 1.27) | 2.40E−06 |
| Follow-up (934/2473) | 0.734 (0.723) | 1.06 (0.93, 1.20) | 0.39 |
| Combined (3737/36160) | 0.748 (0.726) | 1.12 (1.06, 1.19) | 0.00012 |
| Other European ancestry | | | |
| Norway (703/700) | 0.763 (0.794) | 0.84 (0.70, 1.00) | 0.052 |
| US (718/658) | 0.782 (0.757) | 1.15 (0.97, 1.38) | 0.12 |
| Combined | — (—) | 0.98 (0.87, 1.12) | 0.80 |
| All European ancestry | | | |
| Combined | — (—) | 1.11 (1.05, 1.17) | 0.00018 |

For each sequence variant, results are shown for association with the Icelandic discovery data set, and a follow-up set, the two Icelandic data sets combined, follow-up data sets from Norway, US, and for all the data sets combined. Shown are the number of cases and controls for each study group, frequency of risk allele, the OR, and P values. For the Icelandic study groups, the P values and CI were adjusted for relatedness.

The T allele of the third variant, rs7193343, located on chromosome 16q22 (Table 3), showed genome-wide significant association with AF/AFI in the combined Icelandic sample set (OR=1.22, P=$1.7 \cdot 10^{-9}$). This association was subsequently replicated in the non-Icelandic samples (OR=1.22, P=0.0046). The combined effect of rs7193343-T in the discovery and three follow-up sets was OR=1.22 (95% CI: 1.15-1.29) with a corresponding P value of $4.1 \cdot 10^{-11}$.

TABLE 3

Association of rs7193343-T on chromosome 16q22 with AF/AFI.

| Sample (cases/controls) | rs7193343 T frequency | OR (95% CI) | P-value |
|---|---|---|---|
| Iceland | | | |
| Discovery (2381/33723) | 0.229 (0.199) | 1.20 (1.11, 1.29) | 3.10E−06 |
| Follow-up (1032/2119) | 0.241 (0.202) | 1.26 (1.10, 1.44) | 0.0007 |
| Combined (3413/35831) | 0.232 (0.199) | 1.22 (1.14, 1.30) | 1.70E−09 |
| Other European ancestry | | | |
| Norway (722/711) | 0.177 (0.166) | 1.08 (0.89, 1.31) | 0.45 |
| US (735/729) | 0.183 (0.139) | 1.39 (1.14, 1.70) | 0.0010 |
| Combined (1,457/1,440) | — (—) | 1.22 (1.06, 1.40) | 0.0046 |
| All European ancestry | | | |
| Combined | — (—) | 1.22 (1.15, 1.29) | 4.10E−11 |
| Chinese ancestry | | | |
| Hong Kong (285/2,763) | 0.686 (0.676) | 1.05 (0.87, 1.26) | 0.68 |

Results are shown for the Icelandic discovery data set, and a follow-up dataset, the two Icelandic data sets combined, and follow-up data sets from Norway, US, and for all the datasets combined. Shown are the number of cases and controls for each study group, the frequency, the OR, and P values. For the Icelandic study groups, the P values and CI were adjusted for relatedness.

We assessed the association of rs7193343-T with AF in a Han Chinese population from Hong Kong, consisting of 286 AF cases and 2763 controls. The association did not reach statistical significance in this cohort although the direction of association was consistent with that in the European samples (OR=1.05, P=0.68, Table 3). Notably, the T allele of rs7193343 is much more frequent in the Han Chinese population (the allelic frequency in controls is 0.68) than the samples of European descent (the allelic frequency in controls is between 0.14 and 0.21).

In our previous genome-wide study on AF/AFI, a stronger association was observed with the relatively small subset of individuals with a definite history of AFI than other cases (Gudbjartsson, D. F. et al. Nature 448, 353-7 (2007)). We therefore tested rs7193343 in the subset of 160 Icelandic patients with a definite history of AFI. The association with AFI is similar to that with AF although it does not reach nominal significance on its own (OR=1.25, 95% CI: 0.96, 1.62, P=0.093).

We found no correlation between rs7193343 and obesity, hypertension or coronary artery disease in the Icelandic sample set. This suggests that the association between rs7193343 and AF is not mediated through these known risk factors for AF.

We have previously reported the results of our genome-wide association study of stroke where the AF variants on chromosome 4q25 were found to significantly associate with ischemic stroke (IS), and as expected, with the strongest risk for the cardioembolic stroke (CES) subclass of IS (Gretarsdottir, S. et al. Ann Neurol 64, 402-9 (2008)). To assess the correlation between rs7193343 and stroke, we tested this variant in five IS case-control sample sets of European descent, from Iceland, Sweden, West-Germany, South-Germany and the United Kingdom. Combined analysis of the five datasets showed significant association between rs7193343 and IS (OR=1.11, 95% CI: 1.04-1.17, P=0.00054) (Table 4). Association analysis of IS subclasses showed significant association between rs7193343 and CES with an OR comparable to the association between rs7193343 and AF (OR=1.22, 95% CI: 1.10-1.35, P=0.00021).

protein (AFP) gene expression in the liver (Morinaga, T, et. al., Mol Cell Biol 11, 6041-9 (1991)). At the time of its discovery it was the largest DNA binding protein reported and the first protein shown to contain multiple homeodomains and multiple zinc finger motifs (Morinaga, T., et. al. Mol Cell Biol 11, 6041-9 (1991)). The gene has since been associated with regulation of growth and differentiation of several tissues, including neuronal and skeletal muscle differentiation (Berry, F. B. et al. 3 Biol Chem 276, 25057-65 (2001)).

TABLE 4

Shows association of rs7193343-T on chromosome 16q22 with ischemic stroke and cardioembolic stroke.

| | Controls | | Ischemic stroke | | | | Cardioembolic stroke | | | |
|---|---|---|---|---|---|---|---|---|---|---|
| Sample | N | Freq | N | Freq | OR (95% CI) | P-value | N | Freq | OR (95% CI) | P-value |
| Iceland | 36,430 | 0.201 | 2,308 | 0.208 | 1.05 (0.97, 1.13) | 0.22 | 419 | 0.223 | 1.16 (0.98, 1.37) | 0.084 |
| Sweden | 700 | 0.156 | 856 | 0.183 | 1.21 (1.00, 1.46) | 0.046 | 151 | 0.172 | 1.12 (0.80, 1.57) | 0.50 |
| S-Germany | 1,088 | 0.167 | 1,133 | 0.187 | 1.14 (0.98, 1.33) | 0.090 | 283 | 0.214 | 1.35 (1.07, 1.71) | 0.011 |
| W-Germany | 1,107 | 0.164 | 1,353 | 0.187 | 1.17 (1.01, 1.36) | 0.034 | 540 | 0.192 | 1.21 (1.00, 1.47) | 0.046 |
| UK | 573 | 0.123 | 585 | 0.152 | 1.28 (1.01, 1.62) | 0.042 | 62 | 0.161 | 1.37 (0.81, 2.32) | 0.24 |
| Combined | 39,898 | — | 6,235 | — | 1.11 (1.04, 1.17) | 0.00054 | 1,454 | — | 1.22 (1.10, 1.35) | 0.00021 |

Results are shown for data sets for Iceland, Sweden, South-Germany, West-Germany and the UK, and for all the datasets combined. Shown are the number of controls and number of cases with each phenotype, frequency of risk allele, the OR and P values. For the Icelandic study group, the P values and CI were adjusted for relatedness.

TABLE 5

Surrogate markers (based on HapMap Caucasian CEU sample set; http://www.hapmap.org) on Chromosome 16 and Chromosome 3 with $r^2 > 0.2$ to the anchor markers; rs7193343 and rs7618072.

| Surrogate Marker | Anchor Marker (Seq ID No: 2) | Chr | Risk Allele | Pos in NCBI B_36 | Pos in Seq ID No: 1 | D' | $R^2$ |
|---|---|---|---|---|---|---|---|
| rs16971447 | rs7193343 | chr16 | 2 | 71565471 | 1 | 1 | 0.571865 |
| rs16971471 | rs7193343 | chr16 | 1 | 71575185 | 9715 | 0.819005 | 0.461806 |
| rs7193343 | rs7193343 | chr16 | 4 | 71586661 | 21191 | 1 | |
| rs719353 | rs7193343 | chr16 | 1 | 71600052 | 34582 | 1 | 0.247059 |
| rs719354 | rs7193343 | chr16 | 4 | 71600430 | 34960 | 1 | 0.936909 |
| rs2106261 | rs7193343 | chr16 | 1 | 71609121 | 43651 | 0.867987 | 0.706751 |
| rs1548374 | rs7193343 | chr16 | 2 | 71617230 | 51760 | 1 | 0.230769 |
| rs879324 | rs7193343 | chr16 | 4 | 71626179 | 60709 | 0.80198 | 0.603347 |
| rs8057081 | rs7193343 | chr16 | 4 | 71626478 | 61008 | 0.777562 | 0.332695 |
| rs12932445 | rs7193343 | chr16 | 2 | 71627389 | 61919 | 0.790419 | 0.588095 |
| rs9940321 | rs7193343 | chr16 | 1 | 71631309 | 65839 | 0.830177 | 0.243245 |

| Surrogate Marker | Anchor Marker (Seq ID No: 3) | Chr | Risk Allele | Pos in NCBI B_36 | D' | $R^2$ |
|---|---|---|---|---|---|---|
| rs340263 | rs7618072 | chr3 | 2 | 160099664 | 0.753695 | 0.565646 |
| rs391398 | rs7618072 | chr3 | 3 | 160107373 | 0.777086 | 0.28417 |
| rs340234 | rs7618072 | chr3 | 2 | 160108768 | 0.668339 | 0.203286 |
| rs340233 | rs7618072 | chr3 | 3 | 160109593 | 0.757356 | 0.573587 |
| rs340229 | rs7618072 | chr3 | 1 | 160110339 | 0.772002 | 0.269514 |
| rs340261 | rs7618072 | chr3 | 3 | 160118751 | 0.757356 | 0.573587 |
| rs340293 | rs7618072 | chr3 | 2 | 160123438 | 0.757356 | 0.573587 |
| rs340241 | rs7618072 | chr3 | 2 | 160144253 | 1 | 0.372549 |
| rs4679844 | rs7618072 | chr3 | 1 | 160163710 | 1 | 0.639549 |
| rs7618072 | rs7618072 | chr3 | 4 | 160164256 | 1 | |
| rs9855092 | rs7618072 | chr3 | 1 | 160166644 | 0.817817 | 0.565764 |
| rs1501293 | rs7618072 | chr3 | 1 | 160196252 | 0.591751 | 0.218141 |

Shown is; Surrogate marker name, Anchor marker, Chromosome, the allele that is correlated with risk-allele of the anchor-marker, position of surrogate marker in in NCBI Build 36, D' and $r^2$. Allelic codes are A = 1, C = 2, G = 3, T = 4.

The sequence variant rs7193343 is an intronic SNP located in the zinc finger homeobox 3 (ZFHX3) gene on chromosome 16q22, also called AT motif-binding factor 1 (ATBF1). The same variant was recently associated with Kawasaki disease, an inflammatory vasculitis predominantly seen in young children (Burgner, D. et al. PLoS Genet 5, e1000319 (2009)). This gene encodes a transcription factor named Atbf1 which was first described as an enhancer of the human alpha-feto- ZFHX3 is expressed in various tissues e.g. heart, liver, lung, kidney, pituitary gland and brain. ATBF1 is required for early transcriptional activation of the gene (POU1F1), a member of the POU-homeodomain transcription factor family that regulates pituitary cell differentiation and hormone expression in mammals (Qi, Y. et al. Proc Natl Acad Sci USA 105, 2481-6 (2008)). POU1F1 has been demonstrated to interact with the paired-like homeodomain transcription factor 2 (PITX2) to facilitate DNA binding and transcriptional activity (Amendt, B. A., 3 Biol Chem 273, 20066-72 (1998)), an interesting observation as the previously identified AF variants on chromosome 4q25 are located close to PITX2, a gene critical for heart development.

Association analysis of rs16971471 and rs1548374, which are two of the surrogate markers of rs7193343 indicated in Table 5, shows that rs1548374 associates with AF in the Icelandic population with observed OR for the C allele of this marker of 1.11 and P-value of 0.0013 (2382 cases and 33737 controls), while the A allele of rs16971471 associates with AF with an observed OR value of 1.10 and P-value of 0.058 (2385 cases and 33737 controls). Thus, both markers associate with AF, albeit with lower OR values than rs7193343. Accordingly, larger sample sets with more statistical power would be needed to detect association with AF with same statistical significance as observed for rs7193343.

EXAMPLE 2

Identification of Sequence Variants Conferring Risk of Atrial Fibrillation

The following describes further identification of nine variants conferring risk for atrial fibrillation on Chromosomes 1, 2, 4, 5, 15, 18 and 20.

Genome-wide scan of about 3,700 Icelandic patients with Atrial Fibrillation and over 36,000 controls showed association between atrial fibrillation and nine SNPs at various locations in the genome. These were identified as; rs2935888 (chr 1), rs1394796 and rs10490066 (chr 2), rs4560443 (chr 4), rs10077199 and rs7733337 (chr 5), rs10519674 (chr15), rs10516002 (chr18) and rs6010770 (chr 20).

This association was also confirmed in two additional AF sample sets of European ancestry, namely Norwegian and US. Descriptions of the three study populations, genotyping methods and statistical analysis, were as outlined in Exemplification 1 above. Results are displayed in Table 7.

TABLE 6

Presenting association of nine variants with AF.

| Sample (cases/controls) | Risk allele freq. | OR (95% CI) | P-value |
|---|---|---|---|
| rs10077199 - Allele 4 | | | |
| Iceland (3733/36229) | 0.442 | 1.08 | 0.0028621 |
| Norway (707/696) | 0.471 | 1.09 | 0.274316 |
| US (732/715) | 0.422 | 1.09 | 0.241425 |
| Combined | | 1.08 | 0.00072 |

TABLE 6-continued

Presenting association of nine variants with AF.

| Sample (cases/controls) | Risk allele freq. | OR (95% CI) | P-value |
|---|---|---|---|
| rs10490066 - Allele 1 | | | |
| Iceland (3724/36119) | 0.219 | 1.13 | 0.000169 |
| Norway (720/701) | 0.190 | 1.03 | 0.741805 |
| US (726/722) | 0.207 | 1.14 | 0.168639 |
| Combined | | 1.12 | 8.90E-05 |
| rs10516002 - Allele 1 | | | |
| Iceland (3737/36220) | 0.152 | 1.11 | 0.004313 |
| Norway (702/693) | 0.123 | 1.37 | 0.010261 |
| US (742/737) | 0.111 | 0.99 | 0.901639 |
| Combined | | 1.12 | 0.001 |
| rs10519674 - Allele 3 | | | |
| Iceland (3725/36055) | 0.088 | 1.17 | 0.001154 |
| Norway (711/705) | 0.066 | 1.21 | 0.22922 |
| US (742/742) | 0.049 | 1.19 | 0.328831 |
| Combined | | 1.17 | 0.00033 |
| rs1394796 - Allele 2 | | | |
| Iceland (3624/35852) | 0.730 | 1.12 | 6.91E-05 |
| Norway (718/715) | 0.708 | 1.03 | 0.719418 |
| US (691/717) | 0.732 | 1.04 | 0.676362 |
| Combined | | 1.11 | 0.00014 |
| rs2935888 - Allele 4 | | | |
| Iceland (3301/36129) | 0.880 | 1.12 | 0.005742 |
| Norway (713/701) | 0.868 | 1.21 | 0.081535 |
| US (734/726) | 0.876 | 1.01 | 0.955761 |
| Combined | | 1.12 | 0.0023 |
| rs4560443 - Allele 4 | | | |
| Iceland (3731/36106) | 0.347 | 1.13 | 7.43E-06 |
| Norway (705/703) | 0.290 | 1.10 | 0.259534 |
| US (694/642) | 0.323 | 1.07 | 0.425051 |
| Combined | | 1.12 | 3.60E-06 |
| rs6010770 - Allele 3 | | | |
| Iceland (3736/36150) | 0.956 | 1.20 | 0.002648 |
| Norway (714/698) | 0.931 | 1.33 | 0.03984 |
| US (721/742) | 0.928 | 1.05 | 0.728978 |
| Combined | | 1.2 | 0.00055 |
| rs7733337 - Allele 4 | | | |
| Iceland (3739/36210) | 0.904 | 1.14 | 0.002447 |
| Norway (707/697) | 0.888 | 1.15 | 0.234762 |
| US (743/749) | 0.902 | 1.35 | 0.00961 |
| Combined | | 1.16 | 8.60E-05 |

For each sequence variant, results show association with Icelandic discovery data set, data sets from Norway and US, and for all the data sets combined. Shown are the number of cases and controls for each study group, risk allele frequency, observed risk (OR), and P values.

TABLE 7

Surrogate markers (based on HapMap Caucasian CEU sample set; http://www.hapmap.org) to anchor markers associated with AF with $r^2 > 0.2$.

| Surrogate Marker | Anchor Marker | Chr | Risk Allele | Pos in NCBI B_36 | D' | R2 |
|---|---|---|---|---|---|---|
| rs1531202 | rs4560443 | chr4 | 4 | 64197573 | 0.794739 | 0.219401 |
| rs2124786 | rs4560443 | chr4 | 3 | 64211677 | 0.794739 | 0.219401 |
| rs7690053 | rs4560443 | chr4 | 4 | 64255898 | 0.794739 | 0.219401 |
| rs17686902 | rs4560443 | chr4 | 1 | 64323707 | 0.922825 | 0.252199 |
| rs2168580 | rs4560443 | chr4 | 1 | 64328367 | 0.928538 | 0.289531 |
| rs2881736 | rs4560443 | chr4 | 4 | 64341632 | 0.92677 | 0.277955 |
| rs17636187 | rs4560443 | chr4 | 4 | 64345372 | 0.925483 | 0.268164 |
| rs2347824 | rs4560443 | chr4 | 3 | 64346387 | 1 | 0.228886 |
| rs17636490 | rs4560443 | chr4 | 2 | 64350772 | 0.921581 | 0.245853 |
| rs4035252 | rs4560443 | chr4 | 3 | 64355480 | 1 | 0.218362 |
| rs12501809 | rs4560443 | chr4 | 3 | 64362334 | 1 | 0.22366 |

TABLE 7-continued

Surrogate markers (based on HapMap Caucasian CEU sample set; http://www.hapmap.org) to anchor markers associated with AF with $r^2 > 0.2$.

| Surrogate Marker | Anchor Marker | Chr | Risk Allele | Pos in NCBI B_36 | D' | R2 |
|---|---|---|---|---|---|---|
| rs4560443 | rs4560443 | chr4 | 4 | 64398956 | 1 | |
| rs11131484 | rs4560443 | chr4 | 2 | 64410389 | 1 | 0.896433 |
| rs17688509 | rs4560443 | chr4 | 3 | 64414638 | 1 | 0.896433 |
| rs6852697 | rs4560443 | chr4 | 2 | 64422523 | 1 | 0.210526 |
| rs17637486 | rs4560443 | chr4 | 3 | 64423104 | 0.787438 | 0.20047 |
| rs1316996 | rs4560443 | chr4 | 4 | 64430332 | 0.884662 | 0.701479 |
| rs1375470 | rs4560443 | chr4 | 1 | 64435650 | 0.787438 | 0.20047 |
| rs10027594 | rs4560443 | chr4 | 4 | 64452113 | 0.780125 | 0.224378 |
| rs1349182 | rs4560443 | chr4 | 3 | 64455242 | 0.787438 | 0.20047 |
| rs6551792 | rs4560443 | chr4 | 2 | 64483913 | 0.800483 | 0.230605 |
| rs1449196 | rs4560443 | chr4 | 4 | 64545339 | 0.787438 | 0.20047 |
| rs2881806 | rs4560443 | chr4 | 3 | 64583582 | 0.798423 | 0.482626 |
| rs2053844 | rs4560443 | chr4 | 4 | 64594796 | 0.798423 | 0.482626 |
| rs17084483 | rs4560443 | chr4 | 3 | 64599364 | 0.793965 | 0.478648 |
| rs1449187 | rs4560443 | chr4 | 4 | 64616275 | 0.801437 | 0.503103 |
| rs10028878 | rs4560443 | chr4 | 1 | 64617343 | 0.801437 | 0.503103 |
| rs1579965 | rs4560443 | chr4 | 4 | 64619526 | 0.801437 | 0.503103 |
| rs17697026 | rs4560443 | chr4 | 4 | 64629737 | 0.801437 | 0.503103 |
| rs11728458 | rs4560443 | chr4 | 2 | 64641369 | 0.834572 | 0.293999 |
| rs10519674 | rs10519674 | chr15 | 1 | 28069471 | 1 | |
| rs7164994 | rs10519674 | chr15 | 4 | 28069811 | 1 | 0.342105 |
| rs16954910 | rs10519674 | chr15 | 4 | 28074223 | 1 | 0.433198 |
| rs8040523 | rs10519674 | chr15 | 3 | 28085050 | 0.824561 | 0.679902 |
| rs7723988 | rs7733337 | chr5 | 3 | 174001799 | 0.513835 | 0.200501 |
| rs11739151 | rs7733337 | chr5 | 2 | 174019400 | 0.55038 | 0.247731 |
| rs6556151 | rs7733337 | chr5 | 2 | 174019963 | 0.55038 | 0.247731 |
| rs4242182 | rs7733337 | chr5 | 2 | 174088774 | 0.801425 | 0.602512 |
| rs2381939 | rs7733337 | chr5 | 3 | 174089702 | 0.870765 | 0.755868 |
| rs14459 | rs7733337 | chr5 | 3 | 174090317 | 0.866556 | 0.711055 |
| rs4868444 | rs7733337 | chr5 | 2 | 174092719 | 1 | 0.877363 |
| rs10057011 | rs7733337 | chr5 | 3 | 174093855 | 1 | 0.836586 |
| rs7733337 | rs7733337 | chr5 | 4 | 174096822 | 1 | |
| rs12995889 | rs1394796 | chr2 | 1 | 212759008 | 1 | 0.213373 |
| rs10497971 | rs1394796 | chr2 | 2 | 212933104 | 0.70469 | 0.383983 |
| rs6734836 | rs1394796 | chr2 | 3 | 212941876 | 0.917922 | 0.25846 |
| rs10186681 | rs1394796 | chr2 | 2 | 212947794 | 0.70469 | 0.383983 |
| rs1394781 | rs1394796 | chr2 | 4 | 212957067 | 0.920386 | 0.262896 |
| rs13019524 | rs1394796 | chr2 | 4 | 212959748 | 0.696005 | 0.407934 |
| rs4627509 | rs1394796 | chr2 | 4 | 212966667 | 0.862389 | 0.481901 |
| rs12105481 | rs1394796 | chr2 | 1 | 212973241 | 0.920386 | 0.262896 |
| rs1394796 | rs1394796 | chr2 | 2 | 212978672 | 1 | |
| rs4673664 | rs1394796 | chr2 | 4 | 212985894 | 1 | 0.280804 |
| rs6757140 | rs1394796 | chr2 | 2 | 212987274 | 0.873619 | 0.344152 |
| rs7569142 | rs1394796 | chr2 | 2 | 213002802 | 0.871472 | 0.339599 |
| rs1505367 | rs1394796 | chr2 | 2 | 213004963 | 1 | 0.710723 |
| rs1394791 | rs1394796 | chr2 | 3 | 213006055 | 1 | 0.72093 |
| rs1505376 | rs1394796 | chr2 | 4 | 213012192 | 0.926679 | 0.275553 |
| rs2062930 | rs1394796 | chr2 | 3 | 213021330 | 0.926679 | 0.275553 |
| rs1505371 | rs1394796 | chr2 | 4 | 213024785 | 0.570913 | 0.317658 |
| rs17259208 | rs1394796 | chr2 | 4 | 213024831 | 0.779475 | 0.380641 |
| rs1505370 | rs1394796 | chr2 | 2 | 213030457 | 0.606627 | 0.33525 |
| rs2170529 | rs1394796 | chr2 | 2 | 213036994 | 0.855215 | 0.250947 |
| rs10168850 | rs1394796 | chr2 | 2 | 213042768 | 0.7858 | 0.219106 |
| rs17325821 | rs1394796 | chr2 | 2 | 213044934 | 0.698573 | 0.406755 |
| rs17325842 | rs1394796 | chr2 | 3 | 213045222 | 0.857128 | 0.258387 |
| rs10497975 | rs1394796 | chr2 | 4 | 213050382 | 0.606627 | 0.33525 |
| rs6735807 | rs1394796 | chr2 | 2 | 213052402 | 0.832421 | 0.234448 |
| rs6892188 | rs10077199 | chr5 | 2 | 53104548 | 0.763674 | 0.248531 |
| rs2407066 | rs10077199 | chr5 | 1 | 53124374 | 0.59472 | 0.237924 |
| rs1986932 | rs10077199 | chr5 | 4 | 53142220 | 0.490927 | 0.216048 |
| rs17248426 | rs10077199 | chr5 | 2 | 53151910 | 0.538292 | 0.279157 |
| rs1604827 | rs10077199 | chr5 | 2 | 53179147 | 0.69959 | 0.40416 |
| rs6866140 | rs10077199 | chr5 | 1 | 53192534 | 0.842975 | 0.53647 |
| rs702604 | rs10077199 | chr5 | 1 | 53202393 | 0.51997 | 0.233863 |
| rs2407068 | rs10077199 | chr5 | 2 | 53212159 | 0.752037 | 0.455835 |
| rs271247 | rs10077199 | chr5 | 4 | 53218795 | 0.743979 | 0.402167 |
| rs7729734 | rs10077199 | chr5 | 4 | 53226900 | 0.873349 | 0.554192 |
| rs3776742 | rs10077199 | chr5 | 1 | 53233816 | 0.844193 | 0.66116 |
| rs7713737 | rs10077199 | chr5 | 1 | 53241460 | 0.798562 | 0.514043 |
| rs10077199 | rs10077199 | chr5 | 4 | 53244145 | 1 | |
| rs8091729 | rs10516002 | chr18 | 3 | 63554932 | 0.514825 | 0.265045 |
| rs9946582 | rs10516002 | chr18 | 3 | 63579399 | 1 | 1 |
| rs9319738 | rs10516002 | chr18 | 2 | 63589700 | 1 | 0.205138 |

TABLE 7-continued

Surrogate markers (based on HapMap Caucasian CEU sample set; http://www.hapmap.org) to anchor markers associated with AF with $r^2 > 0.2$.

| Surrogate Marker | Anchor Marker | Chr | Risk Allele | Pos in NCBI B_36 | D' | R2 |
|---|---|---|---|---|---|---|
| rs8083791 | rs10516002 | chr18 | 2 | 63596654 | 1 | 0.414444 |
| rs12455127 | rs10516002 | chr18 | 1 | 63603545 | 1 | 0.554455 |
| rs17832178 | rs10516002 | chr18 | 4 | 63607589 | 1 | 0.660377 |
| rs11874708 | rs10516002 | chr18 | 2 | 63613494 | 1 | 0.557014 |
| rs10516002 | rs10516002 | chr18 | 2 | 63617950 | 1 | |
| rs12957615 | rs10516002 | chr18 | 2 | 63632560 | 1 | 0.615385 |
| rs1046789 | rs6010770 | chr20 | 3 | 60943041 | 1 | 0.206189 |
| rs16983293 | rs6010770 | chr20 | 1 | 60949501 | 1 | 0.764012 |
| rs6010770 | rs6010770 | chr20 | 3 | 60964670 | 1 | |
| rs2982506 | rs2935888 | chr1 | 3 | 40638220 | 1 | 0.911266 |
| rs2982508 | rs2935888 | chr1 | 2 | 40638875 | 1 | 0.903814 |
| rs2982510 | rs2935888 | chr1 | 2 | 40645210 | 1 | 0.371179 |
| rs2935888 | rs2935888 | chr1 | 4 | 40648700 | 1 | |
| rs2294752 | rs2935888 | chr1 | 4 | 40652539 | 0.906505 | 0.332831 |
| rs7591835 | rs10490066 | chr2 | 4 | 60238756 | 0.876224 | 0.294362 |
| rs6759758 | rs10490066 | chr2 | 4 | 60243358 | 0.876224 | 0.294362 |
| rs10490066 | rs10490066 | chr2 | 1 | 60262883 | 1 | |
| rs11125830 | rs10490066 | chr2 | 3 | 60280209 | 1 | 0.237113 |

Shown is; Surrogate marker name, Anchor marker, Chromosome, the allele that is correlated with risk-allele of the anchor-marker, position of surrogate marker in in NCBI Build 36, D' and $r^2$. Allelic codes are A = 1, C = 2, G = 3, T = 4.

TABLE 8

Key to Sequence IDs.

| Seq ID NO: | Reference |
|---|---|
| 1 | LD block C16 |
| 2 | rs7193343 |
| 3 | rs7618072 |
| 4 | rs4560443 |
| 5 | rs10519674 |
| 6 | rs7733337 |
| 7 | rs1394796 |
| 8 | rs10077199 |
| 9 | rs10516002 |
| 10 | rs6010770 |
| 11 | rs2935888 |
| 12 | rs10490066 |

The invention claimed is:

1. A method for determining a susceptibility to a condition selected from the group consisting of: cardiac arrhythmia selected from Atrial Fibrillation and Atrial Flutter, and Stroke, in a human individual, the method comprising:
analyzing nucleic acid from a biological sample from the human individual for a T allele of a polymorphic marker rs7193343;
detecting a T allele of rs7193343 in the nucleic acid;
determining that the individual has an increased genetic susceptibility to a condition selected from the group consisting of: cardiac arrhythmia selected from Atrial Fibrillation and Atrial Flutter, and Stroke from the detection of the T allele of rs7193343 in the nucleic acid; and
performing an electrocardiogram or initiating anticoagulant therapy on the individual determined to have the increased susceptibility to the condition.

2. The method of claim 1, comprising analyzing the nucleic acid with respect to at least two polymorphic markers.

3. The method of claim 1, further comprising isolating the biological sample from the human individual.

4. The method of claim 1, wherein determination of a susceptibility comprises comparing sequence data obtained from the nucleic acid analysis to a database containing correlation data between the at least one polymorphic marker and susceptibility to the condition.

5. The method of claim 1, wherein the determining that the individual has the increased susceptibility includes calculating a risk score for the individual that includes an odds ratio and/or relative risk of at least 1.10 attributable to the detection of allele T of polymorphic marker rs7193343 in the nucleic acid.

6. The method of claim 1, further comprising reporting the susceptibility to at least one entity selected from the group consisting of the individual, a guardian of the individual, a genetic service provider, a physician, a medical organization, and a medical insurer.

7. The method of claim 1, wherein the condition is ischemic stroke.

8. The method of claim 7, wherein the ischemic stroke is cardioembolic stroke.

9. The method of claim 1, wherein the condition is Atrial Fibrillation or Atrial Flutter.

10. The method of claim 1, further comprising determining at least one biomarker in a sample from the individual, and determining combined risk based on susceptibility attributable to the detection of the T allele of 7193343 and susceptibility attributable to the at least one biomarker, using a multiplicative model.

11. The method of claim 10, wherein the biomarker is a protein biomarker selected from the group consisting of fibrin D-dimer, prothrombin activation fragment 1.2 (F1.2), thrombin-antithrombin III complexes (TAT), fibrinopeptide A (FPA), lipoprotein-associated phospholipase A2 (Ip-PLA2), beta-thromboglobulin, platelet factor 4, P-selectin, von Willebrand Factor, pro-natriuretic peptide (BNP), matrix metalloproteinase-9 (MMP-9), PARK7, nucleoside diphosphate kinase (NDKA), tau, neuron-specific enolase, B-type neurotrophic growth factor, astroglial protein S-100b, glial fibrillary acidic protein, C-reactive protein, serum amyloid A, matrix metalloproteinase-9, vascular and intracellular cell adhesion molecules, tumor necrosis factor alpha, and interleukins, including interleukin-1, -6, and -8.

12. The method according to claim 1, wherein the determining of the susceptibility is performed using a computer-readable medium having computer executable instructions for determining susceptibility to a condition selected from the group consisting of: a cardiac arrhythmia selected from Atrial Fibrillation and Atrial Flutter, and Stroke, the computer readable medium comprising:
data indicative of at least one polymorphic marker that is rs7193343; and a routine stored on the computer readable medium and adapted to be executed by a processor to determine risk of developing the condition for the at least one polymorphic marker.

13. The method of claim 12, wherein the medium contains data indicative of at least two polymorphic markers.

14. The method according to claim 1, wherein the determining of the susceptibility is performed using an apparatus for determining a genetic indicator for a condition selected from the group consisting of: a cardiac arrhythmia selected from Atrial Fibrillation and Atrial Flutter, and Stroke, in a human individual, the apparatus comprising:
 a processor;
 a computer readable memory having computer executable instructions adapted to be executed on the processor to analyze marker information for at least one human individual with respect to at least one polymorphic marker that is rs7193343, and generate an output based on the marker information, wherein the output comprises a risk measure of susceptibility of the at least one marker as a genetic indicator of the condition for the human individual.

15. The method according to claim 14, wherein the computer readable memory further comprises data indicative of the frequency of at least one allele of the at least one polymorphic marker in a plurality of individuals diagnosed with the condition, and data indicative of the frequency of at the least one allele of the at least one polymorphic marker in a plurality of reference individuals, and wherein a risk measure is based on a comparison of the at least one marker for the human individual to the data indicative of the frequency of the at least one marker for the plurality of individuals diagnosed with the condition.

16. The method according to claim 14, wherein the computer readable memory further comprises data indicative of the risk of developing the condition associated with at least one allele of the at least one polymorphic marker, and wherein a risk measure for the human individual is based on a comparison of the at least one marker status for the human individual to the risk of the condition associated with the at least one allele of the at least one polymorphic marker.

17. The method according to claim 14, wherein the computer readable memory further comprises data indicative of the frequency of at least one allele of the at least one polymorphic marker in a plurality of individuals diagnosed with the condition, and data indicative of the frequency of at the least one allele of the at least one polymorphic marker in a plurality of reference individuals, and wherein risk of developing the condition is based on a comparison of the frequency of the at least one allele in individuals diagnosed with the condition and reference individuals.

18. The method according to claim 14, wherein the risk measure is characterized by an Odds Ratio (OR) or a Relative Risk (RR).

19. The method according to claim 6, wherein the reporting comprises making the determination of susceptibility available to the at least one person via a secure website.

20. The method of claim 1, wherein the step of analyzing the nucleic acid comprises at least one nucleic acid analysis technique selected from: polymerase chain reaction (PCR), quantitative PCR, nucleic acid sequencing technology, restriction digestion, specific hybridization, single stranded conformation polymorphism assays (SSCP) and electrophoretic analysis.

21. The method according to claim 1, wherein the analyzing of the nucleic acid comprises:
 amplifying a portion of the nucleic acid that includes polymorphic marker rs7193343 and
 determining whether the amplified nucleic acid contains a T allele of the marker.

22. The method according to claim 21 that comprises amplifying a segment or fragment of the nucleic acid that comprises polymorphic marker rs7193343 by Polymerase Chain Reaction (PCR), using a nucleotide primer pair flanking the polymorphic marker.

23. The method according to claim 21 that comprises sequencing of the amplified nucleic acid to determine if the T allele is present.

24. The method of claim 1 that comprises performing the electrocardiogram.

25. The method of claim 1 that comprises initiating the anticoagulant therapy.

26. The method of claim 25, wherein the anticoagulant comprises at least one agent selected from the group consisting of Dalteparin, Danaparoid, Enoxaparin, Heparin, Tinzaparin, and Warfarin.

27. The method of claim 25, wherein the anticoagulant comprises Warfarin.

* * * * *

SEQUENCE LISTING

<160> NUMBER OF SEQ ID NOS: 12

<210> SEQ ID NO 1
<211> LENGTH: 65839
<212> TYPE: DNA
<213> ORGANISM: Homo sapiens

<400> SEQUENCE: 1

```
tatcattcaa ggctgcacaa acccaagaga aatgaacttg gtcagattct ttgcacttgg      60
cagtttgggg aatgcaggca gaagcagcca ggagccttaa gttttctttt attcacatcg     120
aatctacctg agaacaaatg aagaacatgg tacagctgct tttctctggg cctgtggcag     180
ctaattagag cacctgggaa acaccattca acgttgctgg acagaggtac gtcctcgcaa     240
tgattccgcc aaatggcaca cacaggacaa tggggaaaac ctgtaagggt gaggtgagag     300
ctggccttgg gcgaaggaaa gtttcccaca gcagttatct ccaaaatgac tctgaaacaa     360
ggagtgtgtt ttcctctcgg caggaagaaa accactcggt gggctcacca tcggcagctt     420
gctctggcac gaggctccgg aactggcacc atgacaaaac aaacaaggat tgcccttgg     480 aggctcactg atagggcaac acacacacac acacacacac acacacacac acagcctctc     540
accaacacgg gcacagcgag ttcttcagat atccctggcc tgctggcata aagagctttt     600
caagcagtgg gaagccaaag ggacactcaa caaagcagta atggccactg taaggtagag     660
```

```
acattggtaa aggcatgaaa aggggatgcc tactgcaaaa gcaaaatcgt acacggggtc    720
ttccccatgc cttgactggg caccctcgag agacccettt gggatgtgcg tactaagctt    780
ccacccaact tcctatctgg tggaggcatg ctatgcacag agaccccatc actgaattcc    840
ctcctagata actcactgca ctagactgaa ggcttgagag gttatttca tcatgagtag     900 tcctcaaatc ctagaggccc agagagttgc tcctatctcg attctctttc ttagggtaaa    960
gtgaaccggc agcaagaact accaccagga cgcaagggct tgagacaga ctgaaggggg    1020 catggattct gctggcactc tgagtttgtt tgaaagactt ccaaattcca agcttaaaa    1080 ccctatcagg gccaggtgtg gtggctcata cctgtaatcc cagcactttg ggaggccgag   1140
gtgggcggat cactggaggt caggagttca agacaagcct ggccaacata gtgaaacacc   1200
ctctatacta aaaatacaaa acttagccgg gcatggtggc aggcgcctgt gatcccagct   1260
aactcaggag gctgaggcag cagaatcact tgaacccggg aggcagaagt tgcagtgagc   1320
tgatcgtgcc actgcactcc agtctggaag acagagtgag actctgtctc aaacaaaata   1380
aaatacaata caatcaggag agaggggtgt acaggggaa gagagggat catgaaacgt    1440 gatcacatgt ccccttcttc atggccccti ctccatccca catggtaatt acaaagccca   1500
ttatttgcac tgttactttt aatcaagaaa tccatattga dacatactta ccactggcca   1560
cttcaaagag cggccctgat agttagctaa aataacaaag gaaaatttct tcttgaagtg   1620
taaggatcca agagctcaca cttccttaac cttccagaag ccacccagag aaccaagtga   1680
ctgtgggcaa taattacacc ctcaccaact cagcaaaaat ggcacagatg gtctttctcc   1740
tcttgctgct cccaatgctg cgtttgggtc aacagctgct aagaagaacc accaaggcca   1800
cgttaaatag tacttggatt aattatgctt gaaaatctct tatctgagca ctgctaagac   1860
agaacaattg agtttgggaa tgagtgtggt tacatatttt tccttaatgg cttcctgaac   1920
accctggtta ggtctggtcc caggggagaa attgccagct caagtcataa aatgtgatca   1980
atgtagatca agaccctgtg ctaagtgtct aggatgaaag aggggaagcg tatttgtgca   2040
aacacacaaa catatgaaaa atgcatgtta acataaagaa cttcagcttt ctttctgaag   2100
ctgcaccctc tctcctttca tgcctagagc tctgctcatt ccaccaaaac ttccagccag   2160
cagttctaat cttggacagc gccagaacaa attttggcaa ctgttcctgc agttccaaaa   2220
gattcccatg ttaagccatg gtaagattcg gggaatcaaa tctggatggt gaatggggcc   2280
aatttctttg acttcaataa cacagaggct actggggttc cagccccagt ggtcatagtt   2340
ttaagctcct ctgcataata cttatccaac tactcactgg ttgttctaat gattttttat   2400
cattcgtgcc acaatattta ttgagtgcct acaacataca cagcgcgtcc ctcctgtcga   2460
tacagactcc tacgagcttg ctctcagtag cgtccaggca ggcaaaggaa ggaactggaa   2520
ggcagtgatc aggaccccgg tagaaatgga ctcagcactc cacgtggcca ctgggattca   2580
ctatgtcaac acaattatct gggttactgc tcgcctcatt ccagagtcta cctgctctga   2640
tgccagaatc tgtccttcta ttaacaaggt gtggtcacag tgaactgact gaggtccact   2700
gtgtttaaaa acactgacca tggcatctca tggctggaca agtggcaccg ccgccctgag   2760
accctgcagt gctggggaac ccggaggccc tgagacctcg gttcaactcc gccagtgccc   2820
cgggagttct aaccccacg ggggtctcgc cttcagtcca catgggagtc acccatcaaa    2880
ggcattttag ggatatttta ggttgaccat ttcctgacag cccaacatgt ttttctctgg   2940
gatgaagggc atgccatccc acaaatggtg atgagaaatt gcagaaccac tgaaccggcc   3000
```

```
tacacataag catttcttct cctttgatgt cgagttgaca agaaaggata tgatttcatt    3060
tctactggct cctcttaggt aacccaactg gtttcccact tcctcacctg ccctttgcat    3120
tcccatcctg gtttctttgg ccttggttcc tctttaagct gggaccagcg actttataaa    3180
ctccacacac agtgcagcag gttccagacg cagcgtctgg cctccccagg tcttatgaag    3240
aggtgctgag ggttggcggg ttgacacact cactgcactg cacaaggagg tggctcagcc    3300
cagctttcac gtgaccagtg tccatttata gggtcgcatg ctcacgacac atgctgcatt    3360
atggggaatg ctgcagagag gggagtctta ttcttaaagg agttagaatt gaagcataaa    3420
gtctaggaac taacatgaac cacctcttag aagtctatgt acaacctgca ctcgactttg    3480
agttgttccc caactattag ttccctgtcg tgggtcagtg gggggaaaaa aatcactctc    3540
cacacagctc ttgaggagag gctgggatct ctacgattca cttggtgtct acctgcaggg    3600
gactcaggga aaaaaaagc aaaagccaca ccagcatgag catatcacac agaaattcta    3660
ctgaccccaa aagcggggca atgaaaatct gtgcacaatt tcaaaccatg cacccccaggg   3720 tggaggggag agatggaatt caggggaagt gagaagaaaa aggggaagaa gaaaaggacc    3780
agggattttt tttctttttt cttttttttt tgagacagag tctcactctt gttgcccagg    3840
ctggagtgca gtggcacgat ctcggctcac tgcaacctcc gcctcccagg ttcaagcaac    3900
tctcctgcct cagcctcctg agtagctggg accacaggcg cacaccacca tgcccagcta    3960
atttttgtat ttttagtaga acgggggttt caccatgttg gccaggatgg tctcaaactc    4020
ctgacctcag gtgacctgcc cgcctcatcc tcccagagtg ctgggattac aggcgtgagc    4080
caccgcaccc agcctgggat tttttttctt tctaaggaac tctttcccga gcattcacga    4140
cccagccctt tctgctctgg gatggaaagt gttactcagc tacaaggcct cttgttaatt    4200
gtgggttttt atttttattt cctattaccc tctcacacgc ctgatgagat tattttaccg    4260
gaactgacac agctggaagc agcaggcata cgtggagcct ctgaggaggt gatgcaattt    4320
cattttcatt gatcagaaat cagcaggggca gtaagtgatg ggaaattcca ttagaagaaa    4380
acttgcaggc cataagcctc aacttcccag ccacacccag gacccttcc cccactccct     4440 gaccgaggtc tcgccttcct ctgggctaag tccacactgc ccagaggatt ggaagtgctc    4500
tcctcccaga aaaataaaag accagcgcca cgctgctggc ctaggagagc atcggccggg    4560
ggtgggagac atcgttggac tctgaaccaa caaggcacct cggtgcttct ctatggatta    4620
cagcaaagtc ttccagggat gcagaataaa catccttaca accaatctcc acagccctt     4680 gggatcccct tccaaatgtc aacaaacaag aaaaggggag gccactatac aacagttgta    4740
aagatgtcct ccagccagtc atagagatga tcctgaaggc acttaccatt tattgagtgc    4800
ctactatgtg ccaggcactg tgctaggtgc ttaccatgcc cagactctgg tcctcaccta    4860
accctctagg acagatgttc ttctccctct ctctcctgga tagatgaaga ggcagaggtc    4920
taggaaggta aaggagagaa ccagttggta ccaacacctt cctgagggtc aggccaaact    4980
ctcacaagca gcaaaggaaa gctgagtgtc aacaggagag ctcacacctg agtcctaaga    5040
gagcgtggag cacatgtgat gggctacttt actctttac agatgtagca gatgatagat    5100
tgtgactaat ccacctccat catcctcagc acccaacaac agcgctcctg tgtccaaggc    5160
tggaaccaca ggtgggcttc tcttcggaat acgcagaatg gttactgttt tagcagttaa    5220
gatccctcca actgtttgcc tgccaaatat tgctttgctt acctaaggcc tatgaaaaa     5280 acagcaagga gctcctcaaa aagacaagtt ctatgaaaaa caccaccagc caggtggctc    5340
tccagacctc cacaggccat ttcgccatag gaaagatgga tcacagaaga accagggcac    5400
```

```
agtccgaaat taacactgct ccccacaact cttcactgtt aaaatggaaa ttttacatgg    5460
accagtgatg gcaatgtgtc caaccaaaat ctctcaggaa gcttttattg agtacctaat    5520
ctgtgcctca acaaagcaaa gaatatataa gacatggacc ccgaaatcaa tgcgcttaca    5580
gactaggtga tggccccata agaatacctg gcacacagtt atttattgat cctgtttaca    5640
atatacaata caacatcata gcataaattg aggcccgggc aaaagaagaa agaaaaaaca    5700
aaactggagg aaattttgaa ccaaaaaaat caagcttaaa atgcatgtaa gaataaccta    5760
cacactgagt caaatttggc tctaagcttt ctaaaagtca agaggataaa ggcatgctag    5820
gtatgctttt aaaggtacac tatttacaat gtccaagaga aaaaaaaatc aattggtcag    5880
gattatttag ctccagtaat ttctcaactg ctgagaatgg gataagacta ggtgcaagta    5940
gggcgtgcag ccctatttcc cggatctctt tgtggaggta ataatgagaa ggcttgagtg    6000
tgaggccagc tagtctcact gtttccactg atagacaaga atactgaccc cacagggtgt    6060
tggtggtttg ctgacgtcag agagccggtc agtggcagag ctaggacgaa gacctgggta    6120
tcttcacacc acactaacag tgccttcctc ccacatgaag ctactccgca tcatccttt    6180 aaatccacag gctggctgga tgggtagggg ctcacatgga cgttggggaa ggaggagaac    6240
tgttctagat taaggggac ctaagaacca aacaacagct agatgcgcta tgtagtttcg    6300
tatggatgcc agttctaacc agccaaatgt aaaaagccat tttggggaca atcagataag    6360
tctgaattgc aacttgggat tagatcatgt taataatgtc agttttggcc aggggcagtg    6420
gctcaaacct caagtatcag cactttggga ggctgagacg ggcagattgc ttgagcccag    6480
gagtctgaga ccagcccggg caacaaggtg aaacccatc actaccaaaa gttaaaaaaa    6540
aaaaaacaaa aacagctggg tgcagtggtg tgcgcctgta gtcccagcta cttgattgct    6600
tgagaccagg gaggtcaagg ctgcaatgag ctgtgatcgc accactgtac tctagcttgg    6660
gccacagagt gagaccttgt ctcaaaaaaa gtcagttttg ttagggaata atattatgtt    6720
tacataagaa aatgatgaag cagcatgata tcgttggctt caaaatattt cagcaacgga    6780
caaaaaagac ggaacaaatc tagccaaaag ttcattgtta agtcaaggtg atagaactat    6840
ggaagggttc attatatcat tctttctact tttatacagt aatttttttt ttccttaaaa    6900
gttaccattc gctatcagga acatcttcta aaagaacagc attgaccaga accaagagat    6960
tcagtcttga gtcaatacgt tcatggcaag ccaagccttt tttcaaagaa atgtgggttt    7020
ctcctttctt ccgaagggct ttcctcccag gccgggcccc agctatctct aaagctcctt    7080
tcaaacacca ccatctactg acccccactc ttactccttc tcttagaagg taccaagcac    7140
caccaggctg ctaatgttta aaagaacaca gaaaaagaca atatgcatca cgcctgggca    7200
tagcacctga cagcctttat aagtggtagc tatcacgatc attactgagc aaaaatgcgc    7260
ctgtttacaa aagttaacag cctaaggtta tataacagct tgatttcaag ctttgagcca    7320
aagtctgatt aagaagaata tacatccgtt gaattaaaag cctccacttc ttgactcaac    7380
gggttaagaa aatatttta acactttcag tgagtttaaa aaatcagatg tttaccagcc    7440 attgttttg cgcacactgt cttttatctc agcatgaatg ttttataagc accttaattg    7500
ctttgcaaag cctcaactga actgctccca attgggctgg ttctctagtg tggctctgta    7560
ggtaaacggc ccagtggtaa gtgggcttct ggccatatgt gggcccatac ccaccccaa    7620 catccagcac accctccaac ttcaatacgc atcaccatgc tgcaagctcc ccagaagcac    7680
tctgtgcaat ggacttcttc acggggaccc caatatgtga ccaagggcac agtcacaccc    7740
```

```
agcaccagcc ttccaaaggg cacataacaa tgcttcttcc atgcacacag cgttttacac    7800
attttccttt tttttttttt ttttttttcct gagatggagt ctcgctctgt catccaggct    7860
ggaatgcagt ggcgccatct cggctcactg caacctccac ctcccgggtt caagcgattc    7920
tcctgcttca gcctcctgag tagctgggat tacacgcacc taccaccatg cccggctaat    7980
ttctgtattt ttagtagaga cagggtttca ccatgttggc caggctggtc ttgaactcct    8040
gacctcaggt gatctgcccg ccttggcctc ccaaagcgct gtgattacag gagtgagcca    8100
cagcgcccag cctttctaca cattttcaaa cactctcatt tgacctctaa caatcttttt    8160
aaatagaatg ggaatcatat tttcgatttt acaggtttaa aaaataatt cattcaaaca      8220 tctgagtgac tcctacgagt cattctttct caaggtcctg caactggtta gctgcagagc    8280
aaggaccagg acacaagcta cagtttctac tgtggtgctc ttggctccat gaaggcatca    8340
tttccttaaa gagaatcacc aactcacaga gaaacaagaa gaataaagac agaaacctac    8400
ctgctgcatg cctaagcttc caaatccttc caaaacatgt atcatctaaa tacgagaaaa    8460
agataggatg ccaaagaccc aaaggaggta ttttcattga tcacacctca gtggagtaga    8520
gttatacaca ccaccaaata ttgagttgct ccacacagac cagaacagtg atggcaagac    8580
attaagtcgt aaattttac ataggccaga atggtggagg gcccgagaaa caaatccact      8640
aaagcaccaa gtgctgaagc aaggatcttt ggcccataaa aaagtttaag atctgaggag    8700
tagcctgggt gcaactcctc ctcttagacc ctagactgca agacaacac tgtcatccaa      8760 agcagactga ccactcggct caaaaggcta tttgtaaaaa gatgtaataa gctgtcaacg    8820
tccaggagct cctcatgaag gaggctgaac tcagaggagc tcatgtcaac gcagagttca    8880
ggttaggacc agtgggggta acgtaaaggg tgatttgggc cccaggatta ctgtagcatg    8940
acccaagcaa agtgcacata tctatgtaaa acagaaaaga aggaaaccgg cttcttcccc    9000
gtcaggaatg tcgcttattc tatgggtgtg agcagtttct ttagtccact ttctgccatc    9060
acggtggagc ccttggaagc ccctgttcct accgtgatag aaaacaatga gacttatgag    9120
gcaacttaat aaccactgac caccttctta gtccaactga ctaagctgag tgacattttt    9180
aggaagagca ttaatgcgga aaacaaacct ttccaattca tggaatgagg taatctgggc    9240
agaggaaggg tgggggcaga gtgagtagat ccagaacaca aaacaatgac caggatcccc    9300
gaacatccca gctggaatga gggcaacccc aaaggggtcg acagagaagg cctaggccag    9360
gtgcgatggc tcatgtctgt aatcctagca ttttgggagg ccgaggcggg aggatcactt    9420
gagcctggca gttcgaggcc agccacagca acatagtaag acccccatct ctacaaaaat    9480
taaaaaatta gctgggagtg gtggcaccca cctgtagtcc cagctactca ggaggatgag    9540
atagaaggat cgcttgagcc caggagttcg aggctgcagt gagctatgaa cgtgcccctg    9600
cactccagcc tgggtgacag atcaagatct tgtctcagaa aaaaaaaag agagagagag      9660 agaaaggctg cttaagccat tgctccatgc aactctccaa ccacatgtca aacaccattc    9720
ctaccatctg tccttggagc ccttccctca ccagcacagg tctaactacc cactgccaag    9780
tgtgggtaca gggtaaggcc ctgctcagta agcctgtggt ctgatactaa agtcatatct    9840
tgccattacc ccccggcccc accagttata gtccagaacc ttccatcttg ctgttggctc    9900
tctatggcct ggcttcctga ccctgttttg catgaaccct tgaccagctg gggcttaaat    9960
cccatgggtg ggaatctcat acacctgcag ccttcttgcc tatacctgct cacgctcctt    10020
caagcacagg cctcagccct tatctgaata acctgtctgc tggcttcctc cccatctgat    10080
agtttcactc ctggctcctc tcaggcagca aagaggaata agcaagccac aggctgcagc    10140
```

```
ctggcaagac agtcaggaag gtggcagctg ccctgattca accttcctcc tagtctatct   10200
actgcctctt cctcctccat tccccagtga ctccatgaaa cttgtgttca caaacttgaa   10260
aaattcactg gtgaggccag gtgcagtggc tcatgcctat aatcccagta ctctgggagg   10320
ctgaggtggg aggatcactt gagcccagaa gtttgagacc agcctgggca acacagtgcg   10380
acctcgtctc tataaatcct taaaaattag ccagacatgg tggtgcacgc ctgtgaatcc   10440
agctacttgg gaggctgagg tgtgaagatc acttgagctc aagaggttga ggctgcaagg   10500
agccacgatc acaccactcc actcctgcct gggccaaaga gcaagactct gactcaaaaa   10560
aaaaaaaaaa aattcactga ggagatgtgg tagatggctt agaggtcaat gttataggtc   10620
aatgtccctt aggttgaaca gcacctgtgt tgctgggtct gcaatgttga ggaccccgtg   10680
atggtcttca ataaggctgg ggcgaagggg ctaaacctca ctatcgtgtg caagctcacc   10740
ccaggcctca acagaattta tacatataaa atttatatgc attacatgtt tacatatgta   10800
tgtatacatg tacatgtata tagtatacat atggatatat ttatataaat atgcatatat   10860
acctatacac atatacacat acatctctca tatttaaaac aaaatagagc aattaaaaga   10920
ggaaaaaaac aaagccaaca cacacgtacc cctaccacca ccactacgaa caccaacacg   10980
cccccacagg caagatcttg tcccaagttt ctgagaaacg tcacttaata ctacgtaatc   11040
tcgaaatgat ggggtctgcc tactggcttt gtctggagac tggactccag ctgctctcct   11100
aaactgtcct tgtcaccttc tcatcaggag aaaaggggaa cgtaaacatg aaccacacca   11160
gagatgggct atccagtgag gctgatatca tctcaggcgc caccgacatc tctctccagc   11220
attctgtcat cttatgatca actatgtaac tccagacatc caggggaacc tgaatcctag   11280
aactagatgt ccccaaataa gtggtttctc tgtaaaagtc aaatgtggat cacaaaacaa   11340
atgtgagggg agtcccagga aagccagttg cataagggtg tcctcaatta aattctacac   11400
acgtcaattt ttccccaggg agggcgaggc agagctgaga acaacattgg actggacaga   11460
ctcaaggcag ggaagaaatg gaattttcgc tcttgagatt caaattcctg agtcatagtt   11520
gaaatcccac tgctataatt gttttaatac actgtctcca cacacacaaa aagacgcctt   11580
taaaaagttg tactggcttc cagattccct ggttaaaacc ctcccttctc ctggacgctc   11640
tcagatacaa gctgtgttga actcactagc agctgtcaca ttctggcact tgcttgggct   11700
gtgaccagag cagtcttccg cccaaccagg gaaggcacag gctctgccgg cagagcaggg   11760
gttaatggaa gctgaccgca gcacagttgt taaggtaatc aataccactg agatactaaa   11820
gcagtgtaag ccacaatatt gattgccaag cagatgataa aactgtttat tatgataatt   11880
gcagggtccc tgcaagatgc tcccagcgct tcctaaagct gtttacaaaa ctaataaaga   11940
tttgccattt caaggtcttc cattttaac caccccccac cccgccaact ccccacaatc   12000
tcccactccc aaaaagcagg cctcacccct gggcggttaa catgttcttc ccagggacag   12060
gcactccatg gcccgtcctg ggtggagctt cactctcaga ttctctaaag aacagactgt   12120
ccttctccac cctcaccctg cccccaactt caggaagggg aggacggaag cacagccgac   12180
agccactcag ggccttcaga tttcctcctt aggacccgcc atgtgataat tatgggggttt   12240
tatcgatgga ggggggctgc tcagggctcc ttgggctgac atccatttgt tctaacacat   12300
ttaagaaacc acaccacctt ggtttgtaat taaaacttct ctggagaact tggtggccat   12360
gaagctaact gaacatggtc aaatgctgat tgtagaatgc atttccgcca acactactca   12420
actgtgactt gggctgctga actgggcttg ggtcccaagt tctatcatgc ccaaggcacc   12480
```

```
catttagttt ttattagcag tggaaattaa ctccttcttg gtcacagaca ccaccgtttt    12540
cctcgagacg caagttattg aattatcggc accgtctcca atgctgtcac ctcatgttca    12600
agaggaactg caatgcagac atattttca atataagtag gcatctcgca ggtagtataa    12660
tcatgttctt cggacctctt aggggaaagc cactgggtcc tgcgattaag gatggcagcc    12720
ccaggacttc agggctctgc aaatataccg aaggtgtgtt ttcagagtgt gaaatggaaa    12780
aaacatagaa cccagccagg tgcagtggct catacctgta attccagaac ttttggaggc    12840
cgagtcagac agaccgcttg agcccaggag tttgagatca gcctgggtaa cacgacgaaa    12900
acaaaacccc acctctacga aaaacacaaa aattagcaag gtgtggtggc gagcacctgt    12960
agccccagtt actcgggaga ctgaggtggg agaatcacca gagtccagga ggctgaggct    13020
gcagtgagtt gtgggagctg tgatccagcc actacacgcc agcctgggca acaaagtgag    13080
atcctgtctc aacacaaaac aaagaactca agttttaagg agaattcagt agtcattcca    13140
tcagcagcta gaaggcaagc acccatccct cactcaactc tcatagcagc taagaatatt    13200
ttacctgtaa tagacttcta cagcactagg ccttcaaaac aacatttgca attgaaggga    13260
caccactttg agagctgaca ggccaaagta agatgatgtg gaggctgctt ccacctccca    13320
ccctccccga tcaaagcatg gagaaatcat tcaccagtgc tcctggtctc cgttgccact    13380
gccacctcag tttaggtaga gggacctcta cctgccctat tttcttccca ttcagctgca    13440
accagcagct ctgggaggtc attgccccca cactgtgcct gtgtacacat gtatgcttca    13500
atggtgtgga ccagtacaga catgcagctc ctttatagac atctggttct gccccaccta    13560
ctcccaaaca cacagaaatc agaacactgg agccagtttt atgtagagta tcattcgttt    13620
gccaaagacc ttgccatgaa ctcatggata ccacagcatg gctggaaggg atgcaccagg    13680 gattcctta acctggctac ctgctcttag aggaactatt tggcaaccag gaatggccgg    13740
agggaatctg aggcttccct aggactgcct ttcatgaatc acctgctcct aggcaaagtg    13800
gcaaaggaca gacaaacgcc acctactgaa ctccaagctg gacgccctat tcattcacat    13860
atgctcacgg ggcccatgtt aacaaacacc tccctggatt tgataccaaa agaaagttta    13920
atattatatg tggctaattc tgctgttacc ttttaacctc acttgcacat atctgtcctc    13980
ccaacaataa cttcagcaaa aaacataccc taagaacaat atggtccaca cttggaaacc    14040
cgcccaacag ggccagtcga gcctgcataa gtgctaagaa ccatttagga gcactgtaaa    14100
ccattaaggc cattagctct aatttgacct ccacaaaata catcaaccca ctaggaacaa    14160
atttagaagc tttccaaagt caagttctca aaacctgaaa ggctcataag cacagtctag    14220
ggcagggaac agccagccag tcccggagct actcttcccg ctcccacctt tcctgcagct    14280
gactgaaggg tgcatgctta gctggtacac ggacccaaga tccttctcca gccactggat    14340
caggaagctg tggccatcga ggggtcgata tgcaggctgg aacccgccaa acatttctga    14400
ttaagggatt cactccagcc ttcctctgag ctcacaccat atacaatctt ccctctgcac    14460
tgctctaaat cacttctttt caaataacgc ggatttctgg attcatttcc aagtgatcct    14520
gattggaatt caattgcact aactgggtcc ctgcaacagg tcagggttca cccagtctt    14580 caatctataa aggcaggtat catgtacatt aagagccatg attcccccac attaatacat    14640
gtgtcaacac aataaataat ttctccaaca aaacttataa ccatcagcat atgctataaa    14700
tttaaattgc aaaatcatca taattttca tctttattct tcactgataa ttactgactg    14760
cattttttaa tactgatggc atcatcttga tgaggaagca ggcaatgaaa taaactacgg    14820
tactggctag gcacagagat cacacttaca attccagcac tttgggaggc caaagtggga    14880
```

```
ggatcacagg agccctgag tttgagacca gcctggacaa catagggaga cccatctct    14940
acaaaaaata caaatattag taggaagtgg tggtgcacac ctgtggtctc agctaagaga    15000
ggccaaggca agaggatcac ttagcccaga agtttgaggc tgcggtgagc caagatcaca    15060
tcactgcact cttggcctgg gcaagacagc aagacgctgt ctcaaattaa aaaaaaaaaa    15120
aaattaaaac agagccaggt gcggctgttc atgactataa taccagcacc ttgggaggcc    15180
gaagcgggtg gatcacctga ggtcaggagt ttgagaccag ccaggccaag gtgaaaccct    15240
gtctctacta aaaatacaaa tattagccag gcgtggtgct gcatgacagt aatccaagat    15300
actcaggagg ctgaggcagg agaattgctt gaacccagga ggtggaagtt gcagtgggcc    15360
aagattgtgt cactgcactc cagcctgggc gacagacact ctgtctcaaa aaaaaaaaa     15420
agaaaccatg gcactatcaa actccaccag ccaatgcgag aagcaggcta agaacacgca    15480
tactaggtaa gtggacagtg cacatggata agtcaacaat ccttcagttg cttcaatgac    15540
aaaaacatac cacatactta tttcactcat cttttccaggg cagaaggaag aaataagtgg    15600
gaagaatatg gccaaatga gttagcagta acaggagaag caagatgcag cacacagagt     15660
tctacagccc aggaagaatt gccaaaagct gagtaatcca ttccagctcc accctgcatg    15720
aatttccagg tatcaaatta tatgttaatt atgcggacgc agagttatat gtggggaagt    15780
ggtgttagtc agcacccaag gggtggaaat tcagtaaaaa tttagttttg tcaagtatgt    15840
ttcatgcaca ggcctggggc tcctctggct caggaaaaga gaaagcagga gtcaggaggc    15900
ccagacctt ccctaacagg gtcccacagc caattcgctg gccctctcta gaccaacttt     15960
cccgaattat aaaataccac aaggttgggg tttttttccc cccaccgttt ctgttcaaat    16020
caaaaagcgc taagtcctgg ctgatttctg actcagccag tcaaaagagg gacacgcctc    16080
cctaactgca ggagggtggg gaagggcagc tgcactcagt ccgatggagg ggaaaccagt    16140
aaacccgtcc cttggcactg tcacttggca atttctgagg tttaagacga cacggcgttc    16200
tcccaggtcc tggcctgtaa atgccaggga aacgcattgt acttgtgaag agagagaaca    16260
cagagtttcg aaactgctct aaagcccatg tctcaggctg caagaacgtt atcagtctca    16320
cacatcgtgc ccctgcctcc aaggccccca tcaccacata ctgatcttgc cctgatttga    16380
agcgggcggg agagagctat ggggaagtcc aggcctgtcc cagccacgga tgggacaaac    16440
agacaggaac tgagtgctga agaccttgct gtagctgctg agcgatctta aaagggatcc    16500
accctggagg agctgagcac cctcttcttt ccagttctcc tcactttaaa cgatttttgt    16560
ctaataatgt acccaacagg cagatatcag agaagcacta aactaacacc ttgaaatggg    16620
tcaataatgg ctgggcgcag tggctcatgc ctgtaatccc agtactctga gagtccgagg    16680
caggtggatc actcgaggcc aggacttcga gaccagcctg agcaacatgg cgaaaccctg    16740
ccactactaa aatacaaaaa ttagccgggt gtggcggcac atgcctgtaa tcccagctac    16800
tcgagaggct gaggtacaag aatcgcttaa actcggagg cggaggttgc agtgaaccaa    16860
gatcgcgtca ctgcactcca gcctgggtga cagagtgaga ccctgtctca aaaaataaaa    16920
ttaaaaaaaa aaaagagag agaaatgggt taatgacaaa gaagtcctat acacagcata    16980
gtatgtactg tatagcatta ggataatata gtatagcagt cccttatccg aggcttcatc    17040
ttccatgacc tcagttaccc acattacagt acagtaagat attctgagag agaggagaga    17100
ccatattccc ataactgtca ttacaggata ttgttttaat tgttctattt tattattagt    17160
tatcactgtt aatctcttac tgtgcctaat ttataaatta aattttatca taggcatgta    17220
```

```
ggtagagaaa aaaacatagt ctacctaggg tttgatacta tcctccctct cagacattcc    17280
actaagtgtc ttggaatgtc tccccaagga taaagaggga ctgctgtcgt ggctaggagt    17340
atatgctctg agctggcatc ccagcgcaga ggccatttaa cagcagcaaa tttgctacag    17400
actttgggcc tcaagttcat cactcatatg atgggtgtag gatcatcttt accccatagg    17460
gttgtaagga ttaatgagac agtgaagtat ttagcacagt agatgcttaa tagggttag     17520 ctattaatgc ttatattaat atttattaac atttatacag acaaagaaca tgttctcatg    17580
tcatttgcat agcaatccaa caaaggccgt attctcactt ttgaggctca gagaagcaga    17640
gagacttgtc catggtcaca cacaagtact cagacttcca ggccagtgtc ttttccatca    17700
tcttttttca gggtgtttca cccacgcaac actggccagg ggctagatgg ttccaggtgg    17760
gagtgggtga actttgtaca ttctggtcat tagccagtca atgtttatct gagccaatcc    17820
aaccagcacg agcctgtgat tcctcagaca caattgctcg ggatgatgct aaggtgggta    17880
tttgtggtta taacggagga tcccgtgaaa agaaaaatgt aaagcaaata atacagtata    17940
ggcagtacaa agaaacaaca gaaatgatgc cctgagttgg gggcagaggg gtctcttcca    18000
ctctcagagg ctgtcgccga actgatcttt ctcacatagt caaccattaa aagtccccaa    18060
cccacaggtc ctagtttctt ctaagtatcc atctccctcc ttgctagagc agagcctcca    18120
aaatgaaagc gtttctccgc cttcctccag gcctcctgag aaaggttatg agatgggtta    18180
tcagcctctc tgacctctgc agccatcaac agcacttctg cctctcccat cccccacagc    18240
gaggatccta cagcccagag ccagcttccc tgccttcccc cattaatgcc tttcccctcc    18300
aacagctatc acaagagggc tgtttagtga gaggacctcc ggctgacctt tgctgacagg    18360
ctccaagctc tccctgtaaa cggatctaat gtgaggctgg gtaattagca accaagtagt    18420
aattgcagct tctaactatg ctcggccaag attgcaaaaa ttccctaggg gggtgcctcc    18480
tagggatccc aacccacaca aaggcattta ctcacagcca aaagagggga ctcagccaca    18540
tttctcatgg aggccagcac ttctctaggt cttaattaaa gtggcaccca tgtaaagaga    18600
cagacagcaa aaggaaatta gcaaataaag gagactgacc aagaaagaaa tgtatggctt    18660
gcttggaaca gcccattcag aaaggtacaa cctctcaagg tggatggccg tgcacacgaa    18720
actcattcca gccgcggaag gaaggcacca aagagccttc gagggcatc aaaaactgca     18780 gaaaggccag gcgcgatggc ccctgcctat aatcctagca ctctgggagg ctgagacggg    18840
tggatcacct gaggtcagga gtttgagacc agcctggcca acatggtgag accccatctc    18900
tactaaaaat agaaaaatta gccgggcatg gcgctaggcg cctgtaatcc cagctactcc    18960
caggctgagg caggagaatc gcttgaacct gggaggtgga ggctgtggtg agccgagatc    19020
gcaccactgc accccagcct gggtgacaga gctagtctcc atctcaaaca aacaaacaaa    19080
aaaaacaaga actgcaaaaa ggcaggacac atgaagacag gtccccggc ctggctggcc     19140 agcctggctg cctgctccta tcacccactc aaccaaaatc actcctcacc caagcaccct    19200
gtatggccca ctgttcgcat cacaagattc tagatgccag gccatgtggt ctatgctaag    19260
agatccgtag tatcatctgc tatgatttgg tgattccacc agacctgtcc acaggccccc    19320
ctaccgttag ctgcctacat gtattaacat gtttcagaat aacgtgcaaa atccccattg    19380
agaaataaag atgtgagcac ttccaaatag agcagctgcc ctcctcatga ctctaaaaat    19440
acctaaaact gcacaaaaaa gaacattgtc agacgaaaag aatcatccct cctcactcta    19500
acaggacaac aagcgatgcc caacagcaca gcagcgcctg tttcatcctt cctaagaaaa    19560
ccctttattt ttcaagccca ccactcccca ctccaatttc ctttatctgt tttgtactta    19620
```

```
aaaagtcact tcactgaact gctgtttgct cacgataact cctgaacctc tgtcctcagg   19680
agaggcggca agttcagggg gcatggtagc tttcccacgt ggaccagact ttctgccaac   19740
ctgaattaca ccctagacgt cttcaaactt catttcctct gccactgtgc tgcccgatcc   19800
cccaatgcat tcggggctgt agagactctc tgggttgaat ccagttataa aaccagggt    19860 agcagcagcc gagtgcacta attcaccctc catttccttc tccaaacaat taatatactt   19920
aataactcca gccccgacga cagatttctc agacacccct ctattaacct ctccccgcta   19980
caagcagtgg gtctccacca gaattcttct gttccctatc acttaatcat tttttaatcc   20040
acaacaagga ctttgtgcca cactgtggtt ttgttctctc ttaatctttt ataagggacc   20100
ttatcaaaag cttttagaaa atacaagtga attttgccta ccaggtcatc tttattattt   20160
tagaattctt tatgaagaaa ttatagactt taacattgta aatgaatatt taagactcag   20220
cattcactta gacatgcaag tctggctcag gttatattta agtcgctgta ttacttccac   20280
cttcagaagg attcttgtct gcctcctggg atggaatgac ttcccctccc caagccccca   20340
ggtgccattt ctgggattcc cccaagactt tctggaccag ctgaaattga gtccatattg   20400
agtaccaatg ggacttagag tgcattaaca gaacctcaaa ccaaggaaca aaagtcatcg   20460
agccaagggg gcctggctat ggcagcctat ccgactccta cctcctctac ctttccccag   20520
gtggatggca gggagcagca ggctcccctg cctcacagct ggcccgcaca tctgcaggga   20580
gccaatgaca gcttcttgat gttgacatca cttaggctgc ctcctaacac ttgtttgttg   20640
tagctattat ttctaattag cacttctcaa cagaaccagt gctcagcacc aaggttcctc   20700
ctgacggaac aattaaagag gcacaagggg cgggggtgtt tcctaaaatt attctcttgg   20760
caggtttcaa ggtaaatcat ctagtcaaat gcacatctct tcaagagctg cctgtggaca   20820
gggttgaaaa gctgtagcaa tattccggaa cccctgtttg aaagcattcc catcaagtta   20880
aatgaagggt taaggtaatc caattacacc aatgtgtttt cctgatcacc aggggaatcc   20940
tcagccttcc ccgtaatctg ctcctaacgc cccatttagt ccaatgctgc actccaatca   21000
ccaaaaatgt agacagggtt cccactccta cagccagatg agaggtgcct gccccttctc   21060
caaaatggga tggtgaaatt aacacatttc agaaaatatt ctacagagtc cagagtccag   21120
ggcacgcttt atccttgagg aaaataataa atgtcgagtc ctaatggcat gtcaattaaa   21180
ggggtcacca taaacaagct gttcaaactt tcccctccac tcttcgcccg tgcctctcca   21240
atctgggtgc cctggaggac ggaacgggaa ctgcagatcc aggcactcca ttatggcaac   21300
ccagcaagca gttcagcacg gacttaatga gctcttggaa ggaaacagga agtctataaa   21360
gtaatttaaa taacttccag tcctgaaata aaggaaatta aaccgctggc acaaacctct   21420
ctgatggaca ccttctttgt ccctccgatc acaactacaa ctacagcggt catattgctc   21480
tccccaagac caggccccaa attcccctaa tatgaaacac aaaggctgtc agtcctcaga   21540
gctctccaag ctcctgcaga ggcttaagcc atggatgtgg catggtgtgc agcaagaaca   21600
cgggaatccg cccacaaacc ccgcgctggg tcctgccact ccctagctgc aagaccttgg   21660
gccaatcatg caacttcaca gggcctcagc gtttcaccat caacaaagga aagctctggg   21720
cctggccaaa tgacttctaa gattattaag agggtcaaat gagcacatat gagaacagcg   21780
ccaattgaaa acacaaataa acgtcggtat tttccagctg cccagggcct taggctccag   21840
aatttctcga tgttctgctc aggaggcact gtcctatctt ggtaattatg aaggcatatt   21900
catacgttct tttactgcca ggtgcggtgg ctcacgtctg taatcccaac actttgggac   21960
```

```
accaaggcgg gtggatcacc tgaggtcagg agttccagac cagcctggcc aacacagtaa    22020
aaccctgtct ctactaaaca cacacacaca cacacacaca cacgagcc gggcatggtg      22080 gcgggcacct gtaatctcag ctactcagga ggctcaggca gaagaatcac ttgaacctgg    22140
gaggctgaga ttggagtgag ctgagctcgt gccactgcac tccagcctgg tgacagagca    22200
agactccaac ataaaataaa taaattaatt aattaattcg ttcttttgct tctcctaagc    22260
ccctcagtgt agatacttat ttgcatggac aatgatcagt ccaactaagc atgattttct    22320
tatcagcaga gactgtgtct tctcatcttc tgtaaaccag tgtgcccaga gccagagcac    22380
caagcagcca agaagctggt cctcaataaa gggctagaat ctataaccca tgcagttatc    22440
cagacatcct taagcaccaa aatgctaaca actatccatc aactctctac aaaaagagac    22500
aaacctaata acaagataaa ttccataact ggttgtgagc ctacaaggcg gggaggggct    22560
gggggcgtgg gaaccccgcc tgtgcaactc cttgcattac caggccctgc cctgagtgca    22620
atccaaccac ggagttctgg cagtttcacc tggtaaacct aagctgctgg atgctaagga    22680
ctgtttctgg ccacagagtt aagtttactt tgttgataat aatcagccag atatggactg    22740
gtctgaccag tactccggat ccaggatcac aaagaaaaga caaacttaaa agaagcttaa    22800
ggtcagcctc gttttgctag ccctctaggt attactactg acaactggta tggtcaaccc    22860
ttgaccccta aactggtaaa agccaagagt aaggctggac attcagtgtg gccaagaaag    22920
ctacccagct tctgggcaga agcgcaagat cctggtgctc cggaaagaga accgttgggc    22980
ccggctcaaa aacagaccct cccaaaccaa ccctgagaaa ggaaatcaca aacagaaatc    23040
taacttttct ataagggcac actgcacaag tgttcctgca gcttcacaaa caggttctgt    23100
gggaatctgc tctatcgctc ccatctgtca ctggcggggt aagatctgtc ttgcatatca    23160
tggcggtctc catcccactg gagaattcaa tggtgctgtc ttgcatatgg gctgtgaaac    23220
ttgaacaacc ggattctgag ggtccagacg tctctgtttg agcaacagct gccttccttt    23280
aaaggtccca cagttgagca atagagttct ttactcaaga gggctgttcc aagtcttgag    23340
taaccaccct tgccctcaag ggttccccag ggtgaagccc cattgcctct gcctcaccaa    23400
ggaggcagcg actcagtctt ctcgctacac atctgtctcc tcactttcca gtcagatcac    23460
agccagtggg acacaatctg acaaagttct gtctaaggtg gggtaatctg aaaagcaaat    23520
acagatcatc tcccccaga cttattcaca gcactcccca ctggagccag gtttgacttt     23580
ccacaaagtt cactggccag aatcataacc cacacatcta tggctcttcc ttctttaacc    23640
atctttcatg taaatccttc atctaaaagg ggaaccacct atctatgaac tttaaatttc    23700
ccagtatcca tgttaaaaaa ggggaggggc ctggtgcagt ggctcacagc tgcaatcctg    23760
acactttggg aggccgaggc ggcaagatcg cttgagccca ggagttccaa gaccagcctg    23820
ggcaacacag ggaaagccta tctctacaaa aaaagaaaaa aattagctgg gtgtgatggt    23880
gtgcacctct ggtcccagct actcaggagg ctgggatagg agaattgctt gagcctggga    23940
ggtggaggct gcagtgagcc atgattgcac cactgtactc ccgtgattta aagcaagacc    24000
ctgtccaaac aacaaaaatg aaaacataaa aacaaaaaaa taattcaagg ctaggtgcgg    24060
tggctcacac ctataatctc agcactttgg gaggccaagg caggcagatt acctgaggtc    24120
gggagtttga ccagcctg ccaacatgg tgaaacccca tctctactaa aaatacaaaa        24180
attaaccagg tgtggtggtg catgcctgta atcccagctg ctcaggaggc tgaggcacaa    24240
gaattgcttg aatccaggag gcagagtttg tagtgagcca agatcatgcc accacactcc    24300
agcctgggca acagactgag actctgtctc aaaaaataat aatactaata agggaaaaa    24360
```

```
agaaacaggt gaaattcatt gtaatatgtc ttatttaacc gaatctgtct acacattatt    24420
tcaaacgtaa tcgatctagg ttttattaag acagtttccc cttgttttcc tactaagcct    24480
gggaaaactg gtatgtgttc cacactcaca gtatggctca gggcgaacca gccacatttc    24540
gggtgcttag gggccacata ctgcagtaat gtaaaaccct ggcttcctct aatcatgaga    24600
acctaaaaca taactctgat ctggccccac tgtaataatt catgcttgta gttctcactc    24660
acagacttta cagaacttac cgctgctcaa gactctttcc cacggcatta acaattatat    24720
ttgggtgaca tgtcaagaag ttaagctgcc cgggcctgga gttaacagat tttcacagaa    24780
ttgtgtacaa cttatctggt ccatcagatc gtctctctgg ggcttgtcca ccattaaact    24840
agacccctgg ggtttcttaa tttaaaatcc tcataaccct ttaacttgaa aactcactgt    24900
ctttgcaatg acatgtggtt aactctgtag tagccacata aacatctcct cattcttaaa    24960
caggagactt ccattttgac ctaatctgag attattctga attatttctg ccctagtcac    25020
atgtacgcta cagacatgag attacacaga ataatcaact gaggtggtgc ctacacaatc    25080
ttttgttttt ttgttttgag acaaagtccc gctctgtcgc ctaggctgga gtgcagtggc    25140
accatcttcc ctcactgcaa cctccgcctc tcaggttccc aggttcaagc aattctcctg    25200
cctcagcctc ctgagtagct gggattatag gcacatgccg ccacacccgg ctaatttttg    25260 tattttagt agatacaggg tttcgcatgt tggccaggct ggtctcgaac tcctgacctc    25320
aagtgatcct cccacctcag cctcccaaag tgctgggatt acaggcatga gccaacatgc    25380
ctggatacct ggaaaatctt aaggcacaaa caaacacagg acaaatccac aggcttggga    25440
atcactataa gcagaagaaa aatgtccaca gggcataaac tttggaggca tgctcacagc    25500
aaccgctaac cagaaaactt cgcaggctca gtccagatct gggcaggatt ggctcagggg    25560
tgacccatct atcctgagag ctgtcaggac cccatcctat tgggcacgat acaagtcaga    25620
catgggacag ccttcgatgc cagcgtgggc aggggtctca cctgagccca cgagaccaca    25680
cacactttgg cagcaactct tgaatcagtc aattttcttc acaccataag tacatacttc    25740
actctctccg ctcagcagct gcacctgccc tatctggtgg agtggaggac actggcaagc    25800
tgaaagcttc tgcaggctca tccatccaga ttcagctcta agagcagggc aacccgggga    25860
aaatggaaac atacagaaaa cagttcactt ctggcttgtc gctttggctg caggcaagag    25920
aaggtgtgca cagagttttg aaggaaagac tggaatgggc tgacactggg ctttgttccc    25980
ggagccccat ggggacaggg ctggcttccg aacctagaaa tgcagagagc tgctctccaa    26040
caggtggagg gcccacccga gtaagtatcc cgggcagaag aacagagcag gcaccactgt    26100
ctgtcaacac caggctcggc atcctcccat cccccagggt ccctcgacct gtccccaggg    26160
cactggagag aggagggagg gacgaagggc acgcggtgaa aggaaggaag gaggcgcctc    26220
ttcttggcga gctgatgggt gtgagtggtg agcatgaatt aaaaagccat ccgggaacaa    26280
tggtcttttc atatttggag cctgttctgc acaaagctca gcttgttcta gtgggaggac    26340
tctgctttcc attttttttcc taactcattt cctaggggttg tggcaatgtc tggcactcgg    26400
ctcaacccaa tagagtatcc tttaactgaa ggatgtgcca ggcaggcctc ctccttgact    26460
tcgtaagtgg tggcattgag acacacaaaa agggacaact tcaggaagct tttctgtctc    26520
gacccgtggg ctcccaaaga gctcctgggt gtttctctga atagctgcct aacccacaga    26580
aacacacact ggatgttttc agcggccaaa cacccatttc cctctcaaat tacgctagac    26640
atgccacacc cagcagacac tccaaagcct aactggaaaa ggacagcgga tgggcgtcag    26700
```

```
atcatgtgac aagaccttcc tccacgttcg acacactcct ggagtctctg ctgaacccca    26760
caaacccctt aggcaaagca attttgaaac tggggtgga gacaagaaca gcagccaaca     26820
ctaagcaatg aagctgttcc tgacacttga acaaactgtc gcctcactca gtccttatga    26880
tccctggtgg gcagcctcta agccagatcc tccaatccca ccccgtggca ttcacaccct    26940
tgtgtagtcc cctcccttg ggagtgagca atacataggg actcacttct taccaacagc    27000
atgcaaatgg aataggacaa atgtgatagg acaccacttc tgagatgagg ctgcaaagaa    27060
accgtcattt tagtcatctg caccttctc ctcctcctct cccttatgga agccaagtgc     27120
cccattgtga gctgctctgt ggtgagaccc acatggcaaa gaactgagag cagcctccag    27180
ccagcagctc ttggggaaat gaatcctatc aacaaccgtg tgtgtgagca cagatttcag    27240
tctgtcccca gtcaagtctt cagatgagac acggcccca ggtaaacact ttgaccttgc     27300 agcagggac ccagctacgc cacagcccga ttcctgaccc acagaaactg taagataata    27360
agtgcttgcc attttaagct actgaactta ggggtaatct gtgatgcagc aatagataac    27420
aatacacatc tccattttgc aaatgaaaag atataatgga ggccaggagt gctgactcat    27480
gcctgtggtc ccaacacttt gggaggctga agtgagagga tcacttcagc tcagaggttc    27540
aagaccagcc tgggcaagat agcaagactc tgtctctaca aaattttttt taaaaaaagg    27600
ttagccaagt gtggtggcac atgactgtcg tcccagctat tcaggaggct gaggtggaag    27660
gatgccttga gcccgggagg tcaaggctgc agtgagccct gactgcacca ccacgcactt    27720
cagcttggac aagacagtga gacccttcaa aaaaaaagg gggggaaaga aagaaaata     27780 tataattttg gccagtaagt agcagagatt ctcacttagg ccagactgac tctctctagc    27840
caccttcctc tcaccatgtg gcattaccta tcaagcccac attccggtcc atagaccaga    27900
aaagcagcaa aactccctgg gcctctctcc atcctcacag atgacagaga cacctaacag    27960
tcatgccccc aaataaaagg ataccagatt gctttggaat tttagggttg aagaaagagt    28020
gaggagagaa tccagtctaa ctttcttta cagataaagc atctgagacc cacagccata    28080
aagtaacgga catggaactc aaaccccgc caggatagca cgtgactctt tagggattcc     28140
aggaaacttc tactcaaaca tgctgaacaa gcttctactt ctctggccag gagaactcca    28200
tcagtaactc tggtcttctc ttttggcaca ccaagattaa tgctctgtgg tggctggctc    28260
ccctggcact tggcagcttc tcctatacct gcccctaag tccttccaca aagtgacgag     28320
atagagaagg tagatcagag cgtcttctcc ttggttaata ccagaatcga catatcacat    28380
atcacaactg catactgccc acccagctta tgctgaggtg tgatctaagt ttgctttgaa    28440
attcagtgac atatcagaaa gacagcacac acatttccat caagacagct aacttgggca    28500
aaggtgttct caagtaccca aggcgattga ttccacaagc ttgcagatca ctaagacttc    28560 cactatttt acaaacacat accatagatg cttacagtaa atatcataaa taattaaagc     28620
taagtagcct aaggacattt tgtgaagcat ctttgctgct tttttttaaa ttaggttctc    28680
gctaattcac aagattgaat aatctccaaa aagcctccaa acacagccac aggccagtgc    28740
tatttaagtg attctacatt tttgcaaact tttaagcaca tattttcttc tcatgacaaa    28800
aagtaataga tattcactat gcggagctca gaaaacaaag tattaaaagt agcctgtact    28860
tctaccagct ggaaatagcc atcagtcata tgtaattctt tagcttctct tctatgcata    28920
ttttaaaaat taaactgaag tcctatagtc cacagagttc ctttcattcc atttacatca    28980
ctgttttccc acatttataa ccaggaggca ggagttttaa atagctgcat aagcatctac    29040
catatggctg caccacagtt taaatcaatc ccctgtaaga ttttttcagat agtttccatt   29100
```

```
tttcactatt ataaatgtct gttataagtg tctgtagcaa aaatctttat gtataaattt   29160
cctttgcacg actctcaggg tttccttatt acaaatggag ttgtcaccag tcctgatccg   29220
ggtattagac gtaagataat taaagggaaa aaaaaaaaaa aaccatcaga caaagactcc   29280
gcccttgtga agcttagatt ctgcaggggg aaacaatcaa ggataataca tttttttgcta  29340 ggcacaatgg ctcacaccta taatcccagc actttgggag gccaaggtgg gtggatcatc   29400
tgaggtcagg agttcgagac cagcctggcc aacatggtga accccccccc tccccacccc   29460
gccccatctc ttaaaaaaaa aaaaaattag ctgggagtga tggcgggcgc ctgtagtccc   29520
agctactcag gaggctaagg caggagagtc gcctgaacca gggaggcagg gattgcagta   29580
agctgagact gcactactgc actccagcct ggacgaaaca gcgagactcc atctcaaaaa   29640
acaaacaaac aaacaaaaag gataatacat tttttttaatt gtatagtatt ttactagtgg   29700
catatggtat ggtcagaaat gcagaggcag aacagagtga gggggtcagg aattcacggg   29760
gggaaaagct acacatttaa ataaaccctta aagtttcttg acacatactg ccaaatgatc   29820
ctccagaaag ggtatactaa ttttttatacc caataaccag atcagggtat ttgcttttttt   29880 tttttttttcc acttagttca aaaaaacaaa acaaaacaaa aaaagctcaa ccttaccagt   29940
aatcaaatac gttaaaacaa tgaggtctca tttggctctt caaatgggca gcctagattt   30000
attcttcatg aattgtccat ttgtgttctt tgcccattta tctctttta ttttttgttta   30060 ccacaataat aactacataa aaacacgact tttttttttt ttttttttttt ttttaagtag   30120 agacaggtat cactatgttg cccaggctgg tctcaaactc ctgggctcaa gcaatcctcc   30180
cacctcagcc tcccaaagtg ctaggattac tgtgcctggc ctccattttt ctctatctgt    30240
atgcatcaat ctttttttttt tttttttttt tttttgaga tggagtttca ctctttcacc    30300
caggctggag cacagtggtg caatctcggc tcactgcaac ctctgccttt tggtttcaag   30360
ccattctcct gcctcagcct cccaagtagc tgggattaca gatgcccacc atcacgccca   30420
gctagtagag atggggtttc cccatgttgg ccaggctgtt cttgaactcc tgaccttgtg   30480
atgtgcctgc ctcaacctcc caaagtgctg ggattacaag tgtgggccac tgcacctggc   30540
tgtttcattc atttttaaga gctctttata tattaaggat ttaggacaca ctgtcaattc   30600
catgtgctct aaacaccttt tcacagtttg tcatatgcct taaaattttg tgattagtga   30660
ccagcatgca caatttttttt taagtagact acatcaatct tttctattac aatttcttcc   30720
ccacaaggct taggcctaat attcctcact gccctatatt cagatcaata ttaacctata   30780
ttttcttcta gctcttttgt gattttagtt ttacttttac ctctccaact cacctggaat   30840
ggatggtaac atatgctatg aaaatggct ctaacctaat ttttccgcca tttggctatc    30900
taactgtcct acaaccattt attgcataat tttataatac gagaggcagt gaagtgcagt   30960
gatagagatc actggttttg ctgtcagtta catcagtgtc caagtctggc tgactttgag   31020
cctgttactt aaactccctg agcttcggtt tccttcacta taaatgaac tattagtaat    31080 gtattagtag tatccaattc atctggtttt tatgaggatt aaataagttc atataaagtc   31140
ttggtctggt gcagtggctc acgtcttata atgccagcac tttgggaggc caaggcggga   31200
agataatgag gccatgagtt tgagaccagc ctggccaaca atggtgaaac ccagtctcta   31260
ctaaaaatac aaaaaattagc tgggcatggt ggcgcacacc tgtagcccca gttacttgag   31320
agactgaggc aggagaactg cttgagcctg cagacaaag gttacagtga gccaagatcg    31380
tgccactgca ctccagccta ggtgagggaa caagactctg tctcaaaaaa agaaaaaagt   31440
```

```
tggctgcgca ccatgggtca cgcctgtaat cccagcactt tgggaggccg aggcgggcag   31500
attacgagaa caggagatgg agaccatcct agctaacaca gggaaatccc gtctctacta   31560
aaaatacaaa ttagccgggc gtggtggccg cgcctgtag tcccagctac tcgggaggct    31620
gaggcagaag aatggcgtga acccggggagg cagagcttgc agtgagctga gattgtgtca  31680
ctgaactcca gcctaggcaa cagagcgaga ctccgtctca aaaaaaaaa aggtcttcag    31740 cataatgctt ggcacttaga agttctgaag cgttatgtga gctgttactc tgattcctct   31800
cacttaacat gaaatacaac ctttaccaga cacatttcta tttgattcca tcccactgag   31860
tgatctctat attttctaac cagttttttcc cagtatatga gaaagctaat tatcttttaa  31920
aatgttacgt tgtaactgaa ctccttaatt aaatttaaat gtgtcttggg ccactaggaa   31980
gacagtaaca tctggaaata attttctttg tttctttttta accattattt gactttggtt  32040
tgtccatcct gaccagttca ataaggtagg aaaagaaat tagcaaatta gtatattcca    32100
tagtctccat tgtgttccca gtttcagaat gttgcctctc atgattcatc actaagtctg   32160
agggtgttgg ctgcctgttt cttcattgag aagtcaatgc atcctctttc aagcttgagt   32220
tttcaaaatt ctaagcagac taggaataag ggtagaaaat taccaaatgc agtcaagtgt   32280
gacggctcaa gcctataatc ccagaatttt gggaggccaa cgcaggagga taacttgagg   32340
ccaggagttt aagaccagcc tggacaaacat agtgagaccc caatctctat gaaaaaaaaa  32400
attaaagccc agcatggtgg tgtgtgcctg tagtcccagc tactcaaggt gatgcaggaa   32460
gactgcttga gctggaggtc aaggctataa tgagccatga ttgcaccact gcactccagc   32520
ctaagcaaca aaacaagaca aagaaagaaa agaaagaaaa gaaaaaaaag aaagaaacga   32580
aagaaaagga aaggaaaggg aggaaggaaa gaggaaagga aggaaaggaa ggaaggtgat   32640
caaatgtatc tctcacacac atacacacag acagacagct gtcccttgct atatctccca   32700
tagatcccga aaatctgagg atagtcaagt ccctgatata aaacagcata atatgcacaa   32760
cctcctgtat actttaaatc atcttttgat tacttataac acctaatgca atgtaaatgc   32820
tatataaata tttgttaaac tgtatcattt aaggaataat gacaagcaaa aaggctgtcg   32880
agtccacagg tccttttacat gttgagtaaa gacccaattt ttttccccaaa tattttttgat 32940 ttgcagttgc tggaatctac aaatgcagaa cgggtgacta tgaaggccaa ctatattatg   33000
tttttcttct tggctctaca tacatgatta tttcaagaga agacattctg atattaagcc   33060
ccttcttaca tttccaggat aaatcctatg tggttatgat tcttttaaaa tgctaaattc   33120
aatctgtgac tgtttatct ggcatttttg catctccact catgtcggaa ctcaatcttc    33180
agctttcttt ttgtgtaacc tttgtgatgg tgttggttcc cagaattatg ctagctttgt   33240
caaatcaact gggatgcttt acctcttttt ctattccctg aaacagtgta tttagcaggc   33300
aattatagca tccctctaag tttaaaataa cttatccttt aaacttcttg catccagagc   33360
cctcctcata actgttttttt gttttgtttt ttttgagacg gagtctcaca ttgtcgccca  33420
ggctggagtg cagtggtgcg atctcggctc actacaatct ctgcctcccg ggttcacgca   33480
attctcctgc ctcagcttcc cgagtaactg ggactacggg tgccaccac cgcacccggc    33540 tgatttttttg tatctttagt agagactggg tttcactatg ttggccagac aggtctcaac  33600
tcctgacctc gtgatccacc cgccgcggcc tcccaaagtg ctaggattac atacaggcgt   33660
gagccaccgc gcaaggccag aactttttttt ttaatgctca gcttcttccc cagtttctga  33720
tttaaagttt cagacatcca agtcatttcc caacagccat gtcactggga ttttcaaagg   33780
tgttgcattt taagttactg tgttttacat tacaaaacaa ttacttcaaa tgcaacttac   33840
```

```
atttgttaca cttttttctat catatcaatt ccttttttagt tttctgtatt tggggttttc   33900
tcttttctct tttcttaatt aaacatgata gtgatttggt ctacttcctt ggccttttt    33960 cccaaatagc ttttagattt atcaattcag tgtttttatc tgtttttcta attcattaat   34020
atcactttta tcttacaatt ctttttctcca gctgtcttta ggcttgtttt atgctttcca   34080
agtttgagtt gaatacttaa ttcatttatt ttcattttct ttaataatgt tttaaagcta   34140
caaatgtgcc cctgaatata actttggtaa taacccatac atttagatat acagagttct   34200
caatatttcc taatgatcct gtaacagtaa cttcatttcc tctttgaccc aagtgtgatt   34260
taggagaata ttttaaatt ttcaagtaac tggatttcat taacatgttt aagtattcta    34320
tggaggataa aaacatctct gaaaggagat gaaactctgg caaataaaaa aaaacctttt   34380
aaatagaaaa cacgacaatg ttaaaagtga aaaatgactc atataatgct gtgatggcca   34440
tatctacaga cactccttgt agaagggata taaccaccat tggtcctggg gcactgagag   34500
atctgagtgt aagcaacaca aggagagagg gaagaggatg ttaagtctct gtgccttctg   34560
aaaattttat cttgggcata tgctgcttgc ttatttcaga agcaaagtca cccctcaata   34620
aatggaataa aaccatccca gatacaccat ctaagtatat aaccaagtaa acttccatat   34680 tttttttgatg aaatttagag atggcttcaa ttgagtaaga cttggcccca agatgattac   34740
atctgtgact aaagaaggca ggagggaaaa acaataatct ctaattctgc aatctccaag   34800
ttcagaagaa ttgagagcta caagaaaaat aaagtatata cgtgtgtgtg tgtgtgtgtg   34860
tgtgtgtgta tgtgtgtata tatatgttaa aaagcttaat gaggttccaa ctgggctatt   34920
ttgaaaccta aatgtcagga acatgaagct gaggcagtac agtagccagt tccctgtatc   34980
tccttacgca gcctttccca ttttacaatt actacatctt gtagatcttg cctgctacag   35040
accttaaaac gcatttcaat cccaaattaa ttgaattaac ttgtgcttat aagcatcata   35100
ccgtatcaac tcccttcctt cccacaaact ttgtagtgcc aagttaaaaa gaaaagaaaa   35160
aaaaatggac tccataaatc agttttccaa tttacgttga agaaatctgt ttcctacttt   35220
ctaatttctg caactgggaa attctgtata ttatgttacc atataatgaa ggatgccggt   35280
aaacagaaat ccacacgcct gcacacacaa cagattacat tgtatgtaat tgcaaacacc   35340
accaagttat gtactcttgg gagcattatt agtgagatgt ggttatttaa tgcttcatct   35400
atttaaaaaa aaaactcatt ccatatggat gaaaaatgag tatactagcc tgaatatggg   35460
aaaaaaatag aaaatgtaat catatattac ttaaaatcta taacgttta tgcaaagata    35520 aggtgttagt accaaactta ggcattcaga atgtctcaaa tacaatatca tgggctaatt   35580
gctggctacc aaaacctcca tcccccagca gcagatggca gggccagcct tttgtacttt   35640
acttgaccat ttaagaaact cacaaagggg ccagtcatgg tggctcacac ctgtaattcc   35700
agcactttca gaggccgacg caggcgaatc acttgaggtc aggagttcga gacaagcctg   35760
accaaaatgg caaacccccg tctctagtaa aaataaaaaa attagcaggg tgtggtggcg   35820
cacgcctgta atcccagcta ttcaggaggc tgaggcagga gaatcatttg aactcaggaa   35880
gcagaggttg cagtgagccg agattgcatc actgcactcc agcctgggtt acagagcgag   35940
actccctctc aaagaaaaaa aaaaaaaaaa aaactcataa aggtacacag cacctggggg   36000
cttccattag catcagaaca cccacggagg cacgccccat gggaaggtgg cactcagctc   36060
ccaccacaga gcaaggccct ttaacagcga agatgctgca gggcactgct actcgccctg   36120
ctggggagaa gccacccagc agccacccta ggagcctggc acagaatgcc cagctgtggg   36180
```

```
gaaggaaact gtgccacctg catcgcccgt gtgccaaatg gagttcaaga ctctgcaccg    36240
ttccccattc atccccacga gaggttcagc agccactgcc gctaaaacaa aagacggatg    36300
acaggaaaac ccgctggcct ttggcccatt ccctagcaaa ggggaagtgt aaaagtgcaa    36360
aggggaaagt gggccagctg cactaatccc tctttgtcca gcagtaatta atagtataat    36420
ccacatttca gatgcattaa agcgaaaatg ctgcattatc agagagcccg gcacacagcc    36480
tcagggcaga gcctccctgc tgacctgcag aaccaggtta cctcatctca gcctcctcct    36540
ctcaggggag ctgactctag acacctcata aaaggaccga gctggcagcc agaagtctcc    36600
actctgcctg atgtgctgtg tctgtcttca gaaaccaccc actccagagc cagtcctttg    36660
ggcacacgag ttctactcca ggagacattt acatcaagtt ctactctctg accaacattg    36720
aacattttat ttttatttta ttttttaca cagagacaga gtcttgctct gtcacccagg     36780
ctggagtgca ctggcatggt catagttcac tgcagcctcg aactcctggg ctcaagtgat    36840
cctcccaagt ctacctcccg agtagctagg actacaggtg tgcaccaccg cactgggtta    36900 atttttgtt tgttttattt tgtgagacag gtctcactc ttgtcatcca ggctggactg      36960
gagtacagtg gcgtgatctt ggctcactgc aacctcgacc tcccgggttt aagcgattct    37020
cccacctcag cctccccagt agctgggact acaggcatgc accaccacac cgggctaatt    37080
tttgtatttt ttggtagaga cggggtttca ccacgttggc caggctggtc tcaaactcct    37140
gacctcaggt cgatccgcct gcctcagcct cccaatgtgc tgggattaca gacctgaacc    37200
acttcacctg gccctggcta attttttttt ttttaatttt ttgtagatat ggggtttccc    37260
tttgttgccc agcgtggtct caaactcctg gcctcaagca atcttcctac cttgaactcc    37320
caaagcacta ggattacagg cgtgagccac cacacccagc aacactgcat atattaatat    37380
cacaagtctg ggctgggcgt ggtggctcat acctgtaatc ccagtacttt gggaggccaa    37440
ggtgggcaga tcacgaggtc aagagatcaa gaccatcctg gccaacatgg tgaaaccctg    37500
tctctactaa aaatacaaaa attagctggg cttggtggcg ctactcagga ggctgaggca    37560
ggagaatcac ttgaacctag aggcagaggt cgcagtgcat ggatatcatg ccactgcatt    37620
ccaggctagt gacagagcaa gactcaatct caaggaaaaa aaaaaaatca caagcccccc    37680
tgtggattct taagctttaa gctaactccc ctccccccaa aatactggga taataaatgc    37740
aaccaaaatt aagatgcccc tcctcaactc aattcggtgg gataccttt tttatcttgg     37800 tgttatttgg gtattctgca ctaattctgg ggcaccaggt aagtttctat cgaggggtag    37860
aagctgactt ctgtccccgt cccccaagac caaagaggaa gcctcttctg ccaccactga    37920
aatactatct ttagaggaag gcatgctatt agctcatcaa gcacaaaaca cattcgagct    37980
aaacattaca gtcaaatgtc acagccactt caaaatagag gtacccaaaa aggcagtcag    38040
tcttctcagc agggctttga aaccactgcc aactgagaac ttgatctcaa gtcttccaac    38100
accaaaacac ctggtggaat aggtacaact aacgggcaga cagcctcaaa ctccattcag    38160
ctccacagcg cctctccatg accactgcag ctcaacctct gtgctgggaa gtgcatgcat    38220
aggatggagc catgtttcta gaaccatcag agacaaattt tctactacaa gtgatactgc    38280
acatgacagt ttattccttg gctggcctct gatagtatgc atttgaacca tatggaatca    38340 ccatttttt tattaaatta gagctgttaa ataataacat catggaggaa tgtgttaggt     38400
tctgggcaag gatcttaaat acacagtttt ggaacaagtg tagggagggg cccaagccca    38460
cggccggtgc ccaacggtgg ctacacacta cagcagcaac cggccttcat cctccaagtc    38520
ctccttggaa tttgggtgaa actacttata tcttaatcta ggcagctgga gatgaagaca    38580
```

```
aagacaaaag agaagaggag agaaaaggaa aataatttga tagaagtatt ttccatccca   38640
aattttgaga tcctggcacg aatgatataa tctagatacc caacaaccta tacttgttcc   38700
aaaatcgtgc tgttaagatc cttgcccaga acctaacacg ttcttccatg atgttattaa   38760
caactctaat ttaatccaaa aatggtgatt ccatatggtt caaatacata gtatcagagg   38820
ccagccaagg aatgaattgt catttgcaat atctcttgta gcagaaaatg tatccatgct   38880
ggttctagaa acatagctcc atcctatgca cacacttccc ccaggactcc tggactgcca   38940
aaggcagcct ataagccatc aactagcaac tggacatttc atctgggcgc tcaggaggta   39000
cagacctacc aatcacggga gtgaaggtac ccaggccaag gggctgtaca agaagggcag   39060
agaggaggcc accatcctga acacatcaca gactgcccat ctgtgccctt caagtgacct   39120
ctaaagtgtg gtatcaatct ccactgaacc tttgctctta ttcccacaac acttggattc   39180
tttctttaca gggacccatg tgaaaactct ttatttttt attattatta tttttgagac   39240
agggtcttgc tctgtcgccc aggttggagt gcagtagtac gatgttggct cactgcaacc   39300
tctgcctccc tggctcaagc gatcctccca cctcagcctc ccaagtaact gggaccacag   39360
gcgtgtgcca ccacacccag ctaatttttc tattttttgt ggagacaggg ttttgccatg   39420
ttgcccaggc tggtctcaaa cttccaggct caagtgatct gcctgccttg gcctcccaaa   39480
gtgctgggag tacaggcctg aaccacggtg cctggccaaa aacccttat aaacactctc   39540 ttttattttt ctctcaagta tgactctttg ggcctcacca aaatacaatt tcacaaaata   39600
atgtcacatt atttggggga ggggagaggc caccaaattt catctcgaag cctcttccct   39660
catttccaag gaaataggca ttgttggaac aggtaaggct gtaatatttg gtttagcttt   39720
gccctcctga gccacctacc tctagaggca cgtggggggtc tctttctttg ccaactgcac   39780
caattcctcc acaggaccgt gcagtagctg aataacaacc cccgaagacg cccacatcct   39840
aatatccgta acctacaaat atgttaccttt ctacagcaaa ggaaactttg cagatgcgat   39900
caagtgaagg atctttggat agaggagatg atcgtggatt atccaggggg cctgatgcaa   39960 tcacagggt ccttacaaca ggggcaaagg agaggacaga gtcaggcaga agaaggagat   40020
gtaacagaag catgacacag agtgatgtga ggaaggggcc atcaacccag aaatgtgggg   40080
gcctccagaa cctagaccat gcaaggaaat gggttcctcc tcgaaaccgc tacgagaaag   40140
cagccctgcc aacaccctga cttcagccta ctgaaactga tttcagactt ctaggctcca   40200
gctacaaggc aatcagtttg cggttttttg cattttttt tttttttgga aaaatgaaag   40260 ctgatttta ttttatcatc aacagccatt ctttagacat gaacatgcat acgtaatatt   40320
ctatgcacac atcgcagttt tgaacattag ttaataaagt ttaaacatac tacatcctta   40380
cagaaaacat caaaatgcaa acttaagttt gtgttttaca ccaacaagtt tgtggtaatt   40440
tcttcttctt ttttttttt ttttttttt tttttgaga cacagtctcg ctctgtcacc   40500
aggctggagt gcagtggtgc gatcttaact cactgcaacc tccgactccc tgcttcaagc   40560
gattctctgc ctcagcctcc tgagtagctg ggattacagg caggcaccac catgcccggc   40620
taatttttgt attttttagta gagaaggggt ttcaccatgt cttgatctcc tgacctcatg   40680
atccacctgc ctcggcctcc caaagtgctg ggattacagg catgagccac catgtccggc   40740
ctatgtggta acttcttacg gcatcaagag gaaactagta tagccatctg gagaaagggg   40800
gacagaacca ctggacacac agaagcaggg gtgtccctga agggttcacc ctaccaaggg   40860
gttcacacta ccctccttct ccagacccta gggaccagct gaaacctctc tttctccatc   40920
```

```
accaaaaatt aggaccaaag gcctcagatg ctgtaatcaa gagctgtgtc tttttttttt    40980
tttttttttt ttttgagata gggtctcact ctgtctctca agctggagtg cagtggtgca    41040
atctcaactc actgtaccct ctacctcccg ggctgaagtg atcctcccac ctcagcctcc    41100
tgagtagctg ggactacaga cgcctaccac cgtgcacagc tagcttttgt atttcttgta    41160
gagacagggt tttgctgtgt tgcccaggtt ggtctctaac tcctgggttc aagtgatcca    41220
cccacttcag cctccataag tgctgggatt acaggcgtga gccaccacac cggccacgag    41280
ggctatgtct taggagaggt gttcagtgga gtatcttagc attagacaga aaaaacctcc    41340
catcctggcc taccgcattt gagatttata aatatccaaa ttaaccaagg aaacaacaga    41400
aaaacagtag ttggacaaag agtttgtgtg tgctacatgt ttattttatc taataggaga    41460
caccgaacta gaaacatcta cattcaagaa gaatccctgg atccacagtt cctttttatca   41520 attcacaaaa gccaggccga gccaaccttt cccaatatat tccacaggtg ggcccgcctg    41580
aagcctcgct gtgatgccag gcagccagcc tgaagaactg gaaagccagg gcccgtgcac    41640
gctgggctcc tgaagacaaa ggaaacagaa tggctcggga aggccgtggc accctgcccg    41700
cctccgtggt agcctggggc cactggatct tgctgtctcc gcagcacctg agaggtgtga    41760
gccaggcagc caaccacatc agaagctggc tgccggctgc cccaattgca caacacctcc    41820
aggggagcca gctttccagg actgggtttt acacaccata cgggcactgg ccatgttgac    41880
ccagtcaagg catggcacct tgaagaatgg cccacgcaaa gaccggccat atggacagaa    41940
ggcatcctgc cacagagcga tttctgaatc acctctatgc aaagaatagt cttctctctt    42000
acgcaaagga gatcccatca ccaccatctc atttctatcc caggctcctc cagttctctt    42060
tcaatcacaa gccagactac ccaaccactt aactctctag gcccagatat gacttaattc    42120
tcccactcct gcatgtttgt tgccacttcc ccattttgtg ttaacaatta acctgaagta    42180
ttatgttaac aattaacatg aattgtgttt tggttttttaa ggtcggagta actaggatta    42240
ctcaatagga tttaaatgtt caattttagc acacatgtac aaggcgctac tttgtacatg    42300
acaagatgaa gtggtttaaa aaaaaaacaa aacataacca cctttcacaa agggttctca    42360
ttcagcctcc tgcttgtgaa agatacgact ttgaatagtg aaagtcccaa gaagggtaat    42420
tcaagcaaaa ctggtttcta gtttgccttg attcaaattc tttatgctac ttgacccatt    42480
tctcttttcc tcttgcttct cctgatgcct ctcaaaataa taataaacca accccagaaa    42540
tagaatcctg tcttccttag atgtcaccat atgactaatt tatggccttt gtttaaagcc    42600
cttacaccag agttgactcc agtaatttcc tcctcttcta tttgaatgtc catttacagc    42660
ctctctgtaa cctctgggtg aactgagaat gttctctgtg cctctcatga tgtggattcg    42720
caccctggtg acagcagagt ggctccgagc agaatctccc cattacagct gaagcccact    42780
gggaccctac ccaagttcac gtgtatatcc caagagagtt tgctgaacac tccttatgcc    42840
ttaatgcacc tttgaaaaaa aaagactaa ggggctggg cgcagtggtt catgcctata     42900
atcccagcac tttgggaggc caaggtggaa ggttcacttg agcccaagat ttcaagacca    42960
gactaggcaa tatggcaaga cctcatctct acaaaaataa aaataaatca gccaggcgtg    43020
ggggcatgtg cctgtggttc cagctgcttg gggtgctga gcaggaaga tcacctccct     43080 cagccttggg aggttgaggc tgcatggagc tgtgattgtg ccactgcaat ccagactgag    43140
caacactgca agactcccat ctcgaaaaaa aaaaaaagg caaaaagata tcaaaggctg     43200
agtgggcaat ttgaatgtgt tcccaagacg tgatgggaat tttctacgtt tggattcagg    43260
ggagtggggt cttagttttg ctctcattca gggaggtggg tcccaaaaaa tatcccctgt    43320
```

```
tggccttagg aggaggaata cttgaaaggt atatctgaaa atgctccaag ttttttcctg      43380
ccccgctttc cagtggtgcc cttcgccaag tcatgaaaac tctgccaaca ctgttctctc      43440
tccagcactc acctgggctc cccaccaatg tcttggctgc cgtcacgact aaataatgcc      43500
ttctcttctt cccctccacc caccctctc tggtctttag cacaacctat cagctgactt       43560
ctccaactcc agggagctag accacatagt cctccaccaa gagctttgct agcttagcac      43620
cccacagata gagctcgtcc agagaattgt ccaaccatcc attaaaatat ccaagtggcc      43680
ccagtgtgcc agagactgct ctctctggac tagggctagg ggtaagcagc aaaccaaaca      43740
ggctaagacc tctgccacct gcatagagcc catgcctact gtctgaccca tccctaccct      43800
tgcagatgct ccttaattcc ccacttttac tctctcctct tcagaaaatg atttcctcct      43860
tttggatgaa aatttgattt tttcgatgaa gtgggaccta tgttttctca gttttatct      43920 tttttttttt tttgagacag ggtcttgctc tgtcacccag gctggagtcc agtggcacga      43980
tcatggctca ctgcagcctc aatttcccag gctcaagcaa tcctcccgcc ttagcctctt      44040
gagtagctgg gactacaggc atgcgccatc acacccggct aattttgctt gattttttt      44100 ttatagagac agggtctcac tatgttgccc aggctggtct cgaactcctg ggctcaagca      44160
atcctcctgc cttggcctcc caaagtgctg ggatgacagg cgtgagcata cacgcctggc      44220
catggttttg atcttataaa ataaattaac tctaaggccg ggtgtggtgg ctcacgcctg      44280
tcatcccaac actttgggag gctgaacggg gtagatcatg aggtcaagag atcgagacca      44340
tcctggccaa catggtgaaa ccccgtctct actaaaacca caaaaaatta cctgggcatt      44400
agcctgtagt cccagctact gggaggctg aggcaggagg atcgcttgaa cccaggaggc       44460
agagactgca gtgagccaaa atcacaccac tgcactccag cctggcgaca gagtgagact      44520
ccatctcaaa aataaaataa aataaaataa ctctaaataa taaatggcaa gaattttctt      44580
taattggcat tttgtgggga ttcaccccag gcttggctgt gtgttatcat actctcttca      44640
ctctgagaat ctgaactgtc tccctgaagg actgaagcta gcctctgtat agtctaaatg      44700
ctaaaactgg ctgtcagttt cctcaatgct tgccactgtg attttattct gaaagctaca      44760
gctcttctca ttcaaaggtt accctccctc ctaaccaacc cagaaagaac tcactaccca      44820
gctctgcttg caccctagtg ttggggctca agcttccggt tccgctaaga ctctgacctc      44880
gcttctaagg acacacacct cagaggccca gagctccgct gtatcacaca ctcattgtca      44940
catccctcga tgcatcattc ccagaatcct caaggctgtc actggatgaa agaataaaac      45000
agcaaaacat ccggcacctt ttcatcctgg ctcaagtcaa aagagttggg attaaagcca      45060
cttgtgactt tcaaaagcta tcactacgag gcaaggaccg agtggccagt tcgtttcaga      45120
aagtggcctg atgctgttga aactgccagc tgccagtgga cgtgagcctc actcccactt      45180
tatagtctca ggaaggtggc tctcaggaca tgacgccaag ccccagaagg gcctctgaat      45240
cctccaccag cgtgtgcgtg tgtgtgtctg tgcgtgtgtg tgtgtgtgtg tgtgtgtgcg      45300
tgtgcgtgtg cgtgtctgca cgcgcacctg agtgcacatg ggctgcctgg tttacaggcc      45360
accacaaccc ttccaccaag tgtgaacaca catacacttc cttaccaagg tgcccaccgg      45420 aaaccctgc ctggaccct gcagccctcc cagccacact gcagcatcga gggaacagca       45480 cttttgcctcc ccaaacctgc cctggctact gggtgacccc gctctgctat ccccaccttc      45540
accctgagat gcagactg tctgctctaa agggcatgaa cctggagatt gtgagtcatc        45600
acgacgcgca ggaagcaacg tctcagtcca aaccctgagc ccgttcctag agagccttct      45660
```

```
ccgctctctc acccctcatc ccacgtagag caatcagggc tcacccgccc ccttcccttt    45720
ctctatggct tcttcaagat ctcctcatcc atctgcccac aactggaact gtttatttgt    45780
ttagcccact ggtaagaaaa atgagagagc gggctggcat tcctggctgg cataaacac    45840 gttttaaaa aatgtctgtt ccaactctgt ctgggtcccg tactgagccc tttaacctcc    45900
tgcaagcacc atggagacat tccatgggaa ctatcaccat tcgttatcat cgctgaaaga    45960
caaaatccac tgtaccctgc aacatctcac acagatcctt cacattcttg gtttgagagc    46020
tgactatgca agaaaaagga agcaccatga ctgtgggaaa ggccactgtc accaggacaa    46080
gaggcaccag caagagccct gcatcaatta ctctacagag gcaccgggag gcctgatttt    46140
aattttttaa aaatacattt aatgaatcac atacgcaaac tttacattgg cagaacactc    46200
ccttaggatc atgagcaaat ttctgatcag atcaaatagc aaactgccca aggaaaccac    46260
gaagaggggt gatgttgcta tcacactatc aaaagtaaa gacatacttc tgatttctca    46320
caagaaattt cccaacaaaa gctctctgtc ttagattccg aaagaaaaac atcccccaca    46380
cagagtgtaa gggccaagaa tggcctcacc atatgggaca gcttctgaaa tacacagaaa    46440
acgggcaacg cgggacccat gggacaaacc actgtgtagc cagctgcccc ggccaggccc    46500
gtggtgttga cttggcagt gcttgtcgac catgactcag caatagtcat cgaaactgaa    46560
atcaagtgga actgatcagt tcagacctcc aatgttgagt ttgactcaac gattcttcaa    46620
tgcccctggt cttcctgaaa ttctccattt aaatatttac tggtttaagg gtaaagtcag    46680
ggaggcacgg gcatggttgt tggaccttt ctgtcttatc ctattcaaat ctggctgaac    46740
tgagtaaaac gttatgcagc aggatgtctt cctatataat ccacttcatc ccgcccccc    46800 aatactcttc catagggggtt caaatgcaga tctgaaccaa ctgctcgatg atccccccaa    46860
gccatttagt ctctgagctt ttctcatcta caaaatgaga tgtgtcccca ctctgcatac    46920
cgtatagagc acctgcaagg attagttgaa agggtatagg cccaaggact ttgaaaaatg    46980
aagctcctta aattattttc ccgatgtcct cagacagact tggcacctta cccttttact    47040
cataattaaa gatttgagca gctaactcag aggcctaatt gtgatgctaa gtagacatat    47100
agtggctcaa taaaggaaa gactgaaggg gtttagagca gcgaggaaag acaatcgagg    47160
aaacggggct cgaggttctg ggacgagggc ctgctgagct ggccagccca gccaaggcca    47220
cagggataca gtccttccag tcactcaagt taaaaatctt gcagtcaccc ttgactctat    47280
gtcctgtctt gtcccatatc tcccttcaaa atctatccag aggataagca cctggagcag    47340
atcgaatagc atccctccta gaactcatgt ctaccaagaa cctcagaaca tggccttatt    47400
tggaaataga gtctttgaag taatttataa ctaaattgag ctcagactag atcggggtag    47460
gccttaaatc aatgactgag ccaggtgtgg tggctcacac ctataatacc atcactttgg    47520
gaggctgagg tgggtagatc acctgaggtc aggagtttga gaccagcctg ccaacatag    47580 tgaaaccctg tctctactaa aaatacaaaa attagccagg tgtggtggcg gcacctata    47640 atcccggcta ctcaggaggc tgaggcagga gaatcacttg aacctgggag gtggaggttg    47700
cagtgagcca agatcatgcc actgcactcc agcctgggtg acaaagcgag actccatctc    47760
aaaaaaaaaa aaaaaaaaaa aaatcaatga ctggtacct tagaagagga gggaacacac    47820
agaaatgcac acaaggaaga cagccacgtg tagacggag gcagaggctg gagtgacaca    47880
gctccaagct aaggaatgag tctttactca aatgtcacct tctccgaaag ccttcttca    47940 ctgtgtccac cgaacctgcc aactactgct caccccctgc cctcgtcccg cctcctctcc    48000
acagcattta acatcatcca aaatactata atgcacttag taatgatgtc cagtgaggga    48060
```

```
gatgaggtag tataagctcc aagcagacaa gcatttctct cttttttttgc ccccattgga    48120 gtatcaccgg caccaacaac agtgtctggc acacatggga ctctcaaaca aaaggtcaag    48180
ggcagcccag ggaagcccca aggctggaag ctctcgctga aaagccagg ctgggagaag     48240 cccgtctccc tgagtcaggc ctgcaagcca ggcaggcaga tggtgaaagg caggagggag    48300
aggagccact gcaggcccct ggtcagcaga acaagaagaa tacggagccg ggagtttgag    48360
ggcagcacca ctgatattca ggctgtgtca ttcttcgttg gggatgaggg tggctgtcct    48420
gggcatcgca ggatgtttag gagcatccct ggcctctaca ctggatgcca gtagcatcct    48480 ctcccccaaag tgtgacaacc aagaatgtct ccagactgcc aaatcttggg gggaggaagc   48540
aaaatcaccc cctacggaga accgctgaaa ctgagtttca gtccaatgac ggcccacatg    48600
ccacgatccc agacagcaca gggccaagca ggtaacacaa atgagcgaag ttggctggga    48660
aacaggacgt ggtagggtaa gagctggtaa gcaacagtga gctctggcaa cctaaaaagt    48720
agatgttcct tccacaaggg gcagtcacca ccctgttcta gccaggtttt gccctgaaga    48780
cccaaaatgg ccaaatcccc cgattttttt tttcaagaga aggttttaat actgattttt    48840
ctgtgaaatg tgcccatgtt taaaacatag tatgtggcca ggtgcagtgt ctcacgcctg    48900
taatcccagc actctggaag gccgaggcgg gcagatcact tgaggtcagg agttcgaggc    48960
caacctggcc aacatggcaa aaccccatct ctactaaaaa taaaaaatta gcctggcgtg    49020
gtggcccatg cctatgattc cagctactca ggagcctcag gcaggagaat cgcttgaacc    49080
tcggaggcag aggctgcagt gagctgagat cgcactgctg cactccagcc tggcgacaga    49140
gcaagactct gtctcaagaa taaataaata aataaaataa aatatagtat ttgctgaaca    49200
aaacacatct acaggctagg ttttgcctac aagctaagac tgtgcaacct ccgcacagag    49260
actgcctgga ggtggaaggg gctggaggga acccccctt aggagcctgc tgtcatctag     49320
acacaagggg cctggagcag gcctgtgagg gtaaggggcg gagggaggaa aggctggatc    49380
ccagaaactc ttaaggtgaa taagataagc acagcaagac aagtgtgcac actgtaatca    49440
taagccacga gggccaaagc aacagccaat gcccccggct ccctcccacg atgcgctaca    49500
ggcagcactg tgcttacgca ggtcacacac ctaggagccg aagacccct aatgcatcct     49560 tcaggtagga ccctctgctt tgcagaaaac cagcgcttag aaaaggctta aagtgagtat    49620
tttgaagacg gctggaatca gagctcaaat ccataacctc aaaggcttca tgtcatcttg    49680
ccaccaccca cgccaatcct tgagcctaga gtaacgaaga gaaaggctgc aacgaccaca    49740
cacaccacga cgtcagccca aaggccacgt ggctccatcc acggcaacaa aatgcaaggg    49800
agctccgagg gacacttccg tttcaggaca ggcttacggg gaggacacca gctcctccca    49860
ccctatctgt agactgggta gaagggcttc ttttgagcgc tctgtcttcc cagagaagga    49920
cgtcctggaa acaaggcacg tgcagtatta ccattaaaca acatgcacat gccagtggcg    49980
ctaaataaac agcagagaca gaggctgcct cacccacttg ctccatagtc tgcatcgaat    50040
caaggtcact ggagacaagg taaagtccac agagccccct catctcacat ccacacagct    50100
ttgctcctcc tgaaagaaat gaaatagctg gagtgttttg gcaaagaaac gaagaggcag    50160
gtgagcaagg agagatgggg gaaggagggg gcgaaagaag agaagaggca gccccatctc    50220
ccagctgggg agaaacttcc agatgggagg cagcagacgc cactgaattg atggccagtc    50280
tccaccaagc ctcatcatgc cccgcaggca aagtctccac tccccttcct tcccccagcc    50340
acgggcagga ggcaccaccc atgaagactg agtctgagat catgcaccat tgactaccca    50400
```

-continued

```
agcccaattc ttcctgtccc tgatctccaa gtggtagctg caaataagcc cacgtgagtt   50460
gcactgaaag gatcagggca ctggttctcg aggactggga atgcaatgat aaaacgaaat   50520
ctcaccagca ctcagtaaag ccagatccaa tggcagcctt gggctggtca ccctaaaacc   50580
gccatgtgtc agtcgggttc cgcctcccag aagcgggtta ccctgatttg tgagctgatt   50640
attctagaag actccagggt ctgaaagtat ctcaacaggt tggctatgta aaaacacagt   50700
caatcaagca gccagacact ttgcagagag actccactcc acgaagaatt acaggaggac   50760
cagagggtct ggctgtgccg gatcccacag ctcagcggct acatgtcccc cagaaggtgg   50820
gcccaggaag gccctgcacc ttgtatggga agctctctac tccccaacac aatacccctc   50880
ggccttgact gccccttaga caccgcctgc ctcctggaga cgagacattc ctcagccctc   50940
tcccacatat gatctccgca tgtatccatt ataaggatct aactttttta tggagaggag   51000
aaagttccca catgcagaag acttacaccg caggggaac gaagggaggg tcatttagca   51060
cttgttgaaa aagatgagt atgagagcaa ttgggaggag aagaaaatgt catgtcagct   51120
atgaaagtta aacaggaacg ttcccctccc cacaacgacc gccctgcacc gccctgcccc   51180
aagtccttcc caatgcggcg gcagccacca gcccatgcag gactcacaca tgggcagaca   51240
cccaagttaa gagaggggc ccgggaaggg gagggacacc atggtggttt gcagagctcc   51300
acctctggga atggatttga tgtcaagtgt cagcaagtaa attgctattg cttctcaat   51360 aagcagcagc agtgagttaa gtgtttcccc gtattgtgga gccctcacgg actcgataca   51420
gcagtattga cagcacaatc acacagtaat ccagggtcct ctaatgccta cacttcctca   51480
atgaaaatac actttccact tggacatcag cccattagct ttgggctgga atctctggcc   51540
tccttatccc tcccccaggc acccctgggc tgcaggtctg gcatctggcc ccctgacacc   51600
ccagccaaca tgaacatccc agccagagta ttgtcagggc ccaaccgaaa aagataaaca   51660
gtcagagacc tacaggaaaa ggcctgctct ccctgtctat aaatcactgg tgggaaggaa   51720
agaaaagtga tccaactctt tcaggataaa aatcacagca gtcactgagg aaaattgatg   51780
ttcccttgca aagcgaaaga tgttctctcc gggaagatgc atgccttcaa gttttcagac   51840
agactgagac tcaaacttca cccaatgtga cacaggattg agacaagtta tgtgacctcc   51900
acaaagctca acctctcacg ccagattcga tgcttcccaa aaggaacaca cccatgtctt   51960
ggcagtctcc gataggctga aatagtagag ggtctgctgg gcacagtggc tcacgcttgt   52020
aatcccagca cttagggaag cagaggtggg tggatcccat gaggtcagga gttcgagaat   52080
agcctggcca acatggcaaa accccatctc tacaaaaaat acaaaaaaaa aaaaaaaaa   52140 aaaaaaaaaa aagccaggtg tggtggcagg cgcctgtaat cccagcaact gggagggag   52200 gctgaggcag gagaactgct tgaacccagg aggcggaggt tgcagtgagc cgagatcaca   52260
ccactgcact ccaggctggg gggcagagca agactctgtc tcaaaaacaa aaacagaaag   52320
gccagtcata gtggctcacg cctgtaatcc caacactttg ggaggccaag gcgggtggat   52380
cacctgaggt taggagttcg agaccagcct gaccaacatg gtgaaaccct gtctctacta   52440
aatacaaaaa attagctagg catggtggca ggcacctgta atcccagcta cttggaaggc   52500
tgaggcagga gaactacttg aacctgggag gtggaggttg cagtgagccg agattgtgcc   52560
atgccattgc actctagccc ggcaacaaga gcaaaactgc ctcaaaaaaa aaaaaaaaa   52620 aaaaacacat agtaaagggt ctgctcattt aatagtaaac actttgcaaa tgcaagctat   52680
gtttcaaaac catttctcat ccattttat ttgactccca gcacccctg gaatcgctgg   52740 gggagaagat tttattccag agaccagtga aacacaggta aaggagaact aacgtgactt   52800
```

```
acccaaggtc acacagctag ttagcagtag atttggagct agagcctaga ctagggttgg   52860 caaactttc ccataaagag ccatgtaact atttcaggcc ttgcaggcca cgcattctca    52920
ctgcaactac tcacctacac cacatgatag catgaaagtg gtcacagaca aaacacaaac   52980
aagcaagtgc tgctgtttgc caatgaacat ttaggaacac aaatataaat gtcacatatt   53040
gtcagatgtc ccataatcgt attcatcttc tgattctcca ccagccattt acaaatgtaa   53100
aagccattct tggttggcag gccatgccaa catgtgttgg gtcggaactg ccccgcagac   53160
tagagtttgc caatcccaga ttgctgggag acttctcaat atctactaat agaataccac   53220
aaagccaaaa aaagacaaac cgtgatcatt cccaggctta ttacaatttt aactctccag   53280
tccagtcaaa attgcttgcc tagcaaacac caaacgtaac ccaggctcca ggtatctgac   53340
agcaatacag cttgcgcatg caggcggggt gttcaaactt ctctagaaaa caatgccttt   53400
ttatgggaat gccttttat gggaattttt gcacaaaatt tcaagttaag aaactttcca    53460
taaatacaca acgcatgctc tagccacagc tggtttcata tgctaactgc agaaggcatt   53520
tccgaaagca gcatgtgaag agtcctcctt aaatacagcg ttagggaaaa tgacaccctc   53580
tatcctcccc actgccccca ccaccaagaa ggaatttggg tctgtgttca gtaagaagaa   53640
atctggccag aaaggggtta atgcccttcc aggctgggat ctgataaatg gctgtgcaga   53700
aagcaggttc cctcactttg agatatgatg tcactaacct ttattgatcc actatcagag   53760
aactttgctt atctctctcc tgtgatatac tgccctcct gtgctcaact agtgtttaat    53820
acactgccgg gtgccttgca ctcctcatcg ctcagcactg cagagagagg ctgccacggg   53880
gaccatattt cacagagccg ggccttccca gcacagacgc ctcccagagt caaggggagc   53940
cagcacccac ctcccacctc ctcccaggcc gccaggtccc agctgcaccg agacagtggg   54000
tcgggtcagg gcagggcagg ataggacacg gcccctccgg gaccctgcgg cttctccttt   54060
ttttggggga gtgtggggac agagcttcag tcccaagatt cccctttttt ccaccatgaa   54120
gacaactgtc agccatgttc atgtgggaaa acataagcac ctccgagtca gacctcctat   54180
ttagagaaat gagcttcctg ttttccccct tccaaggtct caagacctca gtccaccggg   54240
aggtggaaaa caccatccat caaggtgccg gacagttgtt cgggagaagt cctgccagga   54300
agaaagccag agaacatgcc caggtgtggc caggcaggct cagatcccca agaagaacag   54360
ggctccagag cccggggcag tgtgatgctg ggctgccac acaccgggtt tgggggttggt   54420 cgctcctcct gccaacccac aggctaagga tgcatcaggc acagccttgg ccacacccaa   54480
gggtggggag agcccaaag caccaacaga caggggacga ttgttagaac tcaagacaca    54540
gaattccatc tccaataacc tcaaccgctc ggagggattc tcaagctctg ccaagacccc   54600
cactggtggc tctccaagaa gcccatggta caggctttgc ttctccgggc ccatccctgg   54660
gaaagggggc agtgggccgc ccagaaaaag tgagcagggg ccctcccaca gccccgggc    54720 acccaaaatt tgcctaattg aacattaaca agttgctaca ataaagttcc tctgttgtga   54780
gcagggaaac cttttcggca acaacaacag aagtcttgtt acaaactgct ctgaaagcca   54840
ggcttcagcc tcgacaggtg tgaacaagat ttcaacacct cctacaatac aatgcaatcc   54900
aaacaaaggg gaaagtcaat cccagcctcc tgaggtttct gcttgtctaa catcttcttc   54960
actcactcag cccaggggag ccaagtgcac cttcctcaag cccagcagca gagaagacct   55020
caccaaaggt agaccctctc cactgcctca acatggggcc atcttggctg cccagggca    55080 gttcggaaag tctctgctag gaacaggagt cctttcaatg gctcccacct gctcctggga   55140
```

```
ccccaaggcc ccttctatca cctcccaaat gcagctagca tcgatgaacc acactggcgt    55200
gtttcccaca tttcctcacc tgggttcgcc atcaccttca gcctcttgac aggtaaggag    55260
agtgaaaaag aggaaaatga gaaacgctcc ttggtcacag ggtccatgct gctccttcta    55320
ctaaagggga cacaagagcc tcctaaagct cccttccctg aaatgctgga gaaaagctga    55380
gacctcagga ctggatattt tatttaaaaa cttttttgtga gtgatgccac aggtagaaac    55440
acacaagaag tgtgtgttgg acgacggaag gaattatccc tcccattgat ttttcgctct    55500
ggagtattag agagaaaaca gcatttatct ggagatttct tcccaaagcc aaccacataa    55560 acggacttg aaaagagctt atcggacaaa cgatttgctc acaaggccat cgcccaagtg    55620
ggaatcccag cagggaactc gatcagcccc actgttcctg cgtggacatc tttaggtggc    55680
tgttgtcatt actcaacttc atgccaacga cagagaggct ggcctgggaa gtggcagagg    55740
ggagacattg gcaaaaatta caatggacaa aaaatgagtt ctttctctgt catgtctctg    55800
ctccaataag gagaatgcaa aatgtcaaca aacaaattc caaaaaagc agcatgcaca     55860 taaacacact tgaatccttc ctaatgtatc ttgggactcc tctttgatcc tctaattttc    55920
cacaaactct taggcatgtt ttgttttaat aagtgataaa tactaataac ccaacatcta    55980
atccaaacac ccattctcct cccagggcaa aggaaaggct attcacaaat ttttaaaag    56040 tggaagacag cctaaaaata tgccaggata atccccaaga ccggctactc tcaactttct    56100
ctacctccaa tcttggagcc cacccaaggg caagagtggc ctggagactc gctataaaat    56160
gtatgtgacc accacaatgg aattgctttg ccagacattt ttactaatga atctcatagc    56220
acggagacag atcccatata aggagttaag caggttcatt ctcctccacg ctgcccttc     56280 acctaccaga taagcaaggc aagtgccccc agttccatgg aaggagagca gaccacaaaa    56340
aggttagaag gctcaagtcc tcttttccagg tagctgggag gatgtaattg gtgaggcagg    56400
agattagaaa tatcggcagc ctctaagtaa gactttaatt tactggcaga tcaatagagc    56460
cggggttata ttggcaaagt gtctacagct ctattgactc acgcaatgcc tcttatcaat    56520
ttatcagaaa tctggaagtc agaagatatt gtttgaaggg aaaagagaaa aaaaaaaga    56580 agaagaaaca ggaagcatga gtccagagct agagcagtta gaaactaggg tccccaatga    56640
ccaacttgct accaagagtt tcgtaccaat gtgtctcctg caaagaaggc taatatgata    56700
catttggagt taacctgcct cccttgcacg cccctctcag ccttctcagg gattccattt    56760
tccataaacc ttgtaccctg ggagggggt gaatcctact gaagctggtc tgggattttt    56820
gttttgtgtt gtgtcttagc aaggagcaat tccttcctta ggttcagcca tactcgtcca    56880
agttacagaa gatccacact tctccacccc ttgtgtggtt tcctgctacc tctccattct    56940
actgcagcca gaattcctag ccttggcttc tttcttacca atccataaaa agatttcttt    57000
ttaggtaaat aggatattta tctcagcatc ccaatactcc caagaggtca caaggatcta    57060
tcagactaac aatggcactt ggtctcaaga agcgtaaaga aaacgaactc aagttctata    57120
aatcatcaca aatgttttca caaataatta atcttcgttt gaaaatgttt tgaaatatcc    57180
caggtagccg accaaaaaag cctggcggcg ggggggaag taaacattca cacttcacca    57240
aacccaaatg ttcacaccag cgaaggaagg aaggacgcag gaaaacacga gttcccgag    57300 tgtttctagc cagtaactct aggggcagg tcggggaaga aagagaggt ttggagcatt      57360 ccaggtatca ggaggccaaa gggaaaagcg atttttccttg gtttggagga accacaacct   57420
gcttttgatg atccatttg gtccctgcct catacaacaa atttctgctt aattgctgtt     57480
ttgcatttcg tggagacatc gagtaaacag tacttaagtg tttccagaca aaaacaataa    57540
```

```
ctcactaatg actaaggcac tgctaattaa aatgccccca tgatggcgtg actggactca    57600
gagccaccac agcaaacaga acgagctggg ccttgaatgc atgaaccaga acgcgggcgt    57660
gcagggcgga agatcctctg ctcctttctc tgcaggtcac cacgggccct ctggctgaaa    57720
agaaggccca ctgtgaccct tgctagaagg agagggcaga ggtgtggaga gaatgggagg    57780
agttagagtg gggaaggggg gtgaaggcac tgagatttca gagggaaggc agcaccccaa    57840
tagaatgcac attctagaac cttataagag taagtggcct ggcattgcct caaaacttta    57900
tgagctcctg agagcccta aagaaaaaaa aaatgtgtcc tactctagta gggagaaaat    57960
aagaagatgt gttaaaactg gccaaatagg ctgggcgcag tggctcacgc ctgtaattgc    58020
agcactttgg gatgccgagg agacaggag atcctgtctc tacaaaaaat taaaaaatta    58080
gccagacgtg gtgatgcatg cctacagtcc gagctactcg ggttgcggga ctgaggtggg    58140
aggatcgctt gagcccagga gatggaggtt gtagtgaacc atgattgtat cactacactc    58200
cagcctgggc gactgaacaa gaccctgtct caaaaaacac aaacaaaagc aaaacaaaaa    58260
aacaaaaaca aaaacctggc taaagaccct ttcctagtga ccacagtcat acaaggcatc    58320
cattcctaac tacccttta aaagaagat tcagaaagaa caaaaaaacc agaggtatac    58380
tcgaccacct gcccagtgct aaaggatttc tcaacgccat agtcagactt cacgagcgca    58440
tgcgacaaag taacaggaac ctagaaaact tctcttcgtc cccaaaaaga gaccaaaata    58500
actagccttc cccagagcgg gcagctttcc tcttcagtgc tcttcaactt tcagtcctac    58560
agatgggggc ctcccaacat cacttttta agctcagcat ttaaaaaaag aacaggaaaa    58620
aaaaaaagta gagacatccc agagtccaca cgcttgcaaa ggactttctt ttcctcctcc    58680
tccccccagc aggttaaaga cctgctagtt agcaacgaga gcggatggag acagtcatt    58740 ggaaccacag gggcctaata cccatttgta ttcacactca gacccttaa gcatataaaa    58800 ccggagaggt tgaactgttt acattcacct aatgctccag taaacaaatc agagccccag    58860 tggaggggt ttcaggcagg gctgcggcca gaccccactg ggtgccaggc agcaggagca    58920
ggatggggaa ggaagaaggt agatgcatgg aaaacagaag ccaggctctc atcccaaccc    58980
actcaagttt ctccccaagc ctgggccctc cttgacccca cgcgacaggg gagcagccct    59040
tccaggcctg agctccacca ccctccatgg acaggtgacc tcagctgcca gacacctcct    59100 tacccctac ccccagtacc ctggagccct gccagcaccc ccataaccc caccaatgac    59160 ctggagagga ggacagaaga ggaacggcct tgcaaagcac ctggagaaaa agggttaaa    59220 tgcccagtgt ctgactgagg gagaaacttc ccctcccttc caggcgcctc cgagggttcg    59280
tcctcaacta ctattgttat tcaagaactg cgtcttagct gagcagctcc cccgccgccc    59340
cccagcactg ggtcttgaca gaagtgaagc ggggctgcct ggtgtcccag cacgggcct    59400 gatcatatcc tctaaaacgt gaacagtttc aacttgactg ggggggaaagg gggcaggcgg    59460 ggggtggggg gggactggca ctccttttaa atgcagattt gaacttttca cccggggtca    59520
gacagctgcg atgctctgtc cccagcagag gccagcgccg ggccccttc cacctcacac    59580 tttcacagtt tttttcctgc ctgccaggag gccagcctgt taaggaatt cgatacctcc    59640 ctccctccaa acccaaatcc acaccgcgtt ctcagcttac caggggcaca aatcccactg    59700
gcatcctaga ggagagcctc aaatcgtagg aggctggctg ggtgctctgg gaacagcaat    59760
ggcaaaggaa aattgttgtt gtcacatgta ttgaccaagg aacgctaagg tcaacagtga    59820
gaagactcca ggacttcccg gccgctctga aagcatctga aagcagcatc ttctctaggg    59880
```

```
tacatttcac agtggcgctt tctgctagaa gccagcagac agttctcctt gctatttcac   59940
tgagaagagc tgtaatggta ccaaggctga aatcatttag ttttgaaaag aagtcacttc   60000
tgggtgaaca agaaaaactg taacgaactt aaaaaaaaaa aaaagtctag gatgggactg   60060
cttgcctcca ttacacccct gattctcatg gacaaggttg tttctgagtt ttccatgtca   60120
ccctctgtcc ctccatttct cctcctccaa tgggagacgc ccactggtcc tcgactaggg   60180
aaggtttcca ttccgcggca tcaagataag gcaagaaagc agaaatccaa ataaacacta   60240
agagaagaag gcgaggggaa gtttcttgct ggaatcggtg accctcccaa cagtggcagc   60300
tcctacaact ctcatcttgg ggggcactag agcctctaag agaaagtccc ctccaagcaa   60360
tgcaccacac agtccctgga ctagccaaac cggaagcctg tgtgtgtggt gctagaaatg   60420
actgtgaagt cagaaaaacc acaccaatta cctacaggta gaaggttcta gattcatgcc   60480
ttcctcctgc cccaaactag caacccacca cggagagggt gaaacgagca tttctagagg   60540
ctccctgcag ccctgtctgt gatttcagta atatacatga agcagtaagt ctgttgtaac   60600
aaacacacta gcactcacag gaatgaatga gagtggggct gtcccctgag gaggtggccc   60660
gtgccttgct gccactgctg gtcttctgcc tctgggaagg ttttcacagt caggtgagca   60720
cccccacctg tacgccagga agcagtttac agaaacactgg cacccaatg tcacagttct   60780 atctcctaac aatctcatga gcatgtcggg ggagccaggc atttctgacc aaacccgctg   60840
tgtgcagact gagcctgcac ccattcccca gtaaatgcaa gcagctggtc acaggggtga   60900
tggctgactt ggctccatca acagaatgtc tcagaagagc acagggcagc aatcttttat   60960
tccagagctg caccatccac taggtagcca ccgacccttg tcactaccga gcctgtgaca   61020
tgtggcttgt ctcgatagag atgtgctgaa ggtataaaaa tacaggactc caaagatttg   61080
gtacaaaaaa aagggatgta aaatatctca ttaatagttt tattaatatt gattacctgt   61140
ggaaatgata acctttggga tatactgggc taaatgtatt atgaaaattc attccacctg   61200
tttctcattg tttaatgtga ctaatagaaa atctaaaatt acctacgtgg cttacactgt   61260
atttctactg gatggtcctg tttcagaacc tctgcctgtc tttcaacttc agattcaggc   61320
gggattctaa gtgttctcgg atatgactga gacagacttc tcttgtctgt cttgaacatc   61380
tccctaaagc tacaatgtac tggctcccaa atgatacttt taaatgggct gaacaatctt   61440
agtatccaac aactcactgc caaactcaag tataaactaa gaaaaaataa atcacttctg   61500
ggacccacag cgtgctttta aaaataata ataggccagg cattgtggct cacacctgta   61560
atcctagcac tttgggaggc cgaggcaggt ggatcacttg agctcaggag ttcgagacta   61620
gcctggccaa catggcaaaa ccccgtctct actaaaaata caaacaaaa caaaattag   61680 ccgggcatgg tggaaaacca gcccacgctg gtagtcccag ctactcggga ggctgaggca   61740
ggaggactac ttgaacccag gaggaggaag gcacagtgag ctgagattgt gccactggat   61800
tccagcctgg gagacagagt gagaccctgt ctcaaaaaca aaataaaaat aagtcattta   61860
ctgtggttta ataccaggac tacccacgag gcttgtccaa aagtaagccg tctcctactc   61920
cagcctgatt tcttactatc aagagaagac ttctcccttt taactgccct tctgtaaaat   61980
atgcccagca ggggcctggt gtccaccttc tcccccaccc catacacaca taccacacag   62040
cacacgcgtg cgcgcgcata gacagactct ctctctctct gtctctctct ctctctacaa   62100
ctggggaggg ctgcgggagg aaggtgcagg cagcacagat gtggccccctt tcctattaga   62160 aagtccctat tctgccacta gggatcacaa ggccagtctc atttctctat gtaaatgaac   62220 ttttttagcca cctcctcaaa gaagaaaagc tgcacagatg cggaaggccg gtccagaggc   62280
```

```
acacaattac agccatttgc attcctccag cagccggatt agcacaggaa tgcgctctgc   62340
cgctttgtgg ggggaaaagg agtttaggaa gaaagggatg ggtgggggga tgtatttctc   62400
cctggtctgt ccacccaaag ctctatgata cgcttccact tctgtgagag tcagaaagtg   62460
gaaataactc ctgctcagct tctaaagagg gggaggttga aaaggcgcag ggaggaggag   62520
ggaggtggag gtagagggta gaggaagagg aggggagagg ggccggcagg agagagggag   62580 gaggggggact gggtgtatca ggggaactgc ccctcccggc gctttgatcc cctcggtcgg   62640
tcgctaggag aaaccaactt ttctccttgg gttaatcaaa accaaattac tcaggaatgt   62700
ggcaggacag gtctgaactt ccaggtccct ttgtctttga ggatttaaaa tgaaaaaaaa   62760
taaaattgtt aaagcagatg gccgtggcct actcaagagg tgaagcgaag agtctgaggg   62820
aagtcagacc acatctctca ccctccaaaa aaacacaccc gcaaacttcc tatgccaatt   62880
tattgtgaga gaagttattt ttgtagacaa catccaaaaa tcagaagaac tgcccatttc   62940
atccttactg ctgcgcaaat aaaagaccct caccccaccc tcccatcaac tataccttgt   63000
caaagtacaa atacaagaga accccagatt taagatacac ccgtatatca caacccgact   63060
attaaaagcg gagtccaaac tagctcaaga acatacgttt tccaaacaca aagtttggga   63120 gtattttttca gtgtaaagtt cttccttagg aatactgggg taaggaggta ttcaaatatc   63180
cggttgctat tcaaatgcat ccatgaaatt tcatggttac tgtaaaattc tgcatctctt   63240
taagttctaa gaaaagcggt ttttagggaa tgactcagag gagatatgaa atgtcccact   63300
gagtgacata agatcccact gctcatctgt cgtctagaaa aagcgaagaa cctgccaccc   63360
agggctgttc tgtttactag gaaagtctgc tgggtgtgct ggccagcccg gcgacagttt   63420
caataagtca agaggcaaca ggaaaaagct gacctcagag atgaaagaaa cctggggctt   63480
ggagctatat taaggcctcc acacctcctc cccggctcac agctctggca agcttgtggc   63540
actgtacaag atgggggcct gcacttcagg ctcctggaaa ctctagaatg caacaccctg   63600
gcatgtgcta tcattaggga cagtaaaaag tgacacagcc cagggcaccc aggagcagaa   63660
atatgaacag cccttcgtgt gttataaaat gctgctatgc ttcactgtaa aacctggctg   63720 accccccatgt ccccccaccca cccaaaaaag ataaaataaa caaacagagc accaccggtt   63780
aagctataga gccaggattc aaaagataaa gtgagaccaa cacacagcca tgactaccag   63840
cttgccataa atcgtaactg gccccaggca tacggttatc tgggaagctg cacaccaact   63900
tttaaaatac tcttcacctt atctttaagc ccagtcaaac acacacatac atcacccttc   63960
ttagatctcg gccattagta ttccatttag actttccaaa acaaggtcat cccagagggt   64020 ccttccccctc tttccagtca cagctgtgga cttctcatccc cttgtccaac aaaagggacc   64080
ttgtacacaa aattaacctg aagcattagt ctgtgtggtg cgagagtcca cggggccctc   64140
gggatattga ctcccccacc ccccccaacta tccaggctca gcccaaaatc ctgtctagag   64200 ggcttccccca ctgtggaggc tggggggagct tccctagaga ttagagaccc tgccccttca   64260
gaatccgctt ctcagctgca gctgtgcagc caaggaaggc cttacctttc agagaataaa   64320
cagaagaaaa aaacttcctc cctgactcag taacagtaga aaacgacctg acgtcatggc   64380
tgcaaaggcc cagaatcatc tgagaactaa gccatccaat atgacggcca caactgcacg   64440
cggcttctga gcactggaca tggggctggt tctgagcgtt gagaccagaa catcatggtg   64500
aaatcgtggg ttgctgaaaa tatctgtttt aaagttaatt ccacctgttt cttttttactt   64560 tttatgaatg actactagga aatgtacaat tacatataag cttgtactct ctctctctct   64620
```

```
ctctctattg gacagcacta gagaggtgca aatgttacca cctcaagtgc tagcacatta    64680
ccatgctcta aaaggaaaga ctcttccttt ttattactat tattattatt attattatta    64740
ttattgagtc gggatgtcac tctgtcaccc aggctggagt gcagtggcac aatcacggct    64800
caatgcagcc tctacttcct gggctcaagc aatccaccca cctcagcctc ccgagtagct    64860
aggaatacag gcgtgcacca ccacgcccgg ctaattttgg tattttttt gtagagacaa     64920 ggtcttgcca tgttgctaag gctggcctcg aaccctggg ctcaaactc tgggctcaag      64980 agatcctcct gcctcagcct cttgagtggc tgggactaca ggcacatgcc accgagccta    65040
gctaattaaa aaaaaaaaa aaagtttgt agagacaggg tctccctatg ttgcccaggc      65100
aggtctcaag cccctgagct caagcaatcc gcctgcctct gcctcccaaa gtgctgagat    65160
tacaggcttg agccaccaca cccagcccag attcttcatt tttaaatgcc aaaaagacca    65220
gtgtaaaatt gagcaaacag catcatctgg tatcaggtgg aatcacatac gcagaggctg    65280
ctcaactccc aggctgcagt gaaggtgtct aaatgggggg agtggccggg aacctgccat    65340
tgttttagac caggagaagc aaatgtaacc tctatttcag gtgttcttaa ctggaggcga    65400
ttttgcctcc caagggaca gtgggcaatt cctgcagaca ttttgattg tcacatcaag      65460 ggaagaaggt gctactggca tctagtgggg agatgccagg gatactaaat gtcctacaat    65520
gcacaaggtg gcccactccc cccaaaaaca attatcccca aacatcaaca gtgccaacac    65580
acaaccagga agtgaccagg cctgagatcc acccaagtat ctctttttt attttttat     65640 ttttagtaga gatggagttt caccacgttg cccaagctga tctcaaactc ctgaggtcag    65700
gcaatcctgc ctaggcctac caagtgctg ggattacagg catgagccac catgcacaac     65760
ccaagcaaat ttttaatact cagatatcca ggagcaggag gggacatccc tttgcaaaat    65820
ggcttctctc cagagctcg                                                 65839

<210> SEQ ID NO 2
<211> LENGTH: 599
<212> TYPE: DNA
<213> ORGANISM: Homo sapiens

<400> SEQUENCE: 2
aaggtaatcc aattacacca atgtgttttc ctgatcacca ggggaatcct cagccttccc      60
cgtaatctgc tcctaacgcc ccatttagtc caatgctgca ctccaatcac caaaaatgta    120
gacagggttc ccactcctac agccagatga gaggtgcctg ccccttctcc aaaatgggat    180
ggtgaaatta acacatttca gaaaatattc tacagagtcc agagtccagg gcacgcttta    240
tccttgagga aaataataaa tgtcgagtcc taatggcatg tcaattaaag gggtcaccay    300
aaacaagctt tcaaactttt cccctccact cttcgcccgt gcctctccaa tctgggtgcc    360
ctggaggacg gaacgggaac tgcagatcca ggcactccat tatggcaacc cagcaagcag    420
ttcagcacgg acttaatgag ctcttggaag gaaacaggaa gtctataaag taatttaaat    480
aacttccagt cctgaaataa aggaaattaa accgctggca caaacctctc tgatggacac    540
cttctttgtc cctccgatca caactacaac tacagcggtc atattgctct ccccaagac    599

<210> SEQ ID NO 3
<211> LENGTH: 599
<212> TYPE: DNA
<213> ORGANISM: Homo sapiens

<400> SEQUENCE: 3
agtaagtgac caatcaagag gctattgctg taaattagac aagggattat ggtgttttgg     60
```

```
gtgagagaag tggaggtgga gaaaatgaag gaattcaaaa tgtattttgg atgaagcatt      120
ttcatgactg ttgaggaatt gggcattttg gggttgaagg agatggttca tgcttgagca      180
attggctggt tggaggagct gtttgctgaa atggggacca ttgaaggaga agcaaaattt      240
gatgggaaga tttaaaaata tgaactcagg atatcctttc tttaatattt agaaatatay      300
caggattgtt tttctgattc aactttccat attttctaag cagctgcaga atatattgag      360
aagggaaatg aaatttacat ttgtaatcct catgttttga ttttttaaaaa caaacttgtc      420 attggctatg ttatgttcct tagtagctat catgcagatc ttgagacaga tagaatatat      480
taaccgccac acattcattt tgcggagcta tgtcaagaga agtatggaga aaccggttgc      540
actttataat aaaagcaagt ctacttggca ttgtgtgaca gagatgttgg ttagatttc       599
```

`<210>` SEQ ID NO 4
`<211>` LENGTH: 599
`<212>` TYPE: DNA
`<213>` ORGANISM: Homo sapiens

`<400>` SEQUENCE: 4

```
agcatagata gccatctgac atgtacttcc caagtcagag aaaattgaaa catttaaaaa       60
atgaaaaata tgtgatctgt taagtaaaga tttataaatt cccacaataa tacacaactc      120
aataaacatg caaatagaga agatacaatt cttttctaca ataagttgtt tcttgaccaa      180
agtagcagat taatagaatt agaaaatcat caaataatgg caaataaag ggagaaattt       240 tcacagatta attatataat ctcaaaataa tactgagaaa ttagttatta atttgccaay      300
ccaaagaaac tcttctttaa tatctttatt gtggtatgtt ggcttcaacc ttacattttc      360
caggtgatta atgttgaaaa gaatagaaga acatacacaa cacactcaca tacacataaa      420
gtagaagaaa gaaatcaaag gaaaagaaa attggcaaaa atagtacttg gtgtgtgtgc       480
gtgcatgtgt gtatttgaga aaggggagaa ggtgtttatt ttttgagttc tgtaaatttt      540
tctgtgaaat ttaacttata tcatcatgaa attaaaataa aacatgtaac accttaata       599
```

`<210>` SEQ ID NO 5
`<211>` LENGTH: 599
`<212>` TYPE: DNA
`<213>` ORGANISM: Homo sapiens

`<400>` SEQUENCE: 5

```
caaaatatct gccagagctc cagccagtag gtctgcattt taggagaata gaaagggaaa       60
gacaaggggc aagcaggctc ttccctcatt ggcatgaaaa aacccccagta agagagttg       120 caggaaacac caatcaaaga cttatattta aatttcattg accagcccct taactgcaag      180
ggaggatggg gagtaaagct ttttagcttg gcacactttc cccctaagca aaatctgagt      240
tatgtttcta aggcacaaag agagagagga tattgggtaa gcagcctgca gtctttgccr      300
tgaaggatct taatcattca tcagtaagta tgatcttttt ttttttttaaa tgtcaattgt      360 ttctttaaga ttttttagttt ctcttcaaag tctataggta aatcactgaa atttatccag      420
atcccagcct tcacatccag ggatttttggt gtaccaccat ctactcaatg ctccccgtcc      480
tcctacccca tcaaatgagc ttcgtttgtt tttccttttat ctctaagtgg tatgacacca      540
tctgctgttt tctgcttttg acccagagcc atgtctggca tcatcagact aatcaagag       599
```

`<210>` SEQ ID NO 6
`<211>` LENGTH: 599
`<212>` TYPE: DNA

<213> ORGANISM: Homo sapiens

<400> SEQUENCE: 6

| taaaaagggt | gctctgagag | gtgaggtgac | ttgcctaaag | tcacacagca | aggaaacaga | 60 |
| gccaagcttg | acagatagct | gtgcagcgtc | ttttcacctg | gatgaggtta | agtctttgat | 120 |
| agactggaag | agtgtgtgtg | tgtgtgtgtg | tgtgtgtgtg | taaccaccaa | agtgtacatt | 180 |
| tccctgaaaa | gggtttctgg | gttgcagggt | ctgatataaa | aagcactatt | ttagtggcaa | 240 |
| agctctgcct | attttttattt | cagtgctgag | aatgcttgat | gatggaaaaa | ctgactttgy | 300 |
| aaagaaattg | tgtataagac | gctaaagtgc | ctctcgaaat | cccatcacag | aaaattagct | 360 |
| gaaaggtagt | ggtgatggat | aaggcagtta | ttgatgtgaa | attgcccaat | ttggggaaag | 420 |
| tctgaaggct | gcaagtgttc | atctcctcct | ccttcccacc | gcctcagcgg | ctcgccccgt | 480 |
| ctagtctttc | cggttggatt | tctctttgtt | tagcaatggg | aacagagagg | agccaaaaag | 540 |
| acaacgtaga | aaatcccagg | ggtgggtgtg | gggaatatga | tctcgactga | gaattccag | 599 |

<210> SEQ ID NO 7
<211> LENGTH: 599
<212> TYPE: DNA
<213> ORGANISM: Homo sapiens

<400> SEQUENCE: 7

| aactatgtgg | aaagcagtac | agtgattcct | cagagaacta | aaggcagaac | taccattgga | 60 |
| ctcagcaatc | ccattactgg | gtatatactc | agaggaattt | aaatcattct | accataaaga | 120 |
| cacatgcaca | cgaatgttca | tggcagcttt | gtgcatttgg | agatgaatac | agttctaaat | 180 |
| aggacagcct | ggaaaggcct | cagtagaaag | aataacactt | cataaaagat | ctgaagagg | 240 |
| tgaggatata | ttttcacaat | taatcatgca | catctgtttc | ccttagatct | tcaaagttay | 300 |
| gaacatactt | caattatttt | tgtatgctgg | ctcctaggga | gcagccacac | ttagtaagta | 360 |
| cataatgttg | gatgaaatat | ctcaggtttc | tgaacttaaa | tttcagttgt | cttcaacta | 420 |
| cacaaggctt | tgtacttcag | aaaattgatg | aatttgaata | caacactgat | gtaaatcaac | 480 |
| agcacaacta | gaacttctac | actctcgctg | ctcaacaact | taatttaata | ggggtatgat | 540 |
| tttctaaatg | ttgtagccca | acacatgcag | gaaacatgaa | gaaaactgaa | tcctaagaa | 599 |

<210> SEQ ID NO 8
<211> LENGTH: 599
<212> TYPE: DNA
<213> ORGANISM: Homo sapiens

<400> SEQUENCE: 8

| aagctatggg | ggcaagacac | aatagtggtg | gtctggccca | agagcctgtg | tacagtggaa | 60 |
| atatgctgct | tgttacttag | tatgctgcat | gctgagctag | tactaacaac | aaaaaaacgg | 120 |
| ttttcaatga | aaaatcagtg | attaataaca | cgaaatgaaa | tccaacagta | tgtaacttta | 180 |
| ggtacttata | atagggttgg | gatgagattt | gttgcaatgc | ctcctgaagt | cccttaaaac | 240 |
| tcagtccaca | tcagcagcta | ctccttgaga | gtattgcaag | tagaacaaag | catttcaaay | 300 |
| cacagaatcc | tttcaatgtt | tttatatttc | tccaccataa | tcttgcagca | cccctcctc | 360 |
| caaagggcag | cactgaatgc | acagacacat | gacacattga | tatgatcaag | gttgattggt | 420 |
| ggcttcccac | atatcatgtg | aggtccacaa | gagactaaag | attgctagag | tattgtggaa | 480 |
| ccctcagtga | tctgaattca | acttatccat | tcattcattc | aacagatact | caacaggaac | 540 |
| ctactacatg | ccagatactc | ttctagagac | taaagataga | gcggtgaaca | aagctgaat | 599 |

<210> SEQ ID NO 9
<211> LENGTH: 599
<212> TYPE: DNA
<213> ORGANISM: Homo sapiens

<400> SEQUENCE: 9

| | | | | | |
|---|---|---|---|---|---|
| ctgccaaaca | aaggattagt | catattcaaa | ttaaatctgg | agttgttgca | aaagttctac | 60 |
| cactttcact | gcaacaatta | tttctgtata | ttcacataca | ctctaatgaa | agcgaaagat | 120 |
| acaaatataa | cagaaaaaaa | gaaagcacag | agcagttgga | gaaatccaaa | caaagttccc | 180 |
| agtaatctgt | cttacttaca | aagaatgggc | ttcatctttg | tttgtgagcc | gccaatatgt | 240 |
| gcatgaaata | tatcagtcct | agagaaactg | ccctcttatc | agagaaatgg | tcttttatam | 300 |
| ccctatgaga | tcaaatattt | acatttgagg | ttactatgtt | ttataattta | ccacttatga | 360 |
| ccatatgttt | tttaaattgt | agttcctgaa | agactagata | gtgtctatga | aaacacacag | 420 |
| aaatactagt | gacacatgca | tctaagcgtg | agatataaga | caaattctcc | taacaactaa | 480 |
| caatgaaatt | gcaatgagct | taattctgtt | gcttgtattc | tggaagcatg | gaacttaatg | 540 |
| ggcatagtct | gtcaactaaa | ttttcctaag | taactattat | ggcctggata | ttgtgctgg | 599 |

<210> SEQ ID NO 10
<211> LENGTH: 599
<212> TYPE: DNA
<213> ORGANISM: Homo sapiens

<400> SEQUENCE: 10

| | | | | | |
|---|---|---|---|---|---|
| tgcacagcgc | gacggtggtg | gtacattccc | agcgctgggc | ccgcctccac | cgctgcattc | 60 |
| accaccggtc | tcctgtagca | gtcagcacac | tgcccctccc | ccgcctgcag | ccactaatct | 120 |
| tctgtgtcca | ggagtttgcc | taggctgggc | cttccctgtt | aagggaacta | tgcaatatgt | 180 |
| ggtctttaag | agacttattt | ttgcaatctt | gaaataattc | ctgtacttaa | cctctcaccc | 240 |
| acattcccat | ctcactcagt | ggttgtctgt | tctctgtcta | ggcattagga | cacttaaagk | 300 |
| cctgtgactt | gcacatcgtc | ttctaagccg | ggtctgaatc | tttcgctcat | ttcatcacag | 360 |
| tttagacaca | gaccaatata | ttacaatgat | tcaacgatgg | gctatgaaag | ctcagccatg | 420 |
| caaatctaaa | ctcacacatg | tatacatgaa | aataatatat | cagttttggg | caaaacatca | 480 |
| ggtttcagaa | aacactacca | aggaggaaag | caaggactta | aaactctcaa | ggacatggca | 540 |
| acagaagtcg | tctaacgtaa | aacagagagg | gaaggctaag | agagtgagca | gagcatcag | 599 |

<210> SEQ ID NO 11
<211> LENGTH: 599
<212> TYPE: DNA
<213> ORGANISM: Homo sapiens

<400> SEQUENCE: 11

| | | | | | |
|---|---|---|---|---|---|
| gtgttatatt | tgtcctagtt | atcatatact | gtattgcaga | ttctaaacat | gcctaggatg | 60 |
| gaatgtgttc | ttggcaactg | gtagccagtc | tccctctgaa | acccttctca | gaaacaaggg | 120 |
| tcccattggc | aatcagtcca | acacactggt | tatcagcagg | taatgctgga | aatatacatt | 180 |
| ggtcaaactg | aaggaaactc | tggtgattta | attcaccta | cttttgttga | tttcatttac | 240 |
| aggaaaaaag | tatatatgtg | tgtatatatc | tatgtagata | gatatagctg | tagtacatay | 300 |
| acacatatac | tgttttattt | gatctagtat | atgcaacatg | tccatcccaa | gaaataattc | 360 |
| aaaactggga | atcatcacta | acaccttcta | actacagatt | aaggcaagaa | ttcaccgata | 420 |

```
ggcagaagtt tgtttctgcc tcatggtctt gactcagtaa ctggcacttt ttacttttgc    480
ttaaaaattt atattgagac agggtcaaac tccgttgcct agactggaat gaagtggtgc    540
aatcacagct cactgcagcc tcaacctccc tggctcacgt aatcctccga cctcagcct     599

<210> SEQ ID NO 12
<211> LENGTH: 599
<212> TYPE: DNA
<213> ORGANISM: Homo sapiens

<400> SEQUENCE: 12
tcagatttcc agcctgagtt tgccatccca agtctacata caagcttcat tttctgttct     60
gaaatcactc actctcctcc ctctcccatc atgaaacccc atcaggaaca gcaaggggc    120 agagagacac tcactatccc tccagcagcc tctgcctgtg gatggccagg tcagggaggg    180
acaggagcgc aaagcactgg ggacaaggag tgtcaccatg cacgactcct ccagcctgtt    240
gtctgacaag gcttaaaaga accctctccg ggtctggttc tcctgcatgg tgcacacttm    300
aggaggtgaa tccaagggcc ttttccagcc agggtttctg aatgtctcca tgctgagagg    360
tgaagtactt gacatttggc tgccatgctg ttgtgagcac gtctgatttt gcacaaggca    420
tgtggaaatc agaatgtacc tgtcacaggt gtcaacctct gtctgacggg tacagatctg    480
gagagtggtc acaacttgct gttcctcgtt gcaaatatct tctttgtgac ctttcatctg    540
cagatgagca ggcaccaggc tttacatgct aatgtgtccc tttgcattcc atggttttc    599
```